US012766032B2

(12) United States Patent
Doraiswamy et al.

(10) Patent No.: US 12,766,032 B2
(45) Date of Patent: Oct. 20, 2026

(54) THERMAL SYSTEMS AND METHODS FOR CRYSTALLINE LENS REMOVAL

(71) Applicant: Lhotse Medical, Inc., San Francisco, CA (US)

(72) Inventors: Anand Doraiswamy, Oakland, CA (US); Andrew Schieber, Tustin, CA (US); Matthew Flowers, Laguna Niguel, CA (US)

(73) Assignee: Lhotse Medical, Inc., San Francisco, CA (US)

( * ) Notice: Subject to any disclaimer, the term of this patent is extended or adjusted under 35 U.S.C. 154(b) by 0 days.

(21) Appl. No.: 18/426,039

(22) Filed: Jan. 29, 2024

(65) Prior Publication Data

US 2024/0252351 A1 Aug. 1, 2024

Related U.S. Application Data

(60) Provisional application No. 63/530,443, filed on Aug. 2, 2023, provisional application No. 63/442,058, filed on Jan. 30, 2023.

(51) Int. Cl.
*A61F 9/007* (2006.01)
*A61B 18/00* (2006.01)
(Continued)

(52) U.S. Cl.
CPC ................................ *A61F 9/00736* (2013.01); *A61B 2018/00642* (2013.01); *A61B 2018/00714* (2013.01);
(Continued)

(58) Field of Classification Search
CPC ........ A61F 9/00736; A61F 2009/00887; A61F 2009/00889; A61M 25/0075;
(Continued)

(56) References Cited

U.S. PATENT DOCUMENTS

| | | | |
|---|---|---|---|
| 3,937,222 | A | 2/1976 | Banko |
| 4,538,608 | A | 9/1985 | L'Esperance, Jr. |

(Continued)

FOREIGN PATENT DOCUMENTS

| | | |
|---|---|---|
| AU | 2017-232627 | 10/2018 |
| AU | 2020-277300 | 5/2020 |

(Continued)

OTHER PUBLICATIONS

Spirochkin, "Hydrodynamic Analysis and Irrigation Device Design for the Coaxial and Bimanual Phacoemulsification Techniques in Cataract Surgery", Engineering Centre of Nuclear Equipment Strength (ENES).

(Continued)

*Primary Examiner* — Beverly M Flanagan
*Assistant Examiner* — Abigail M Ziegler
(74) *Attorney, Agent, or Firm* — Foley & Lardner LLP

(57) ABSTRACT

This disclosure relates to thermal emulsification systems and methods for cataract removal. The thermal emulsification systems can apply heat to the crystalline lens of the eye, resulting in the emulsification of the crystalline lens. The emulsified crystalline lens can be aspirated from the capsular bag of the eye. The thermal emulsification systems can include one or more elements that can be heated to apply localized heat to the crystalline lens to avoid unintentional damage to other ocular components and cellular structures of the eye, such as the capsular bag. The thermal emulsification systems can supply heated fluid to the lens to apply localized heat to the lens to avoid unintentional damage to other ocular components and cellular structures of the eye, such as the capsular bag.

18 Claims, 49 Drawing Sheets

(51) Int. Cl.
*A61B 18/04* (2006.01)
*A61F 9/008* (2006.01)
*A61M 25/00* (2006.01)

(52) U.S. Cl.
CPC ............... *A61B 2018/00744* (2013.01); *A61B 2018/00791* (2013.01); *A61B 2018/044* (2013.01); *A61B 2018/046* (2013.01); *A61B 2218/002* (2013.01); *A61B 2218/007* (2013.01); *A61F 2009/00887* (2013.01); *A61F 2009/00889* (2013.01); *A61M 25/0075* (2013.01)

(58) Field of Classification Search
CPC .... A61B 2218/002; A61B 2018/00642; A61B 2018/00791; A61B 2018/044; A61B 2018/046
See application file for complete search history.

(56) References Cited

U.S. PATENT DOCUMENTS

| | | | | |
|---|---|---|---|---|
| 4,955,883 | A | 9/1990 | Nevyas et al. | |
| 5,257,988 | A | 11/1993 | L'Esperance, Jr. | |
| 5,437,678 | A | 8/1995 | Sorensen | |
| 5,616,120 | A | 4/1997 | Andrew et al. | |
| 5,830,214 | A * | 11/1998 | Flom | A61B 18/1482 604/35 |
| 5,865,790 | A | 2/1999 | Bair | |
| 5,885,279 | A | 3/1999 | Bretton | |
| 6,074,358 | A | 6/2000 | Andrew et al. | |
| 6,206,848 | B1 * | 3/2001 | Sussman | A61F 9/00736 606/107 |
| 6,331,171 | B1 | 12/2001 | Cohen | |
| 6,440,103 | B1 | 8/2002 | Hood et al. | |
| 6,527,766 | B1 | 3/2003 | Bair | |
| 6,544,211 | B1 | 4/2003 | Andrew et al. | |
| 6,676,628 | B2 | 1/2004 | Sussman et al. | |
| 6,827,142 | B2 * | 12/2004 | Winkler | G05D 23/1393 165/247 |
| 6,860,868 | B1 * | 3/2005 | Sussman | A61F 9/00736 604/35 |
| 9,125,720 | B2 | 9/2015 | Jia et al. | |
| 9,629,747 | B2 | 4/2017 | Clauson et al. | |
| 10,016,300 | B2 | 7/2018 | Kuebler et al. | |
| 10,231,870 | B2 | 3/2019 | Clauson et al. | |
| 10,736,777 | B2 | 8/2020 | Keller | |
| 10,881,551 | B2 | 1/2021 | Kraemer et al. | |
| 2002/0099400 | A1 | 7/2002 | Wolf et al. | |
| 2004/0254532 | A1 | 12/2004 | Mehier | |
| 2011/0144632 | A1 | 6/2011 | Bourne et al. | |
| 2011/0213359 | A1 | 9/2011 | Ben-Nun | |
| 2012/0055473 | A1 * | 3/2012 | Gavriely | A61B 18/04 128/204.17 |
| 2013/0178841 | A1 * | 7/2013 | Reid, Jr. | A61B 18/1815 606/46 |
| 2015/0142039 | A1 * | 5/2015 | Kirkemo | A61B 1/32 606/185 |
| 2019/0269557 | A1 | 9/2019 | Clauson et al. | |
| 2019/0365567 | A1 | 12/2019 | Balkenbush et al. | |
| 2020/0306083 | A1 | 10/2020 | Clauson et al. | |
| 2022/0233353 | A1 | 7/2022 | Carter et al. | |
| 2023/0028279 | A1 * | 1/2023 | Govari | A61M 1/71 |
| 2024/0050142 | A1 * | 2/2024 | Zhang | A61B 18/02 |

FOREIGN PATENT DOCUMENTS

| | | |
|---|---|---|
| EP | 0398975 | 11/1990 |
| WO | WO 2001-76518 | 10/2001 |
| WO | WO 2018-211507 | 11/2018 |
| WO | WO 2018-217579 | 11/2018 |

OTHER PUBLICATIONS

International Search Report and Written Opinion for International Application No. PCT/US2024/013383 dated May 15, 2024.
Hughes et al., "Awualase for cataract extraction", Eye , dated 2007, vol. 21, pp. 191-194.

* cited by examiner

THERMAL SYSTEMS AND METHODS FOR CRYSTALLINE LENS REMOVAL

CROSS REFERENCE

This application claims the priority benefit of U.S. Provisional Application No. 63/530,443, filed Aug. 2, 2023, and U.S. Provisional Application No. 63/442,058, filed Jan. 30, 2023, which are hereby incorporated by reference in their entireties. All applications for which a foreign or domestic priority is identified in the Application Data Sheet as filed with the present application are hereby incorporated by reference under 37 CFR 1.57.

FIELD

This disclosure relates to systems and methods for removing a natural lens of an eye.

BACKGROUND

As the eye ages, proteins in the crystalline lens begin to break down and clump together. This clumping of proteins makes a cloudy area in the crystalline lens known as a cataract that negatively impacts vision. This condition may be addressed with cataract surgery, wherein the crystalline lens with the cataract is removed from the eye and an intraocular lens ("IOL") is implanted in its place.

SUMMARY

During a cataract surgery, an incision may be made through the cornea (e.g., corneal margin) and/or sclera to access inside the eye. A ultrasonic emulsification tool, which may be a phacoemulsification probe, may be inserted through the incision and apply ultrasound to the cataract, breaking the cataract into fragments to be aspirated out of the eye. Ocular components and cellular structures (e.g., ocular organelles) are delicate and can be easily damaged by the ultrasound energy. Accordingly, cataract removal solutions that avoid unintentional damage to ocular components and cellular structure are desirable.

Additionally, applying ultrasound energy to the cataract and removing by way of aspiration may take ten minutes or longer, which may be nearly eighty percent of the time to perform a cataract surgery and, as such, may be prone to safety issues, which can at least include breakage of the capsular bag, damage to zonules, iris rupture, synechia uveitis, etc. Accordingly, cataract removal solutions that shorten the time to remove cataracts and/or ease removal of cataracts are desirable. Further, cataract removal solutions that preserve the capsular bag are desirable. Additionally, cataract removal solutions that reduce damage to surrounding ocular tissue (e.g., capsular bag, zonules, iris, etc.) are desirable.

The thermal systems (e.g., thermal emulsification systems) described herein may at least address one or more of the issues identified above. The thermal systems described herein may apply heat (e.g., localized heat, ultra-localized heat) to the crystalline lens to soften, melt, liquefy, emulsify, flow, and/or ease removal (e.g., aspiration) of the crystalline lens.

The crystallin lens of the eye may emulsify (e.g., liquify) when exposed to heat. Crystallins are the predominant structural proteins in the crystalline lens, which may at least include alpha-crystallins, and betagamma-crystallins. Crystallins and/or other proteins, biopolymers, and/or other lens material may emulsify (e.g., liquify) when exposed to heat. The lens may emulsify when exposed to a temperature between 64-70 degrees Celsius (e.g., exposed to a heated element and/or a heated fluid at 64-70 degrees Celsius). The lens may begin to emulsify when exposed to 64-66 degrees Celsius for under five minutes, which can leave some fragments of the lens intact. The lens can be almost completely emulsified when exposed to 66-68 degrees Celsius for one to three minutes, which can leave some thready fragments of the lens intact that can be aspirated with a fine gauge needle (e.g., 18-22 gauge needles). The lens can be completely emulsified when exposed to 68-70 degrees Celsius for under one minute, which can then be aspirated by a fine gauge needle (e.g., 30 gauge needle). Accordingly, 64-70 degrees Celsius can be a workable range for emulsifying the lens. 66-70 degrees Celsius can be the preferred range. 68-70 degrees Celsius can be more preferred if complete emulsification of the lens is desired in a shortened duration of time (e.g., less than one minute), which may be preferred to reduce the overall quantity of energy (e.g., Joules) imparted to the eye compared to lower temperatures. For example, exposing the lens to 64-66 degrees Celsius (e.g., heated element and/or heated fluid) for five minutes can impart more total energy to the eye compared to 68-70 degrees Celsius for less than one minute. Temperatures above 70 degrees Celsius needlessly expose the eye to more energy than needed to emulsify the lens. During testing, localized phase changes to a gaseous state were observed with temperatures above 70 degrees Celsius to 80 degrees Celsius. Above 80 degrees Celsius, rapid phase change to a gaseous state was observed instead of emulsification. The phase change to the gaseous state was observed to damage (e.g., burn) surrounding structures of the eye (e.g., capsular bag, zonules, etc.), which can include compromising the integrity of the capsular bag. Accordingly, temperatures above 70 degrees Celsius should not be used. The lens may be softened at temperatures below 64 degrees Celsius, but if emulsification is desired, temperatures below 64 degrees Celsius should not be used. The application of heat may be localized (e.g., ultra localized) to avoid unintentional damage to the ocular components (e.g., capsular bag) and cellular structures, which may avoid the damage that can be incurred with the application of ultrasound. The emulsification (e.g., liquification) of the lens may enable the lens (e.g., proteins, biopolymers, other components of the lens) to cleanly separate from the capsular bag.

The thermal systems may include one or more elements (e.g., wire(s), contact(s), mesh(es), loop(s), lasso(s), basket(s), scoop(s), heating zone(s), heater(s), heater cartridge(s), electrode(s), etc.) that may be temperature controlled (e.g., regulated). For example, the temperature of the one or more elements may be raised and/or lowered. The temperature of the one or more elements may be regulated based on aspiration and/or irrigation flow to compensate for convection loses (e.g., losses due to aspiration, irrigation, etc.). Heating of the one or more elements may be achieved either directly or indirectly with various energy sources, which may at least include heat, radio frequency, laser, electricity (e.g., current), resistive heating, inductive heating, etc. The one or more elements may be disposed at the distal end of the thermal system such that the one or more elements may apply heat to the crystalline lens while the remainder of the system that contacts the anatomy of a patient is insulated with no, or at least diminished, heat transfer. The one or more elements can be used to emulsify the nucleus/cortex of the lens first or the peripheral regions of the lens first. The temperature of the one or more elements may be altered based on the density of the regions lens (e.g., higher temperatures for denser regions compared to lower temperatures for less dense regions). For example, the nucleus/cortex may be denser than peripheral regions. Accordingly, the temperature of the one or more elements may be higher for the nucleus/cortex compared to the peripheral regions.

The thermal systems may utilize a heated fluid (e.g., saline solution) to emulsify (e.g., liquify) the lens of the eye. The thermal systems can include an irrigation cannula (e.g., tip) that can be introduced into the eye. The irrigation cannula can include an opening through which heated fluid can flow to the lens. The heated fluid can quickly emulsify (e.g., liquify) the lens for aspiration. The flow rates and/or pressure for irrigation and/or aspiration can be adjusted for speed and/or efficacy during and after emulsification of the lens. The opening of the irrigation cannula and/or a corresponding aspiration opening can be adjusted in size for speed and/or efficacy. The heated fluid can be used to penetrate and liquify the nucleus/cortex of the lens first or the peripheral regions of the lens first. The temperature of the heated fluid can be altered based on the density of the regions of the lens, as described herein. The heated fluid can be introduced into the capsular bag to emulsify the lens. In some variants, the emulsified lens and heated fluid can be aspirated as the heated fluid is being introduced. In some variants, the emulsified lens and heated fluid can be irrigated with a fluid at a lower temperature and aspirated subsequent to emulsification of the lens.

The thermal system may include aspiration features to aspirate the softened, melted, and/or emulsified crystalline lens from the eye. For example, the system may be incorporated with an aspiration tip (e.g., phaco tip). The distal end of the aspiration tip may have localized elements (e.g., concentric rings, wires, discrete contacts, etc.) to apply heat. The aspiration tip can be fluidically coupled to a system to supply heated fluid that can be directed to the lens. In some variants, the thermal systems may include oscillating features, reciprocating features, retractable features, sharp distal ends, vibrating features, chomp features, grounding features, aspiration features, cryo features, temperature cycling features, etc. The thermal systems described herein may be incorporated (e.g., coupled, attached, integrated, etc.) with an existing irrigation and/or aspiration device, which may include positioning one or more heating elements on the distal tip of the existing device and/or fluidically coupling to a system to supply heated fluid that can be directed to the lens. The thermal emulsification systems may be handheld and/or portable. The thermal systems may include a rechargeable battery. The thermal emulsification systems may include an irrigation receptacle (e.g., tank, compartment, bag) and/or an aspiration receptacle (e.g., tank, compartment, bag), which may or may not be disposable. The one or temperature controlled elements may include a nickel and titanium alloy (e.g., Nitinol). In some variants, heating may be applied with aspiration (e.g., to provide heat/cool cycle). In some variants, only the distal tip of the thermal system is heated while the rest is insulted.

The thermal systems can be used to remove the lens without significant damage to the capsular bag and/or zonules of the eye. For example, a small incision may be made in the capsular bag to access the lens therein. The heated element(s) and/or heated fluid may be introduced through the small incision to emulsify the lens. The emulsified lens can be aspirated out of the same small incision or another small incision. With the lens removed, an intraocular lens can be placed in the bag. In some variants, with the lens removed, a material (e.g., gel) can be injected into the capsular bag. The material can fill the capsular bag. The material can include a refractive index that is the same as or at least similar to the natural lens.

In some variants, the techniques described herein relate to an irrigation device. The irrigation device can include a tube including an outlet. The irrigation device can include a temperature sensor disposed at the outlet. The irrigation device can include a heater configured to heat fluid flowing through the irrigation device such that a temperature of the fluid at the outlet is within a range. The outlet of the tube can be directed at a lens within a capsular bag of an eye to emulsify the lens.

In some variants, the techniques described herein relate to an irrigation device, wherein the range is 68-70 degrees Celsius.

In some variants, the techniques described herein relate to an irrigation device, further including a first fluid line through the irrigation device that bypasses the heater.

In some variants, the techniques described herein relate to an irrigation device, further including a second fluid line through the irrigation device that wraps around the heater.

In some variants, the techniques described herein relate to an irrigation device, further including a valve configured to direct the flow of fluid through the first fluid line or the second fluid line.

In some variants, the techniques described herein relate to an irrigation device, wherein the valve includes a spring that biases the valve to a configuration in which the flow of fluid is directed through the first fluid line.

In some variants, the techniques described herein relate to an irrigation device, further including a user interface configured to be manipulated to overcome the biasing force of the spring to position the valve in another configuration in which the flow of fluid is directed through the second fluid line.

In some variants, the techniques described herein relate to an irrigation device, wherein the temperature sensor is disposed within a lumen of the tube.

In some variants, the techniques described herein relate to an irrigation device. The irrigation device can include a tube including an outlet that can deliver fluid to a lens within a capsular bag of an eye. The irrigation device can include a first fluid line. The irrigation device can include a second fluid line. The irrigation device can include a heater that can heat the fluid flowing through the second fluid line. The irrigation device can include a valve that can direct the fluid through the first fluid line to bypass the heater or the second fluid line for heating.

In some variants, the techniques described herein relate to an irrigation device, wherein the heater is configured to heat the fluid such that a temperature of the fluid flowing out the outlet is 68-70 degrees Celsius.

In some variants, the techniques described herein relate to an irrigation device, wherein the valve is biased to direct the fluid through the first fluid line.

In some variants, the techniques described herein relate to an irrigation device, further including a user interface that is configured to be manipulated to overcome the bias of the valve to direct the fluid through the second fluid line.

In some variants, the techniques described herein relate to an irrigation device, wherein the second fluid line is coiled around the heater.

In some variants, the techniques described herein relate to an irrigation device, further including a temperature sensor disposed at the outlet.

In some variants, the techniques described herein relate to an irrigation device, wherein the heater is configured to adjust energy output based on a temperature sensed by the temperature sensor.

In some variants, the techniques described herein relate to an irrigation device. The irrigation device can include a tube including an outlet that can deliver fluid to a lens within a capsular bag of an eye. The irrigation device can include a heater that can heat the fluid such that a temperature of the fluid at the outlet is 68-70 degrees Celsius.

In some variants, the techniques described herein relate to an irrigation device, further including a temperature sensor at the outlet, wherein the heater is configured to adjust energy output based on the temperature of the fluid at the outlet.

In some variants, the techniques described herein relate to an irrigation device, including a fluid line wrapped around the heater.

In some variants, the techniques described herein relate to a method of removing a lens within a capsular bag. The method can include positioning an outlet of an irrigation tube of an irrigation device at a nucleus of the lens within the capsular bag. The method can include positioning an inlet of an aspiration tube of an aspiration device proximate the outlet of the irrigation tube. The method can include delivering heated fluid at 68-70 degrees Celsius to the lens to emulsify the lens. The method can include aspirating the heated fluid and emulsified lens from the eye.

In some variants, the method can include heating fluid. The method can include adjusting the heating of the fluid based on a sensed temperature of the heated fluid at the outlet of the irrigation tube.

In some variants, a thermal system for removing a crystalline lens from an eye is disclosed herein. The system can include a distal tip that can have an aspiration opening and/or a heating element. The distal tip can be inserted into the eye to position the heating element at the crystalline lens. The system can include a power source that can direct electrical energy to the heating element to cause a temperature of the heating element to rise. The heating element can heat the crystalline lens to at least a glass transition temperature of the crystalline lens such that the lens flows or softens, which can ease aspiration through the aspiration opening.

In some variants, the system can include an irrigation port that can irrigate a fluid in the eye.

In some variants, the heating element can be disposed around the aspiration opening.

In some variants, the heating element can include a ring shape.

In some variants, the heating element can include a plurality of discrete elements that can be distributed circumferentially around the aspiration opening.

In some variants, the heating element can be disposed on a distal facing surface of the distal tip.

In some variants, the heating element can be retractable.

In some variants, the heating element can oscillate.

In some variants, the heating element can vibrate.

In some variants, the heating element can include a sharp tip.

In some variants, the heating element can include a cutting edge.

In some variants, the heating element can include a wire.

In some variants, the heating element can include a wire forming a loop.

In some variants, the heating element can include a plurality of wires forming a plurality of loops.

In some variants, the heating element can include a mesh.

In some variants, the system can include a receptacle to receive the aspirated crystalline lens.

In some variants, a distal end of the tip can be angled.

In some variants, the system can include insulation to protect the eye.

In some variants, the temperature of the heating element can cycle.

In some variants, the heating element can include a nickel and titanium alloy.

In some variants, the power source can direct electrical energy to the heating element to raise the temperature of the heating element to 64-70 degrees Celsius.

In some variants, the power source can direct electrical energy to the heating element to raise the temperature of the heating element to 66-70 degrees Celsius.

In some variants, the power source can direct electrical energy to the heating element to raise the temperature of the heating element to 68-70 degrees Celsius.

In some variants, the power source can direct electrical energy to the heating element to heat the crystalline lens to 64-70 degrees Celsius.

In some variants, the power source can direct electrical energy to the heating element to heat the crystalline lens to 66-70 degrees Celsius.

In some variants, the power source can direct electrical energy to the heating element to heat the crystalline lens to 68-70 degrees Celsius.

In some variants, the heating element can soften the crystalline lens.

In some variants, the heating element can emulsify the crystalline lens.

In some variants, the system can be a portable, handheld device.

In some variants, a thermal system for cataract surgery is disclosed herein. The system can include a tip that can have a temperature controlled element. The tip can be inserted into an eye to position the temperature controlled element at a crystalline lens of the eye. The temperature controlled element can heat the crystalline lens.

In some variants, the system can include an energy source that can direct energy to the temperature controlled element to raise a temperature of the temperature controlled element.

In some variants, the energy source is a battery.

In some variants, the temperature controlled element can include a heat conductive material.

In some variants, the system can include an aspiration opening that can aspirate the heated crystalline lens.

In some variants, the temperature controlled element can heat the crystalline lens to soften the crystalline lens.

In some variants, the temperature controlled element can heat the crystalline lens to emulsify the crystalline lens.

In some variants, the temperature controlled element can heat the crystalline lens to a glass transition temperature such that the lens flows.

In some variants, the temperature controlled element can heat the crystalline lens to a melting temperature.

In some variants, the temperature controlled element can reach 64-70 degrees Celsius.

In some variants, the temperature controlled element can reach 66-70 degrees Celsius.

In some variants, the temperature controlled element can reach 68-70 degrees Celsius.

In some variants, the temperature controlled element can heat the crystalline lens to 64-70 degrees Celsius.

In some variants, the temperature controlled element can heat the crystalline lens to 66-70 degrees Celsius.

In some variants, the temperature controlled element can heat the crystalline lens to 68-70 degrees Celsius.

In some variants, the system can include an irrigation port.

In some variants, the temperature controlled element can be disposed on a distal facing surface of the tip.

In some variants, the temperature controlled element can be retractable.

In some variants, the temperature controlled element can oscillate.

In some variants, the temperature controlled element can vibrate.

In some variants, the temperature controlled element can include a sharp tip.

In some variants, the temperature controlled element can include a cutting edge.

In some variants, the temperature controlled element can include a wire. The wire can be retractable.

In some variants, the temperature controlled element can include a wire forming a loop.

In some variants, the temperature controlled element can include a plurality of wires forming a plurality of loops.

In some variants, the temperature controlled element can include a mesh.

In some variants, the system can include a receptacle to receive aspirated crystalline lens.

In some variants, a distal end of the tip is angled.

In some variants, the system can include insulation to protect the eye.

In some variants, the temperature controlled element can include a nickel and titanium alloy.

In some variants, the system can be a portable, handheld device.

In some variants, a temperature controlled element connected to an energy source is disclosed herein. The energy source can direct energy to the temperature controlled element to cause a temperature of the temperature controlled element to rise. The temperature controlled element can be disposed on an aspiration device and positioned at a crystalline lens to heat the crystalline lens.

In some variants, the energy source can be a battery.

In some variants, the temperature controlled element can include a conductive material.

In some variants, the temperature controlled element can heat the crystalline lens to soften the crystalline lens.

In some variants, the temperature controlled element can heat the crystalline lens to emulsify the crystalline lens.

In some variants, the temperature controlled element can heat the crystalline lens to 64-70 degrees Celsius.

In some variants, the temperature controlled element can heat the crystalline lens to 66-70 degrees Celsius.

In some variants, the temperature controlled element can heat of the crystalline lens to 68-70 degrees Celsius.

In some variants, the temperature controlled element can reach 64-70 degrees Celsius.

In some variants, the temperature controlled element can reach 66-70 degrees Celsius.

In some variants, the temperature controlled element can reach 68-70 degrees Celsius.

In some variants, the temperature controlled element can include a wire.

In some variants, a method of removing a crystalline lens is disclosed herein. The method can include inserting a tip of a thermal system into an eye to position a temperature controlled element at a crystalline lens. The method can include applying energy to the temperature controlled element to heat the crystalline lens. The method can include aspirating the heated crystalline lens.

In some variants, applying energy to the temperature controlled element to heat the crystalline lens can include raising the temperature of the crystalline lens to 64-70 degrees Celsius.

In some variants, applying energy to the temperature controlled element to heat the crystalline lens can include raising the temperature of the crystalline lens to 66-70 degrees Celsius.

In some variants, applying energy to the temperature controlled element to heat the crystalline lens can include raising the temperature of the crystalline lens to 68-70 degrees Celsius.

In some variants, the temperature controlled element can be heated to 64-70 degrees Celsius. In some variants, the temperature controlled element can be heated to 66-70 degrees Celsius. In some variants, the temperature controlled element can be heated to 68-70 degrees Celsius.

In some variants, the energy can be electrical energy.

In some aspects, the techniques described herein relate to a method of removing a crystalline lens. The method can include flowing a fluid at 64-70 degrees Celsius to the crystalline lens of an eye to emulsify the lens. The method can include aspirating the emulsified lens from the eye.

In some aspects, the techniques described herein relate to a method, wherein the fluid is at 66-70 degrees Celsius.

In some aspects, the techniques described herein relate to a method, wherein the fluid is at 68-70 degrees Celsius.

In some aspects, the techniques described herein relate to a method, further including cutting through a capsular bag of the eye to access the lens.

In some aspects, the techniques described herein relate to a method, wherein cutting through the capsular bag of the eye includes flowing the fluid at the capsular bag to cut the capsular bag.

In some aspects, the techniques described herein relate to a method, further including introducing an irrigation cannula into the eye and introducing an aspiration cannula into the eye, wherein the irrigation cannula is configured to flow the fluid to the crystalline lens, and wherein the aspiration cannula is configured to aspirate the emulsified lens from the eye.

In some aspects, the techniques described herein relate to a method, further including positioning the irrigation cannula and aspiration cannula on opposing sides of an optical axis such that an opening of the irrigation cannula faces an opening of the aspiration cannula.

In some aspects, the techniques described herein relate to a method, wherein the irrigation cannula and the aspiration cannula are juxtaposed to each other such that axes of the irrigation cannula and aspiration cannula are parallel to each other.

In some aspects, the techniques described herein relate to a method, wherein the irrigation cannula is disposed inside of the aspiration cannula.

In some aspects, the techniques described herein relate to a method, further including advancing a member through the irrigation cannula to engage the crystalline lens.

In some aspects, the techniques described herein relate to a method, further including heating the member.

In some aspects, the techniques described herein relate to a method, wherein the member is a wire.

In some aspects, the techniques described herein relate to a method, wherein the irrigation cannula includes a closed end with one or more openings disposed through a side wall.

In some aspects, the techniques described herein relate to a method, wherein the closed end includes a curved outer periphery.

In some aspects, the techniques described herein relate to a method, wherein the closed end includes a curved inner surface.

In some aspects, the techniques described herein relate to a method, wherein the irrigation cannula includes a curved portion configured to redirect flow of the fluid in a distal direction to a proximal direction.

In some aspects, the techniques described herein relate to the method of 88, wherein the irrigation cannula includes an opening that faces in the proximal direction.

In some aspects, the techniques described herein relate to the method of any of 78-84, wherein the irrigation cannula includes a flared portion that gradually increases an internal lumen of the irrigation cannula until an opening.

In some aspects, the techniques described herein relate to the method of any of 78-84, wherein the irrigation cannula includes a cutting edge disposed on a distal end.

In some aspects, the techniques described herein relate to a method, wherein the aspiration cannula is disposed inside of the irrigation cannula.

In some aspects, the techniques described herein relate to a method, wherein the aspiration cannula includes a closed end with one or more openings disposed in a side wall.

In some aspects, the techniques described herein relate to a method, wherein the aspiration cannula includes a cutting edge.

In some aspects, the techniques described herein relate to a method, wherein the cutting edge is disposed around a distal opening of the aspiration cannula.

In some aspects, the techniques described herein relate to a method, wherein the aspiration cannula includes a flared distal end.

In some aspects, the techniques described herein relate to a thermal system for cataract surgery, the system including: a tip configured to deliver a fluid at 64-70 degrees Celsius to the crystalline lens of an eye to emulsify the lens; and an opening configured to aspirate the emulsified lens from the eye.

In some aspects, the techniques described herein relate to a system, wherein the fluid is at 66-70 degrees Celsius.

In some aspects, the techniques described herein relate to a system, wherein the fluid is at 68-70 degrees Celsius.

In some aspects, the techniques described herein relate to a system, wherein the system is a handheld device.

In some aspects, the techniques described herein relate to a system, wherein the system is retrofitted to a phaco machine.

In some aspects, the techniques described herein relate to a system, further including a fluid reservoir to hold the fluid prior to delivery.

In some aspects, the techniques described herein relate to a system, further including a heating element configured to heat the fluid.

In some aspects, the techniques described herein relate to a system, further including a temperature sensor.

In some aspects, the techniques described herein relate to a system, wherein the temperature sensor is at the tip.

In some aspects, the techniques described herein relate to a system, wherein the heating element is configured to adjust the temperature of the fluid based on a temperature detected by the temperature sensor.

In some aspects, the techniques described herein relate to a system, further including a pump.

In some aspects, the techniques described herein relate to a system, further including a valve configured to impede the delivery of the fluid.

In some aspects, the techniques described herein relate to a system, further including a waste reservoir configured to hold aspirated material.

In some aspects, the techniques described herein relate to a thermal system for cataract surgery, the system including a heating element configured to heat a fluid for delivery to a crystalline lens of an eye at 64-70 degrees Celsius to emulsify the lens.

In some aspects, the techniques described herein relate to a system, wherein the heating element is configured to heat the fluid for delivery to the crystalline lens of the eye at 66-70 degrees Celsius.

In some aspects, the techniques described herein relate to a system, wherein the heating element is configured to heat the fluid for delivery to the crystalline lens of the eye at 68-70 degrees Celsius.

In some aspects, the techniques described herein relate to a system, further including a fluid reservoir.

In some aspects, the techniques described herein relate to a system, wherein the heating element is configured to heat the fluid in the fluid reservoir.

In some aspects, the techniques described herein relate to a system, further including a temperature sensor, wherein the heating element is configured to adjust the temperature of the fluid based on feedback from the temperature sensor.

In some aspects, the techniques described herein relate to a thermal system for cataract surgery, the system including: an irrigation cannula configured to deliver a fluid at 64-70 degrees Celsius to a crystalline lens of an eye to emulsify the lens; and an aspiration cannula configured to aspirate the emulsified lens from the eye.

In some aspects, the techniques described herein relate to a system, wherein the irrigation cannula is configured to deliver the fluid at 66-70 degrees Celsius.

In some aspects, the techniques described herein relate to a system, wherein the irrigation cannula is configured to deliver the fluid at 68-70 degrees Celsius.

In some aspects, the techniques described herein relate to a system, wherein the irrigation cannula and aspiration cannula are configured to be positioned on opposing sides of an optical axis such that an opening of the irrigation cannula faces an opening of the aspiration cannula.

In some aspects, the techniques described herein relate to a system, wherein the irrigation cannula and the aspiration cannula are configured to be juxtaposed to each other such that axes of the irrigation cannula and aspiration cannula are parallel to each other.

In some aspects, the techniques described herein relate to a system, wherein the irrigation cannula is disposed inside of the aspiration cannula.

In some aspects, the techniques described herein relate to a system, further including a member configured to be advanced through the irrigation cannula to engage the crystalline lens.

In some aspects, the techniques described herein relate to a system, wherein the member is configured to be heated.

In some aspects, the techniques described herein relate to a system, wherein the member is a wire.

In some aspects, the techniques described herein relate to a system, wherein the irrigation cannula includes a closed end with one or more openings disposed through a side wall.

In some aspects, the techniques described herein relate to a system, wherein the closed end includes a curved outer periphery.

In some aspects, the techniques described herein relate to a system, wherein the closed end includes a curved inner surface.

In some aspects, the techniques described herein relate to a system, wherein the irrigation cannula includes a curved portion configured to redirect flow of the fluid in a distal direction to a proximal direction.

In some aspects, the techniques described herein relate to the system of 128, wherein the irrigation cannula includes an opening that faces in the proximal direction.

In some aspects, the techniques described herein relate to a system, wherein the irrigation cannula includes a flared portion that gradually increases an internal lumen of the irrigation cannula until an opening.

In some aspects, the techniques described herein relate to a system, wherein the irrigation cannula includes a cutting edge disposed on a distal end.

In some aspects, the techniques described herein relate to a system, wherein the aspiration cannula is disposed inside of the irrigation cannula.

In some aspects, the techniques described herein relate to a system, wherein the aspiration cannula includes a closed end with one or more openings disposed in a side wall.

In some aspects, the techniques described herein relate to a system, wherein the aspiration cannula includes a cutting edge.

In some aspects, the techniques described herein relate to a system, wherein the cutting edge is disposed around a distal opening of the aspiration cannula.

In some aspects, the techniques described herein relate to a system, wherein the aspiration cannula includes a flared distal end.

Neither the preceding summary nor the following detailed description purports to limit or define the scope of protection. The scope of protection is defined by the claims.

BRIEF DESCRIPTION OF THE DRAWINGS

The abovementioned and other features of the embodiments disclosed herein are described below with reference to the drawings of the embodiments. The illustrated embodiments are intended to illustrate, but not to limit, the scope of protection. Various features of the different disclosed embodiments can be combined to form further embodiments, which are part of this disclosure.

FIG. 9D-2 illustrates the intact capsular bag after emulsification with heated fluid and aspiration of the crystalline lens.

DETAILED DESCRIPTION

Although certain embodiments and examples are described below, this disclosure extends beyond the specifically disclosed embodiments and/or uses and obvious modifications and equivalents thereof. Thus, it is intended that the scope of this disclosure should not be limited by any particular embodiments described below.

Figure 1A:
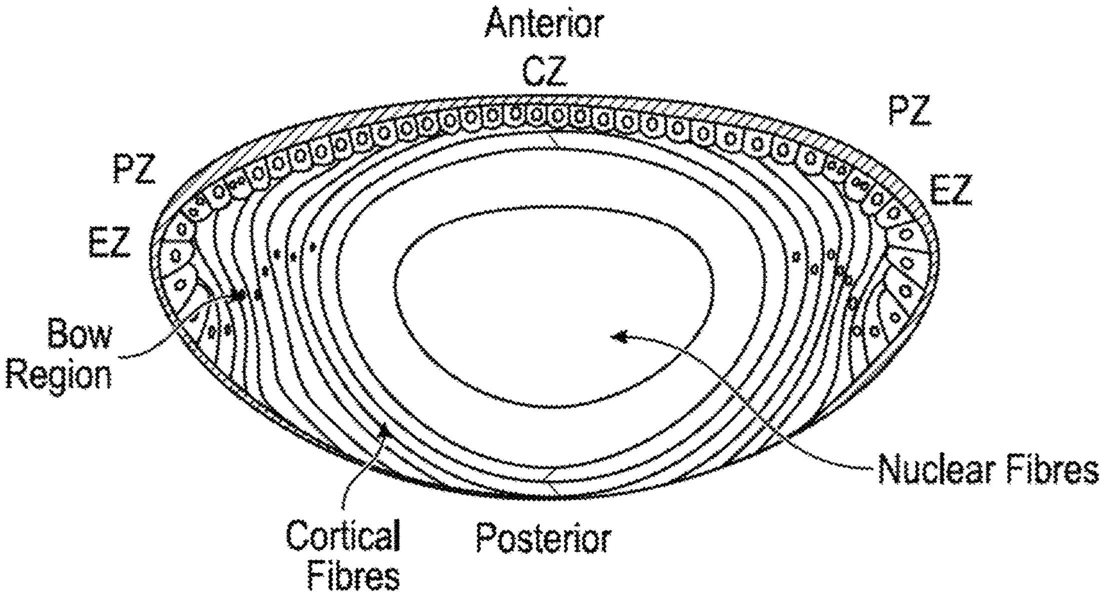
FIGS. 1A-1D illustrate schematics of a crystalline lens of a human eye.
Figure 1B:
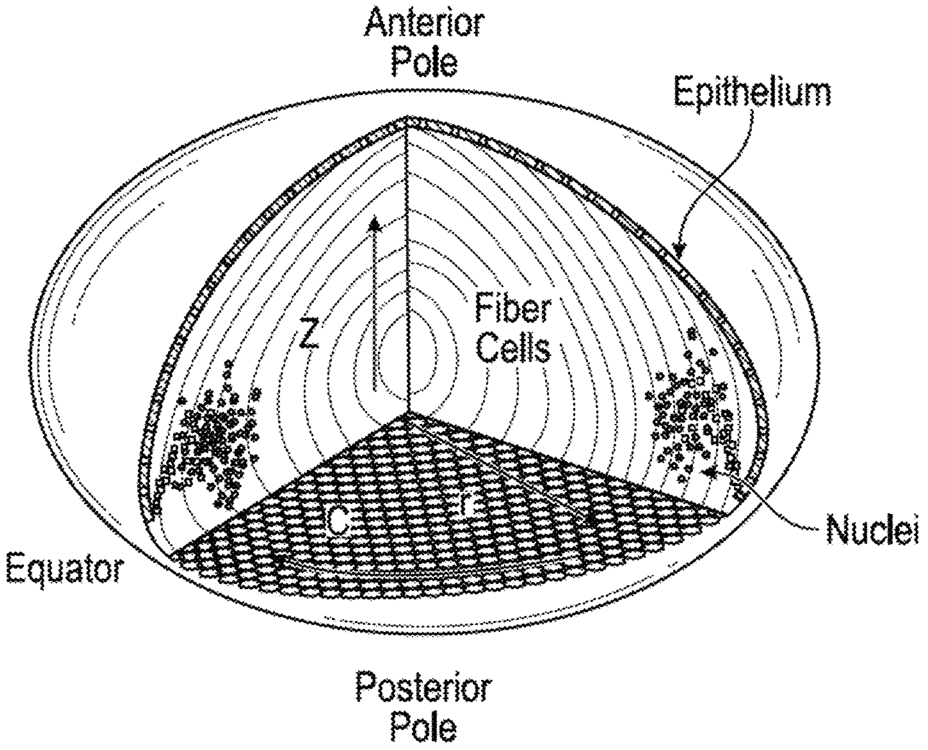
Figure 1C:
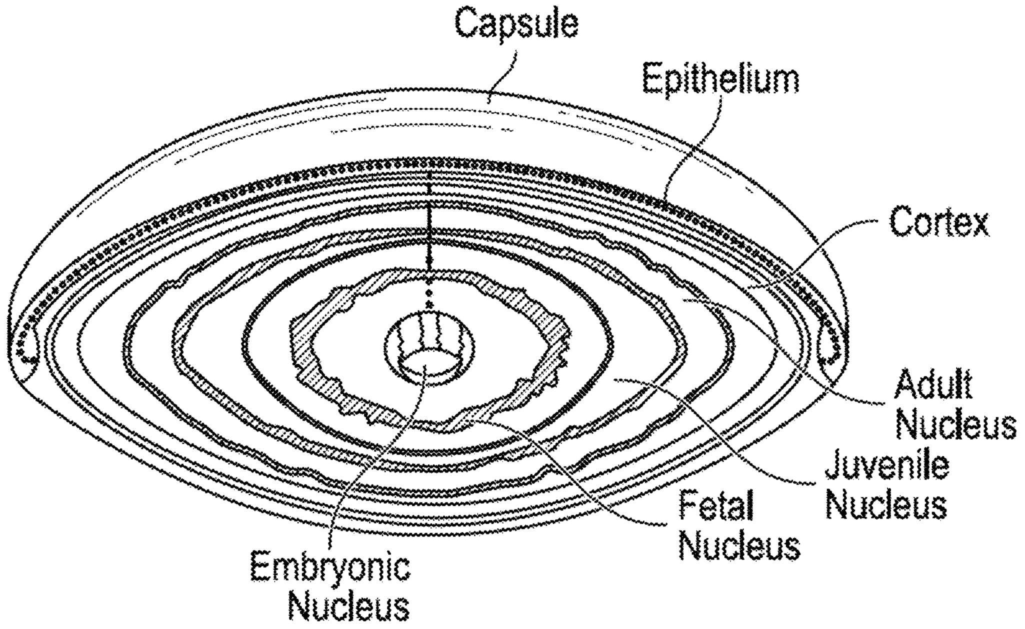
Figure 1D:
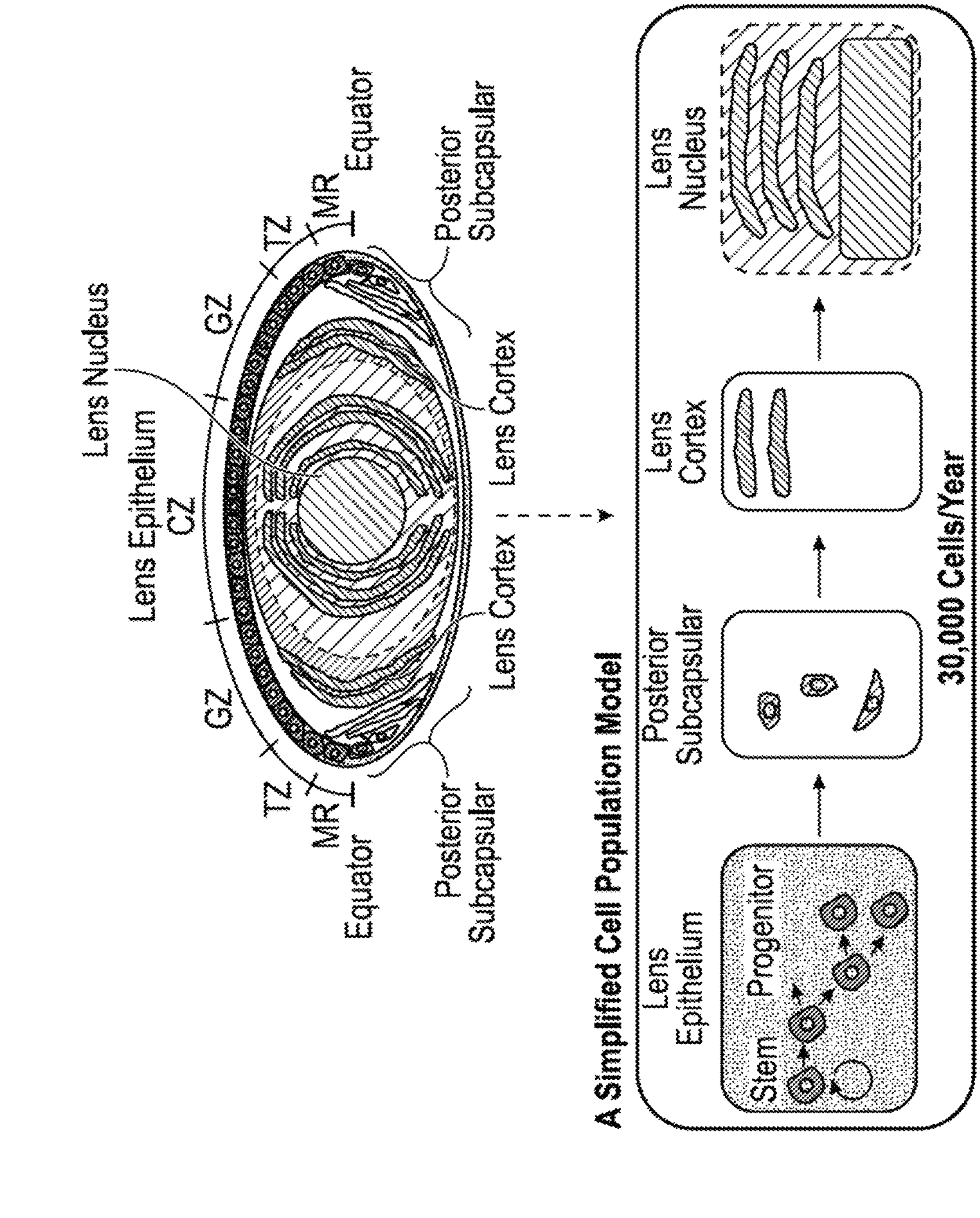

FIGS. 1A-1D illustrate schematics of a crystalline lens of a human eye. As illustrated, the lens of the human eye can include a nucleus in a central region of the eye. The lens can include a lens cortex radially outward of the nucleus. The lens can include a posterior subcapsular radially outward of the lens cortex. As illustrated in FIG. 1C, the lens can be disposed inside of a capsule, which can be referred to as the capsular bag. The lens can include a lens epithelium disposed at the anterior. The lens can include a cortex radially inward of the epithelium, an adult nucleus radially inward of the cortex, a juvenile nucleus inward of the adult nucleus, a fetal nucleus radially inward of the juvenile nucleus, and an embryonic nucleus radially inward of the fetal nucleus. A representation of the cell population of the various regions of the lens is shown in FIG. 1D.

Figure 2:
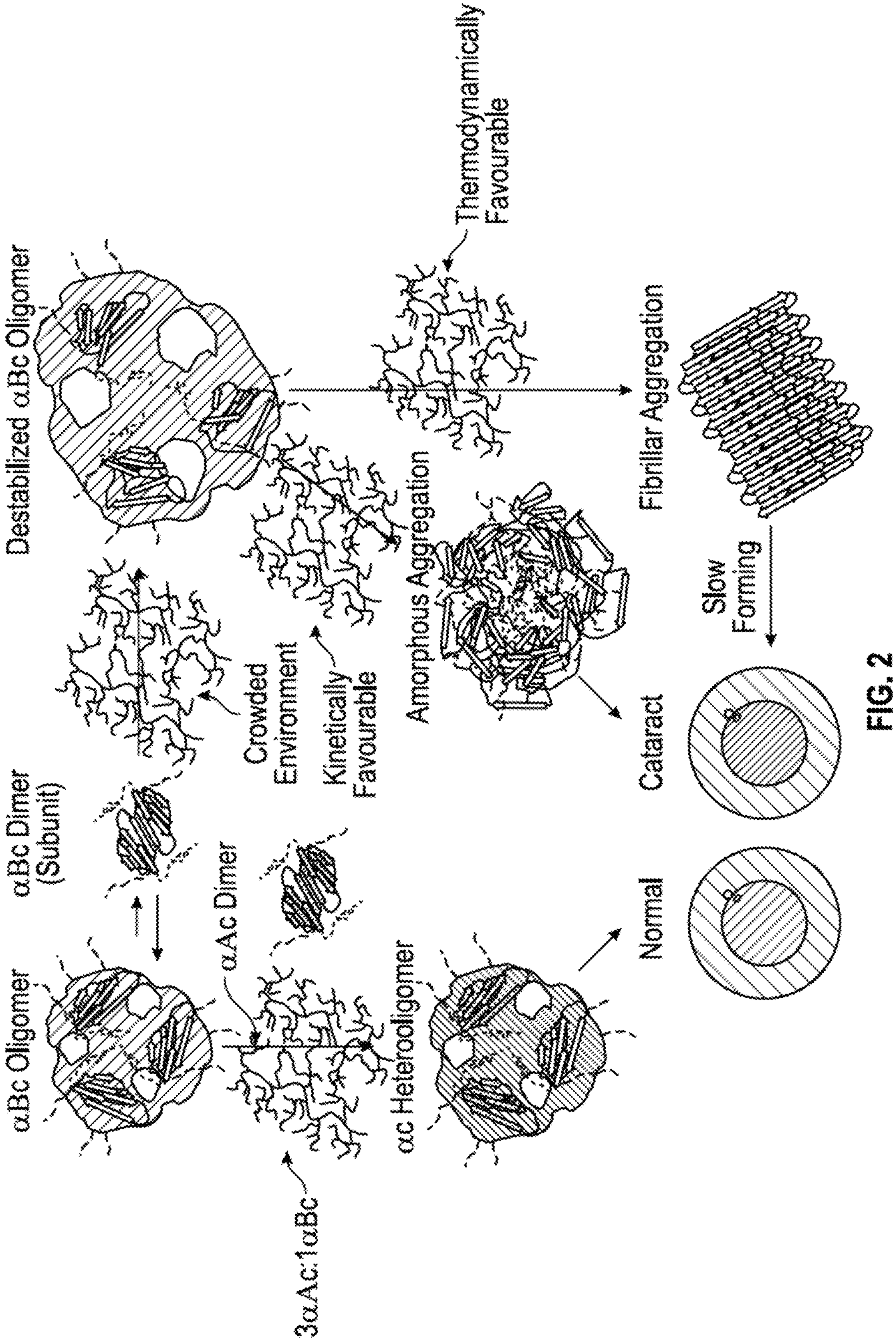
FIG. 2 illustrates the cataract formation process.

As the eye ages, proteins (e.g., crystallins) and/or biopolymers in the crystalline lens can begin to break down and clump together. This clumping of proteins can make a cloudy area in the crystalline lens known as a cataract that negatively impacts vision. FIG. 2 illustrates a schematic of a cataract formation process.

Figures 3A, 3B, 3C, 4A, 4B, 4C:
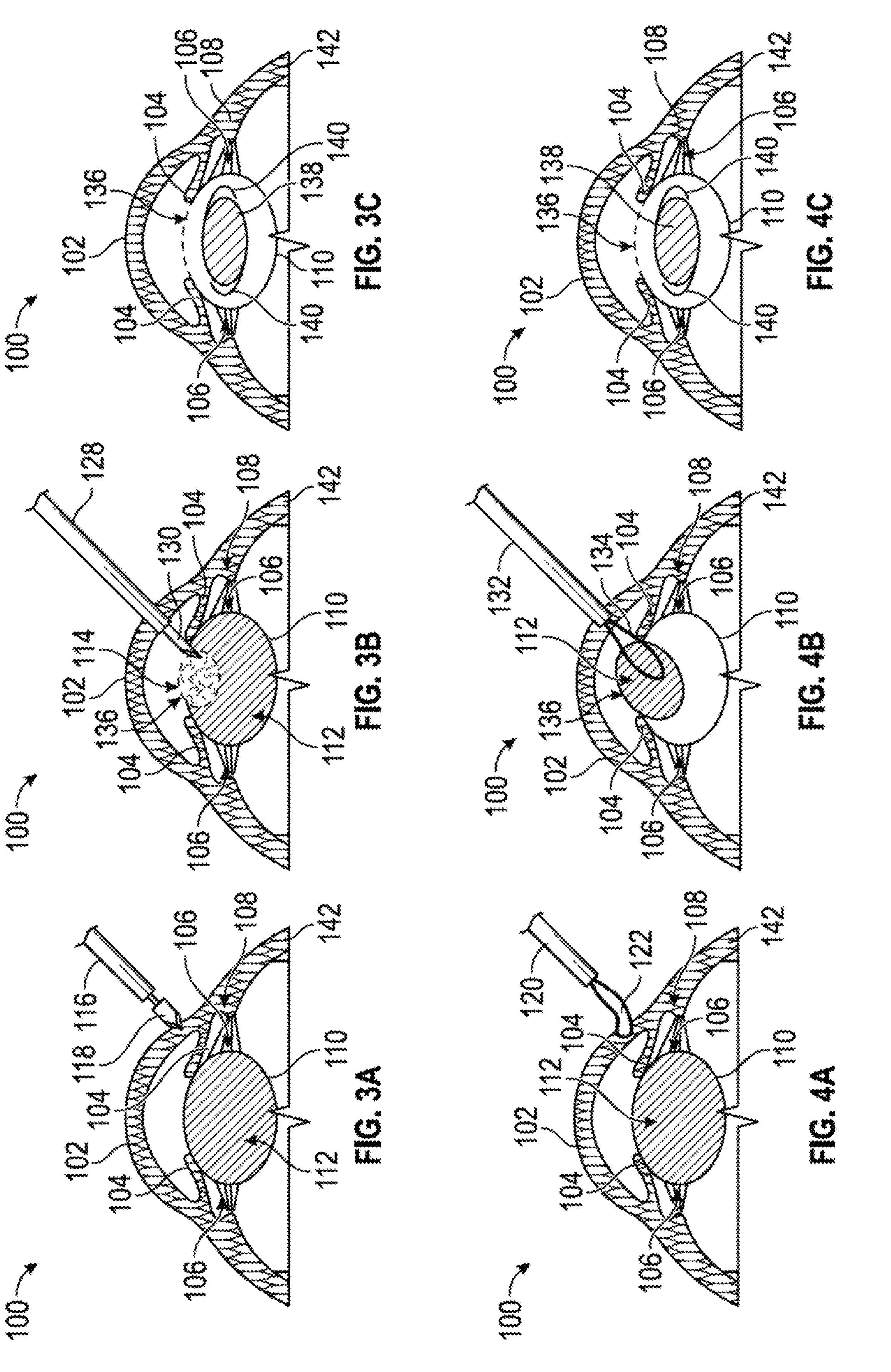
FIGS. 3A-3C illustrate a method of performing a cataract surgery.
FIGS. 4A-4C illustrate a method of performing a cataract surgery.

FIGS. 3A-3C illustrate a method of performing a cataract surgery. As illustrated in FIG. 3A, the eye 100 includes a capsular bag 110 with a crystalline lens 112 posterior to the iris 104. The capsular bag 110 is attached to the ciliary muscle 108 of the eye 100 by way of the zonules 106.

As described herein, proteins, such as crystallins, and/or biopolymers may clump together to cloud the lens 112, resulting in a cataract that impairs vision. A cataract surgery may be performed to improve vision. To perform a cataract surgery, an incision may be cut in the cornea 102 (e.g., corneal margin) and/or sclera 142 to access an interior of the eye. For example, a diamond knife tool 116 having a diamond knife 118 may be used to cut a small incision in the cornea 102 and/or sclera 142.

As illustrated in FIG. 3B, a phacoemulsification needle tool 128 may be advanced to position a tip 130 through the incision in the cornea 102 and/or sclera 142. The phacoemulsification needle tool 128 may apply ultrasound energy to the capsular bag 110 and/or cut through the capsular bag 110 with a cutting edge to create an opening 136 (e.g., anterior opening) in the capsular bag 110 to access the lens 112. The phacoemulsification needle tool 128 may apply ultrasound energy by way of the tip 130 to the lens 112 to emulsify the lens 112. The emulsified portion 114 of the lens 112 may be aspirated (e.g., vacuumed) out of the capsular bag 110 of the eye 100.

With the lens 112 removed, as shown in FIG. 3C, an intraocular lens (IOL) 138 may be inserted through the incision in the cornea 102 and/or sclera 142 and through the opening 136 to position the intraocular lens 138 in the capsular bag 110. The intraocular lens 138 may include haptics 140 that contact the capsular bag 110, which may include contacting an equatorial region of the capsular bag 110. With the lens 112 removed and the intraocular lens 138 positioned in its place, the vision of the eye 100 may be improved. The intraocular lens 138 may be monofocal or accommodating. The intraocular lens 138 may include toric features to address an astigmatism.

FIGS. 4A-4C illustrate a method of performing a cataract surgery. As illustrated in FIG. 4A, a crescent knife tool 120 having a crescent knife 122 may be used to cut an incision in the cornea 102 (e.g., corneal margin) and/or sclera 142. The incision from the crescent knife tool 120 may be larger compared to the incision by the diamond knife tool 116 described in reference to FIGS. 3A-3C. As illustrated in FIG. 4B, a lens expression loop tool 132 may be advanced to position a loop 134 through the incision in the cornea 102 and/or sclera 142. The lens expression loop tool 132 may create (e.g., cut) an opening 136 in the capsular bag 110 to access the lens 112. The loop 134 may cut (e.g., fragment) and/or capture the lens 112. The loop 134 may capture the lens 112 and be retracted back through the opening 136 and incision to remove the lens 112. With the lens 112 removed, the intraocular lens 138 may be inserted through the incision in the cornea 102 and/or sclera 142 and through the opening 136 to position the intraocular lens 138 in the capsular bag 110. With the lens 112 removed and the intraocular lens 138 positioned in its place, the vision of the eye 100 may be improved.

Figure 5C:
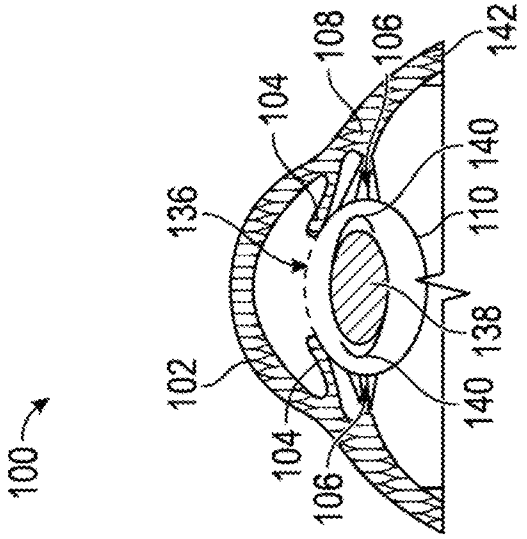
FIGS. 5A-5C illustrate a method of performing a cataract surgery.
Figure 5B:
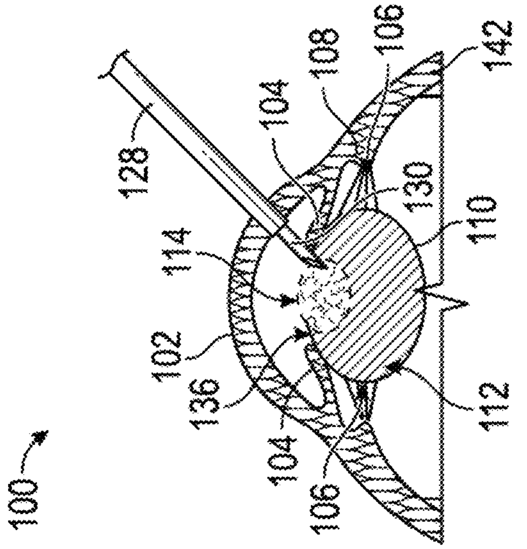
Figure 5A:
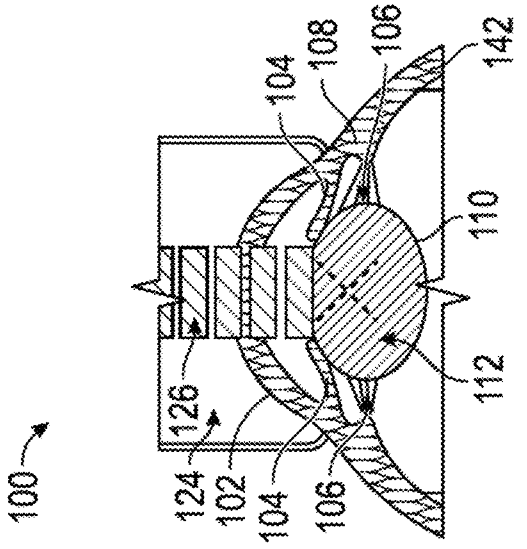

FIGS. 5A-5C illustrate a method of performing a cataract surgery. As illustrated in FIG. 5A, a laser tool 124 may use a laser 126 (e.g., femtosecond laser) to make an incision in the cornea 102 and/or sclera 142. The laser tool 124 may use the laser 126 to perform initial fragmentation of the lens 112 and/or form the opening 136 in the capsular bag 110. The laser tool 124 may include a fixating tool. The tip 130 of a phacoemulsification needle tool 128 may be inserted through an incision in the cornea 102 and/or sclera 142 to apply ultrasound energy to the lens 112 to emulsify the lens 112. The emulsified portion 114 of the lens 112 may be aspirated out of the capsular bag 110. With the lens 112 removed, the intraocular lens 138 may be inserted through the incision in the cornea 102 and/or sclera 142 and through the opening 136 to position the intraocular lens 138 in the capsular bag 110. With the lens 112 removed and the intraocular lens 138 positioned in its place, the vision of the eye 100 may be improved.

Figure 6A:
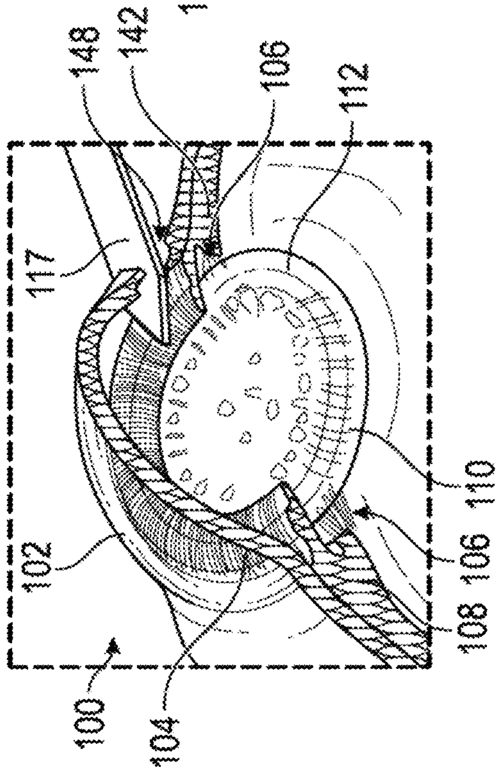
FIGS. 6A-6D illustrate a method of performing a cataract surgery.
Figure 6B:
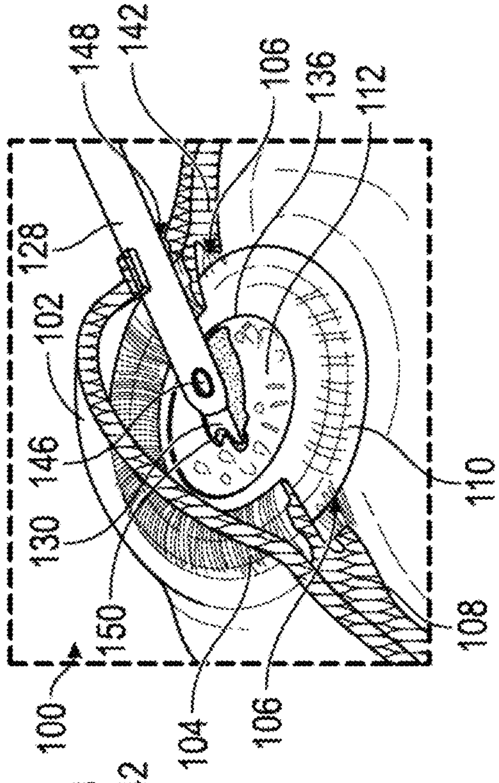
Figure 6C:
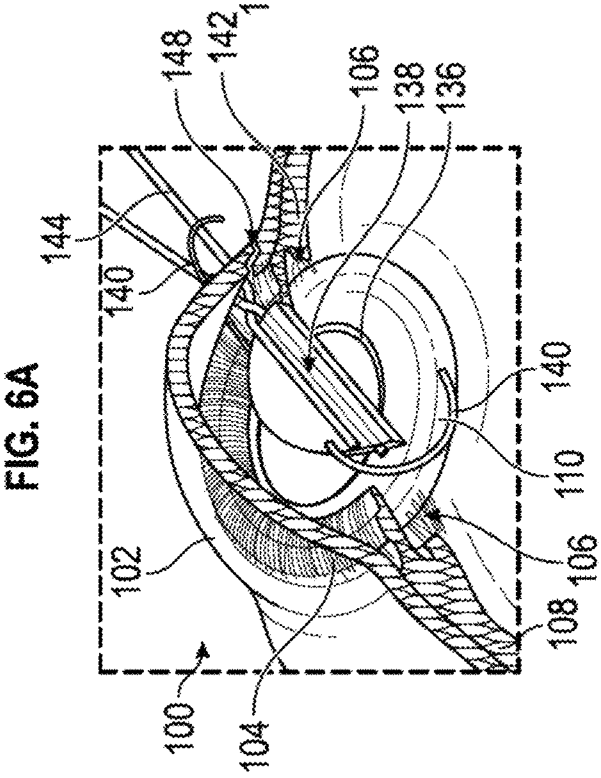
Figure 6D:
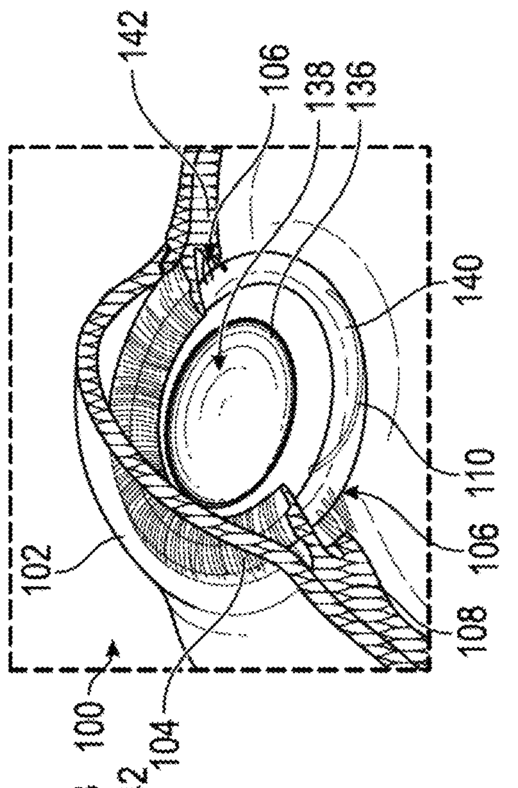

FIGS. 6A-6C illustrate a method of performing a cataract surgery. As illustrated in FIG. 6A, a blade 117 can be used to make (e.g., cut) an incision 148 in the cornea 102 (e.g., corneal margin) and/or sclera 142. As illustrated in FIG. 6B, a phacoemulsification needle tool 128 may be inserted through the incision 148 such that ultrasound energy can be applied to the clouded lens 112 by way of the tip 130. Ultrasound energy may be applied to an anterior portion of the capsular bag 110 to form an opening 136. The ultrasound energy applied to the lens 112 may emulsify the lens 112. The phacoemulsification needle tool 128 may include features to aspirate the emulsified lens 112 from the capsular bag 110. For example, the tip 130 may include an opening 150 through which emulsified lens 112 may be aspirated (e.g., vacuumed). The phacoemulsification needle tool 128 may include an irrigation port 146 through which fluid (e.g., saline solution) may flow into the eye 100 to maintain the anterior chamber of the eye 100. With the lens 112 having the cataract removed, an intraocular lens 138 may be disposed through the incision 148 in the cornea 102 and/or sclera 142, as illustrated in FIG. 6C, and through the opening 136 in the capsular bag 110 to position the intraocular lens 138 within the capsular bag 110 as shown in FIG. 6D. With the lens 112 removed and the intraocular lens 138 positioned in its place, the vision of the eye 100 may be improved.

Figure 7A:
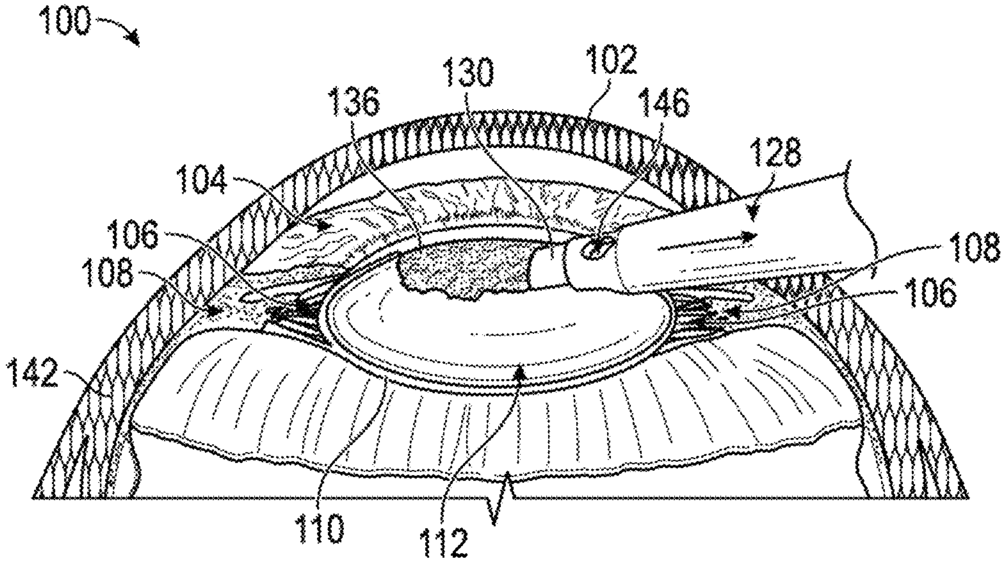
FIGS. 7A and 7B illustrate a method of removing the crystalline lens with a cataract.

FIG. 7A illustrates a phacoemulsification needle tool 128 inserted through an incision in the cornea 102 and/or sclera 142 such that the tip 130 is positioned at the lens 112. As described, ultrasound energy may be applied at the tip 130 to emulsify the lens 112. The emulsified lens 112 may be aspirated through an opening in the tip 130. A fluid (e.g. balanced saline solution) may flow out of the irrigation port 146 of the phacoemulsification needle tool 128 to maintain the anterior chamber of the eye 100.

Figure 7B:
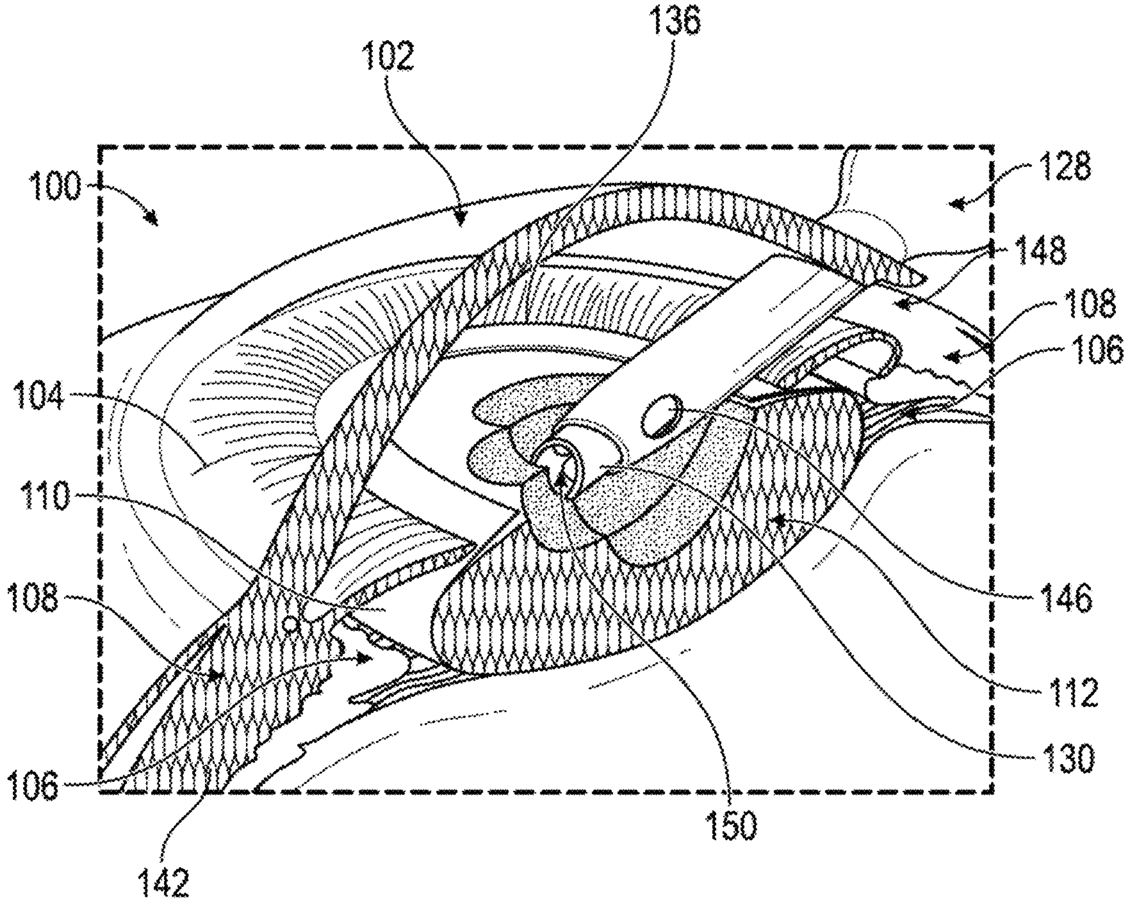

FIG. 7B illustrates a phacoemulsification needle tool 128 inserted through an incision 148 in the cornea 102 and/or sclera 142 such that the tip 130 is positioned through an opening 136 of the capsular bag 110 to be disposed at the lens 112. As described, ultrasound energy may be applied at the tip 130 to emulsify the lens 112. The emulsified lens 112 may be aspirated through an opening 150 in the tip 130. A fluid (e.g., saline solution) may flow out of the irrigation port 146 of the phacoemulsification needle tool 128 to maintain the anterior chamber of the eye 100.

Temperature Ranges

As described herein, crystallins are the predominant structural proteins in the crystalline lens 112, which may at least include alpha-crystallins, and betagamma-crystallins. The lens 112 may flow at a glass transition temperature. The proteins and/or biopolymers of the lens 112 may flow at a glass transition temperature. The lens 112 may melt at a melting temperature. The proteins and/or biopolymers of the lens 112 may melt at a melting temperature, which is higher than the glass transition temperature. The thermal systems (e.g., thermal emulsification systems) described herein may apply heat to raise the temperature of the lens 112 (e.g., one or more proteins, biopolymers, and/or other components of the lens 112) to the glass transition temperature, resulting in softening of the lens 112 (e.g., one or more proteins, biopolymers, and/or other components of the lens 112), and/or to the melting temperature, resulting in the melting (e.g., emulsification, liquification) of the lens 112 (e.g., one or more proteins, biopolymers, and/or other components of the lens 112). In some variants, the thermal systems described herein may apply a heat that raises the temperature of the lens 112 between the glass transition temperature and/or melting temperature. As described herein, one or more elements (e.g., contacts, heating elements, wires, loops, meshes, baskets, tips, etc.) and/or fluid (e.g., saline solution) can be heated to at least the glass transition temperature of the lens 112 (e.g., proteins, biopolymers, and/or other components of the lens 112), melting temperature of lens 112 (e.g., one or more proteins, biopolymers, and/or other components of the lens 112), and/or between the glass transition temperature and/or melting temperature of the lens 112. The fluid can be any that is suitable for ocular procedures (e.g., saline, balanced salt solution, 0.9% saline, pharmaceutical drops, viscoelastic, etc.). Heating the lens 112 to a glass transition temperature and/or melting temperature of the lens 112 (e.g., proteins, biopolymers, and/or other components of the lens 112) may ease removal (e.g., aspiration) of the lens 112 from the capsular bag 110. The one or more elements and/or fluid can provide localized heat (e.g., ultra-localized heat) to the lens 112, which may avoid damaging other portions of the eye 100.

Figure 8A:
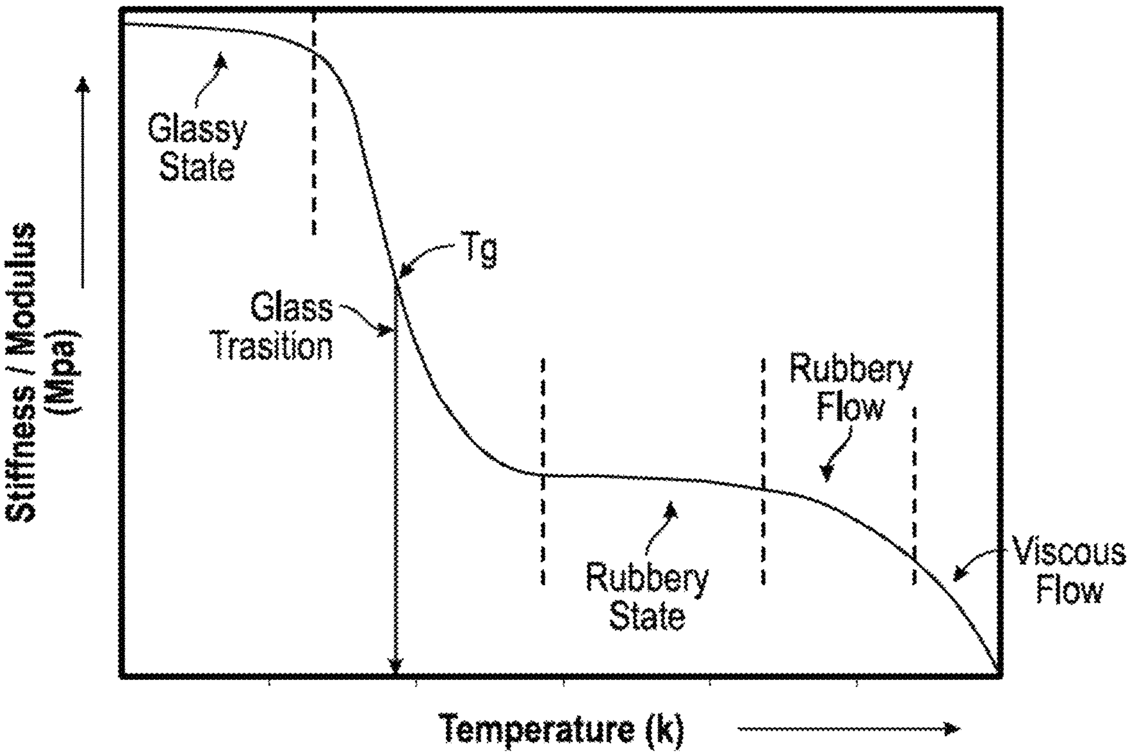
FIGS. 8A and 8B illustrate graphs showing the glass transition temperature of the crystalline lens.
Figure 8B:
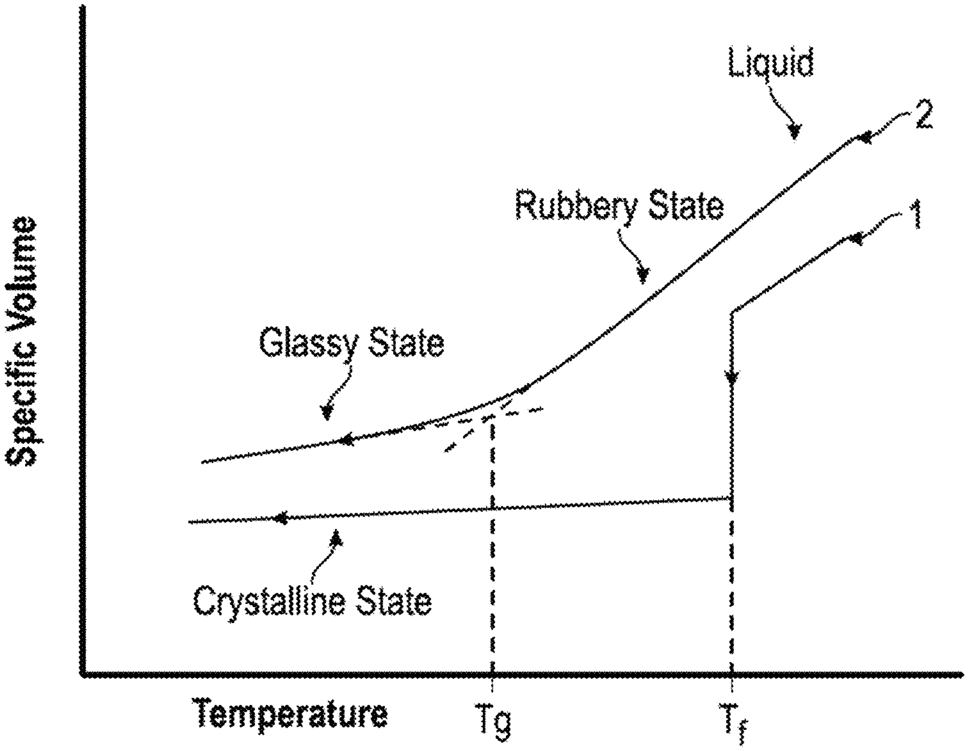

FIG. 8A illustrates an example graph representing the stiffness/modulus (MPa) against temperature (k) of the lens 112 (e.g., proteins, biopolymers, and/or other components of the lens 112). As shown, at a glass transition temperature (Tg), the lens 112 (e.g., proteins, biopolymers, and/or other components of the lens 112) may reach a glass transition. FIG. 8B illustrates an example graph representing the specific volume of the lens 112 (e.g., proteins, biopolymers, and/or other components of the lens 112) against temperature. Once again, at a glass transition temperature (Tg), the lens 112 (e.g., proteins, biopolymers, and/or other components of the lens 112) may reach a glass transition. When heated to the glass transition temperature, the lens 112 (e.g., proteins, biopolymers, and/or other components of the lens 112) may change from a first state (e.g., hard state, glass state) to a second state softer than the first state wherein the lens 112 (e.g., proteins, biopolymers, and/or other components of the lens 112) start to flow. When heated to the glass transition temperature, the lens 112 (e.g., proteins, biopolymers, and/or other components of the lens 112) may decrease in viscosity.

The lens 112 (e.g., proteins, biopolymers, and/or other components of the lens 112) may be emulsified, which may be described as liquified, at a temperature above the glass transition temperature (e.g., melting temperature). When the lens 112 (e.g., proteins, biopolymers, and/or other components) has been emulsified, the lens 112 may be removed more efficiently from the eye (e.g., from the capsular bag). For example, the lens 112 can be removed with emulsification and aspiration much quicker compared to previous methods, which can include emulsification and aspiration of the lens within seconds, less than one minute, or less than two minutes. Additionally, the liquified lens can be aspirated with less invasive techniques (e.g., a fine gauge needle, which can at least include the following gauges: 16, 18, 19, 20, 21, 22, 23, 25, 26, 27, 29, 30, and others) compared to prior techniques. The lens 112 can be emulsified from exposure to a heated element (e.g., wire, tip, etc.). The lens 112 can be emulsified from exposure to a heated fluid (e.g., saline solution).

Figure 9A:
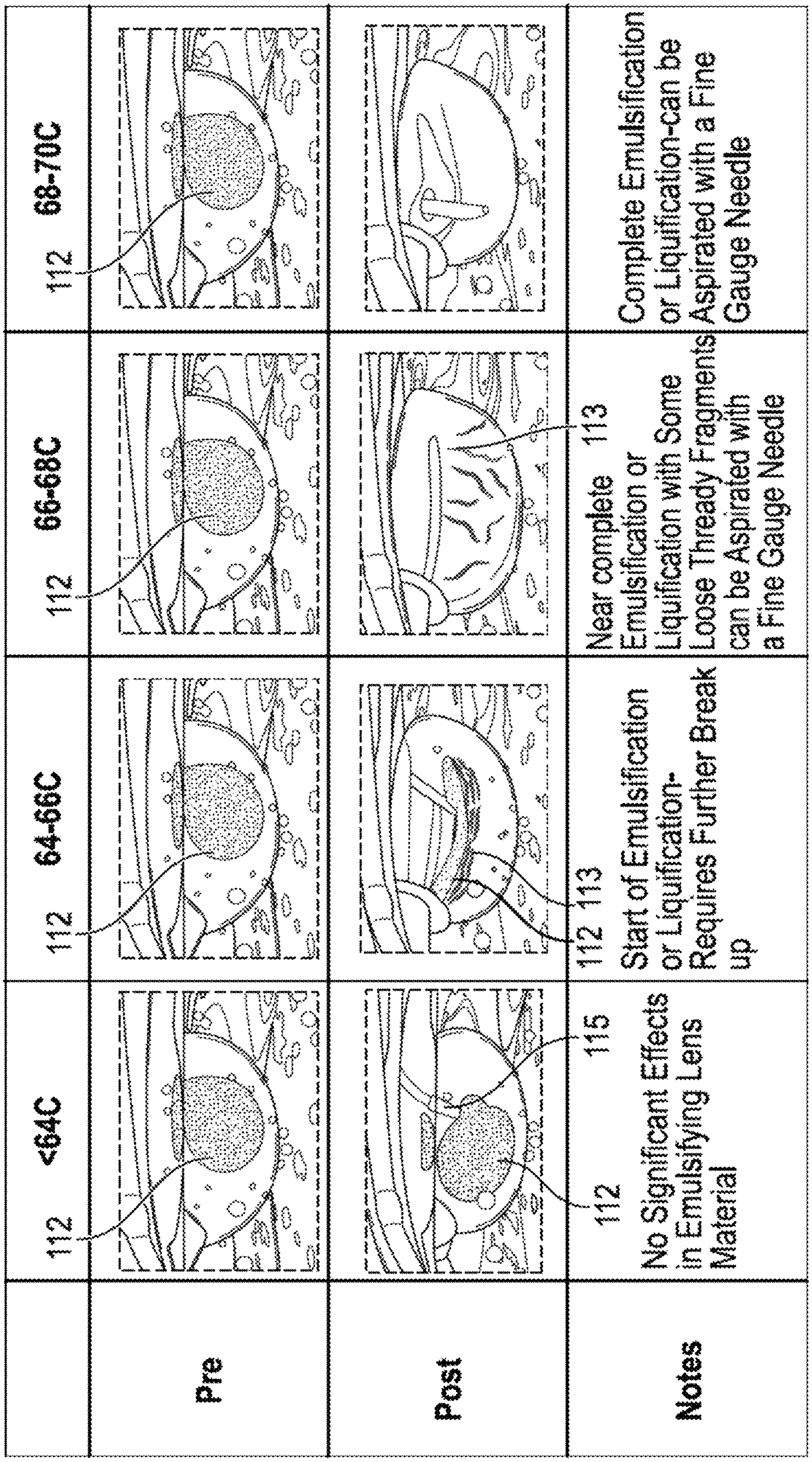
FIG. 9A illustrates a table of crystalline lenses with cataracts before and after applying a heated fluid at different temperatures.

Through experimentation, the different effects on the lens from exposure to a heat source at different temperature ranges has been discovered. For example, FIG. 9A illustrates a table of the results of exposing human lenses 112 with cataracts to a heated fluid (e.g., saline solution) at different temperature ranges. As shown, when a lens 112 was exposed to a fluid at less than 64 degrees Celsius for eight to ten minutes, no significant emulsification of the lens 112 was observed but softening of the lens can occur.

When a lens 112 was exposed to a fluid at 64-66 degrees Celsius for less than five minutes, the lens 112 began to emulsify. Additional mechanical support (e.g., mechanical agitation with one or more surgical tools) was employed to break up remaining fragments 113 of the lens 112.

When a lens 112 was exposed to a fluid at 66-68 degrees Celsius for one to three minutes, the lens almost entirely emulsified with some loose thready fragments 113 still present, which can be aspirated with a fine gauge needle (e.g., 18-22 gauge needles). Some additional minor mechanical support (e.g., mechanical agitation with one or more surgical tools) was employed to assist in breaking up the fragments of the lens.

When a lens 112 was exposed to a fluid at 68-70 Celsius for less than one minute, the lens was emulsified (e.g., entirely emulsified), which can be aspirated with a fine gauge needle (e.g., 30 gauge) needle. No mechanical support was employed to assist in breaking up the lens.

Temperatures above 70 degrees Celsius needlessly expose the eye to more energy than needed to emulsify the lens. During testing, localized phase changes to a gaseous state were observed when exposing the lens to a fluid at temperatures above 70 degrees Celsius to 80 degrees Celsius. Above 80 degrees Celsius, rapid phase change to a gaseous state was observed instead of emulsification. The phase change to the gaseous state was observed to damage (e.g., burn) surrounding structures of the eye (e.g., capsular bag, zonules, etc.).

Figure 9B:
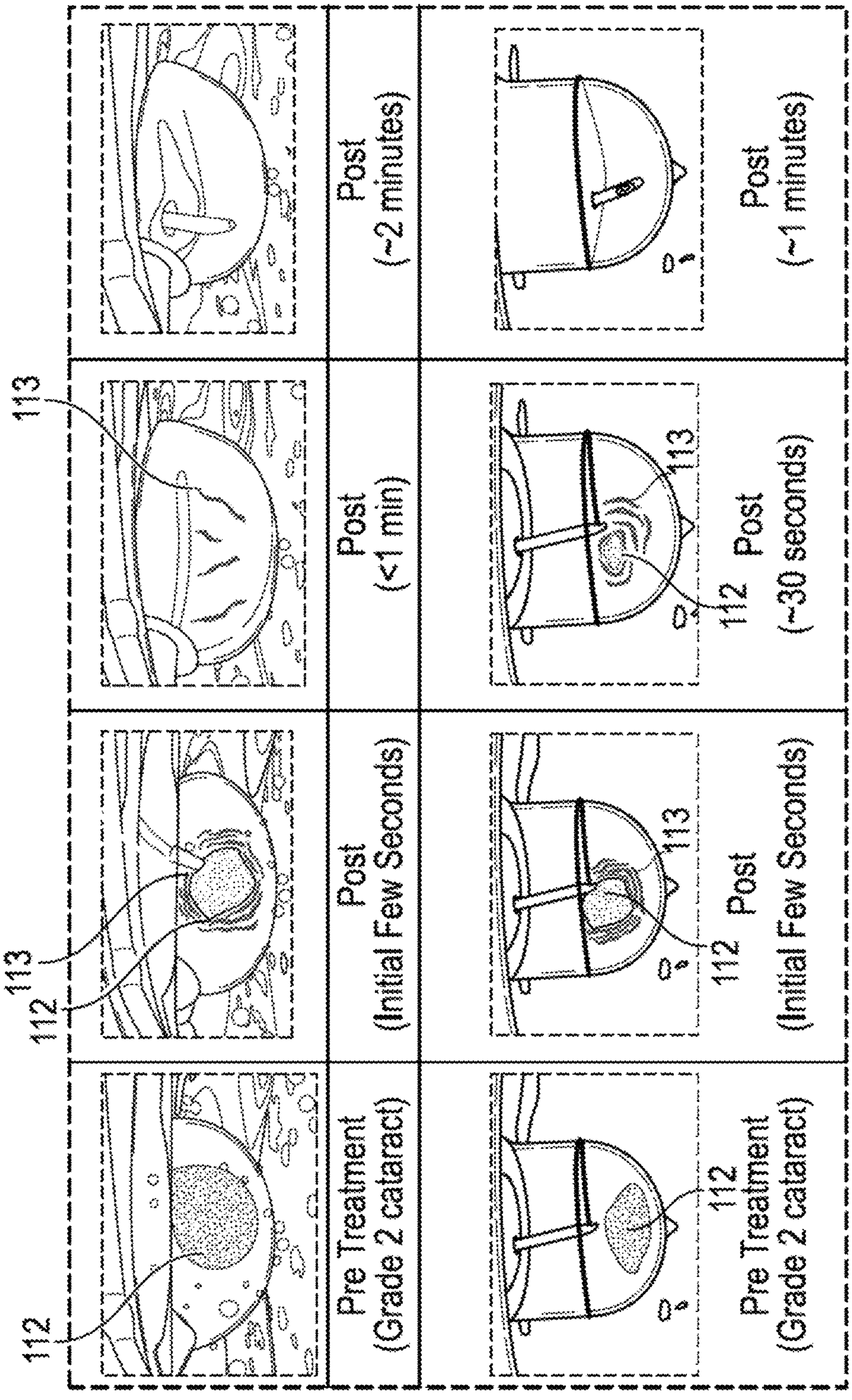
FIG. 9B illustrates a table of crystalline lenses with cataracts before and after applying a heated fluid after different durations of time.

FIG. 9B illustrates a table of the results of exposing human lenses 112 with cataracts to a heated fluid (e.g. saline solution) at 68-70 degrees Celsius. As shown, the lenses 112 were observed to begin to emulsify after a few initial seconds, which included some fragments 113 separating out. After about thirty seconds, significant emulsification of the lens 112 was observed with much of the lens 112 reduced to loose fragments 113. Approaching one minute, almost the complete emulsification of the lens 112 was observed with a few loose fragments 113 remaining. At about one minute, the complete emulsification of the lens 112 was observed. At about two minutes, the complete emulsification of the lens 112 was observed.

Figure 9C:
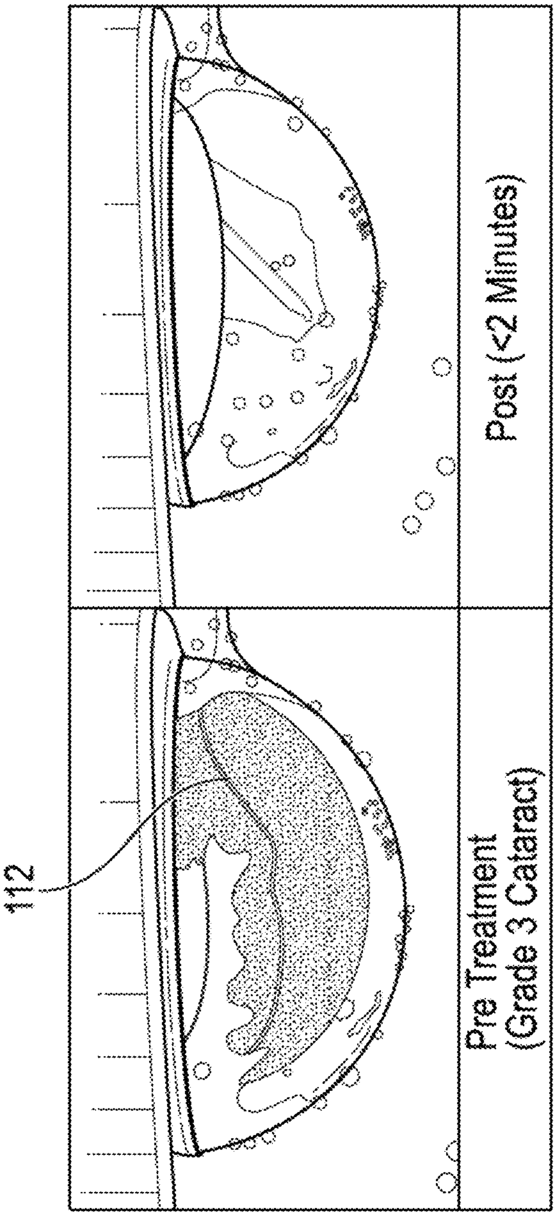
FIG. 9C illustrates a table showing a crystalline lens with a cataract before and after applying a heated fluid.

FIG. 9C illustrates a table of the results of exposing a human lens 112 with a cataract to a heated fluid (e.g., saline solution) at 68-70 degrees Celsius. As shown, in less than two minutes, the complete emulsification of the lens 112 was observed.

Figures 2, 9D:
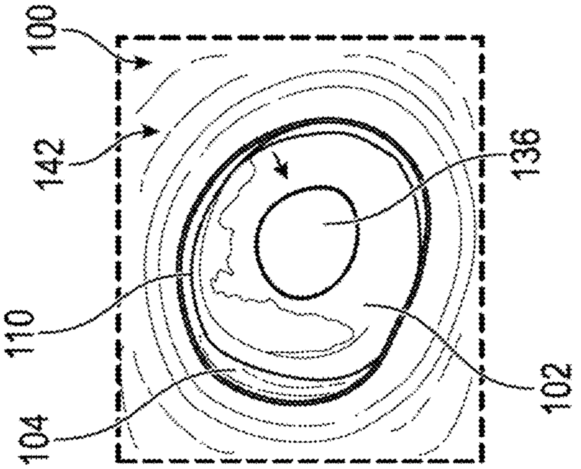
FIG. 9D-1 illustrates a crystalline lens with a cataract disposed in a capsular bag.
Figures 1, 9D:
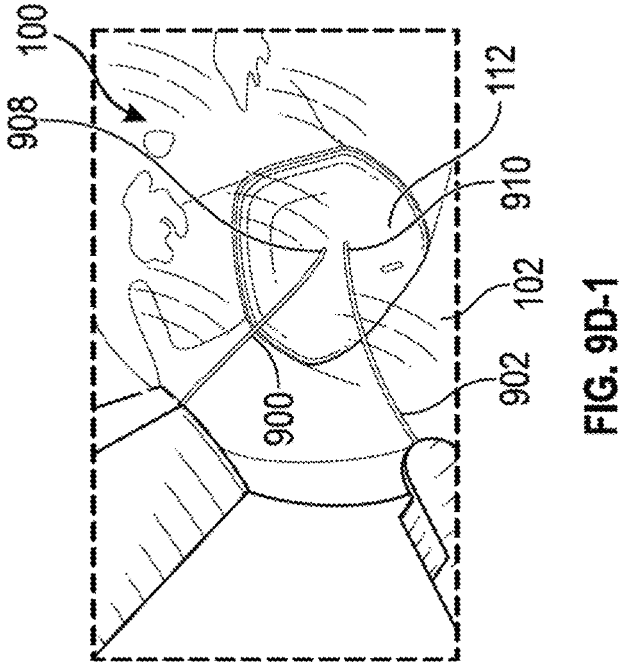

FIGS. 9D-1 and 9D-2 illustrate an ex-vivo surgery simulation that was performed on a cadaver eye 100 in which the lens 112 was emulsified by heated fluid at 68-70 degrees Celsius and removed by aspiration in less than two minutes. FIG. 9D-1 illustrates the lens 112 with cataracts disposed in the eye 100 with an irrigation tube 900 (e.g., irrigation device, irrigation tip, irrigation cannula) and aspiration tube 902 (e.g., aspiration device, aspiration tip, aspiration cannula) positioned to emulsify and aspirate the lens 112. The irrigation tube 900 is disposed in the eye 100 through the cornea 102 to position an outlet 908 of the irrigation tube 900 at the lens 112. The aspiration tube 902 is disposed in the eye 100 through the cornea 102 to position an inlet 910 of the aspiration tube 902 at the lens 112. Heated fluid at 68-70 degrees Celsius was directed at the lens 112 through the outlet 908 of the irrigation tube 900 to emulsify the lens 112. The heated fluid and emulsified lens 112 were aspirated from the capsular bag 110 through the inlet 910 of the aspiration tube 902. The inlet 910 of the aspiration tube 902 was positioned proximate the outlet 908 of the irrigation tube 900 to quickly aspirate the heated fluid and emulsified lens 112 to help localize the heat from the heated fluid flowing out of the irrigation tube 900.

FIG. 9D-2 illustrates the eye 100 after the lens 112 was emulsified by the heated fluid flowing out of the irrigation tube 900 at 68-70 degrees Celsius and aspirated out by the aspiration tube 902. As illustrated, the capsular bag 110 remained intact after removal of the lens 112. As illustrated, the opening 136 (e.g., Capsulorhexis) in the capsular bag 110 through which the irrigation tube 900 and aspiration tube 902 accessed the lens 112 remained intact after removal of the lens 112. Maintaining the integrity of the capsular bag 110 can be beneficial for numerous reasons such as IOL implantation and/or function. As described herein, maintaining the integrity of the capsular bag 110 can be beneficial for fill-the-bag style IOLs in which a gel and/or fluid is inserted into the capsular bag 110 as an artificial lens to replace the lens 112.

Identifying the impact of different temperature ranges on the lens was a critical discovery for successful implementation of the systems and methods described herein. As detailed herein, the lens 112 entirely emulsifies when exposed for less than one minute or two minutes to a fluid heated to 68-70 degrees Celsius. Accordingly, flowing a fluid above 70 degrees Celsius into the eye can completely emulsify the lens but needlessly exposes the eye to more energy than required to efficiently emulsify the lens. As detailed above, phase changes to a gaseous state were observed above 70 degrees Celsius, and the phase changes to the gaseous state were observed to damage (e.g., burn) surrounding structures of the eye (e.g., capsular bag, zonules, etc.). As such, the fluid introduced into the eye should not exceed 70 degrees Celsius. As detailed herein, the lens almost entirely emulsifies when exposed to a fluid at 66-68 degrees Celsius but some fragments (e.g., loose thready fragments) of lens remain intact that are small enough to be aspirated through a fine gauge needle. Accordingly, introducing a fluid at 66-70 degrees Celsius is the newly discovered preferred range for emulsifying the lens of the eye. That said, if complete emulsification of the lens is desired in a shortened duration of time (e.g., less than one minute, less than two minutes), then introducing a fluid at 68-70 degrees Celsius is preferred. Nevertheless, introducing a fluid at 64-66 degrees Celsius is also effective because the lens starts to emulsify at that temperature range, but at that temperature range, an aspiration device with a larger opening is needed to aspirate the larger fragments compared to the aspiration device used when using a fluid at 66-70 degrees Celsius or even 68-70 degrees Celsius. However, the 66-70 degrees Celsius and/or 68-70 degrees Celsius temperature ranges may be preferred to reduce the total quantity of energy (e.g., Joules) imparted to the eye compared to lower temperature ranges such as 64-66 degrees Celsius. For example, exposing the lens to fluid at 64-66 degrees Celsius (e.g., heated element and/or heated fluid) for five minutes can impart more total energy to the eye compared to 68-70 degrees Celsius for less than one minute, and it can be desirable to expose the eye to less total energy. Utilizing a fluid at less than 64 degrees Celsius resulted no significant observable emulsification of the lens 112. Accordingly, introducing a fluid at 64-70 degrees is the newly discovered workable range for emulsification of the lens. However, a temperature below 64 degrees Celsius can be employed if softening of the lens is desired as opposed to liquification.

The systems and methods described herein can employ different temperatures when emulsifying different portions of the lens. For example, the nucleus/cortex of the lens is denser than the peripheral portions of the lens. Accordingly, a higher temperature (e.g., closer to or at 70 degrees Celsius) may be employed when liquifying the nucleus/cortex compared to the peripheral portions of the lens. In some variants, the systems described herein can automatically adjust the temperature as the heating element and/or irrigation cannula (e.g., tip) is navigated around the lens 112 to compensate for changing densities. In some variants, the surgeon can adjust the temperature as the heating element and/or irrigation cannula is navigated around the lens to compensate for changing densities.

In some variants, using heated fluid to emulsify the lens may be preferred to a heated element. The heated fluid may have less heat loss challenges compared to the heated element because of the inflow of newly heated fluid and rapid aspiration. The heated fluid may provide a larger contact area compared to the heated element.

Systems and Methods with Tip Having One or More Temperature Controlled Elements

Figure 10:
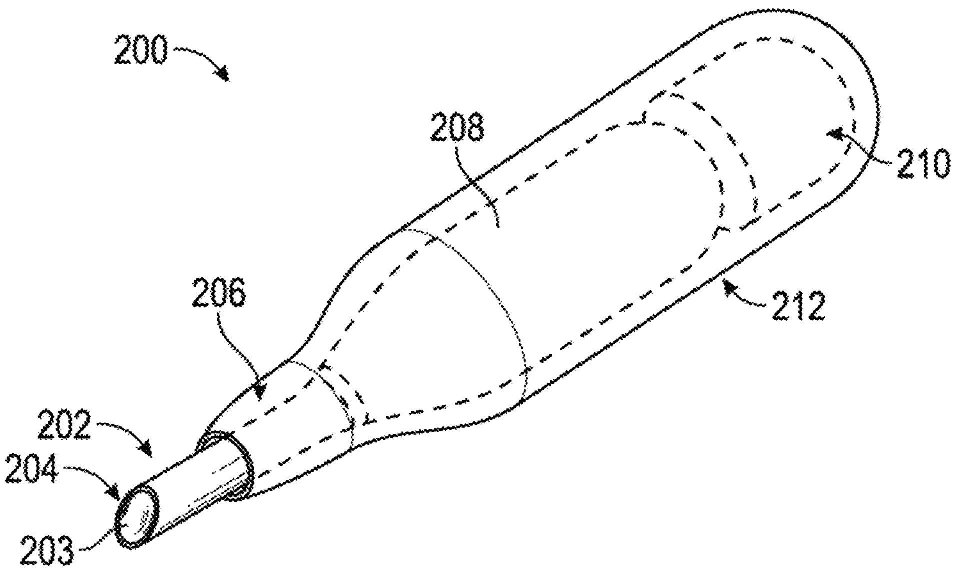
FIG. 10 illustrates a thermal system.

Alternative to or in addition with utilizing a heated fluid to emulsify or soften the lens, systems and methods are described herein that include a tip having one or more temperature controlled elements that can apply localized heat to the lens. For example, FIG. 10 illustrates a thermal system 200 (e.g., thermal emulsification system, thermal device, thermal emulsification device). The thermal system 200 may be used to soften and/or emulsify the lens 112 (e.g., proteins, biopolymers, and/or other components of the lens 112) of the eye 100. The thermal system 200 may be used to aspirate the softened and/or emulsify lens 112 (e.g., proteins, biopolymers, and/or other components of the lens 112). The thermal system 200 may irrigate the eye 100 to maintain the anterior chamber. The thermal system 200 may be a portable, handheld device. In some variants, the heat features of the thermal system 200 may be incorporated with an existing aspiration and/or irrigation device.

The thermal system 200 can include a tip 202 (e.g., distal tip, distal end, end, tube). A temperature of the tip 202 of the thermal system 200 may be controlled, which can include raising (e.g., heating) and/or lowering (e.g., cooling) the temperature of the tip 202. The tip 202 may include one or more temperature controlled elements 204 (e.g., localized heating zones) that may be heated and/or cooled. The one or more temperature controlled elements 204 may be positioned at a distal face (e.g., leading plane) of the tip 202, which may be angled. The one or more temperature controlled elements 204 may include various configurations, which may at least include a ring shape, discrete circumferentially positioned elements, and/or other configurations. The one or more temperature controlled elements 204 may be heated either directly or indirectly with various energy sources, which may at least include heat, radio frequency, laser, electricity (e.g., current), resistive heating, inductive heating, etc. The temperature controlled element 204 may include a metal such as a metal alloy (e.g., a nickel and titanium alloy) to transfer heat to the lens 112. The temperature controlled element 204 can enable the thermal system 200 to apply heat in a localized and targeted manner to the lens 112 that avoids damage to other features of the eye 100. The tip 202 include a circular periphery. The tip 202 can include peripheries of various shapes, which can at least include oval, polygonal (e.g., triangle, square, pentagon, etc.), irregular, and/or others. The tip 202 may be a tube.

The thermal system 200 may include hardware 210 that can enable the thermal system 200 to perform the methods described herein. The hardware 210 can include a power source (e.g., battery, rechargeable battery, disposable battery), power source interface (e.g., interface for connecting to a wired power source), temperature control unit, aspiration control unit, irrigation control unit, controller, processor, wireless communication interface, wired communication interface, memory, etc. The hardware 210 may be disposed at a proximal end of the thermal system 200. The hardware 210 may be distributed along the length of the thermal system 200. The thermal system 200 may include a housing 212 to house the hardware 210 and/or other components of the thermal system 200. The housing 212 may include an insulating material to protect the patient from heat. In some variants, the housing 212 may include a neck portion 206 proximate the tip 202 that includes insulation properties that may protect the patient from heat.

The temperature control unit may control temperature generation and/or modulation. The control unit may control the amount of energy directed to the temperature controlled element 204 to adjust the temperature of the temperature controlled element 204, which may include adjusting energy provided by the power source and/or by way of the power source interface to the temperature controlled element 204. The temperature control unit may maintain the one or more temperature controlled elements 204 at a temperature, raise the temperature, lower the temperature, cycle the temperature, adjust the temperature based on sensor input (e.g., temperature detected at the tip 202), etc.

The aspiration control unit may control aspiration. For example, the tip 202 may include an opening 203 through which softened and/or emulsified lens 112 (e.g., proteins, biopolymers, and/or other components of the lens 112) may be aspirated (e.g., vacuumed). The aspiration control unit may initiate and cease aspiration through the opening 203. In some variants, the temperature controlled element 204 may be disposed around the opening 203, which can include circumferentially distributed around the opening 203.

The irrigation control unit may control irrigation. The thermal system 200 may include a port through which fluid (e.g., saline solution) can flow into the eye 100. The fluid may maintain the anterior chamber of the eye 100 while the lens 112 is being removed.

The thermal system 200 may include one or more user interfaces (e.g., button(s), dial(s), switch(es), display(s), touchpad(s), touchscreen(s), knob(s), trigger(s), indicator(s), gauge(s), and/or slider(s)) to enable a user (e.g., surgeon) to control the thermal system 200, which may at least include activation of the thermal system 200, deactivation of the thermal system 200, heating of the one or more temperature controlled elements 204, cooling of the one or more temperature controlled element 204, initiating and/or ceasing aspiration, initiating and/or ceasing irrigation, etc. In some variants, the user may set a temperature for one or more temperature controlled elements 204. In some variants, the user may adjust a vacuum force (e.g., increase, decrease) for aspiration. In some variants, the user may adjust the flow (e.g., increase, decrease) of the fluid for irrigation.

The thermal system 200 may include one or more receptacles 208 (e.g., bag), which may be disposed inside of the housing 212. The one or more receptacles 208 may hold material aspirated from the eye 100. The one or more receptacles 208 may hold fluid (e.g., saline solution) for irrigation. The one or more receptacles 208 may be disposable.

The thermal system 200 may communicate with a computing device by way of wired or wireless communication.

Figure 11:
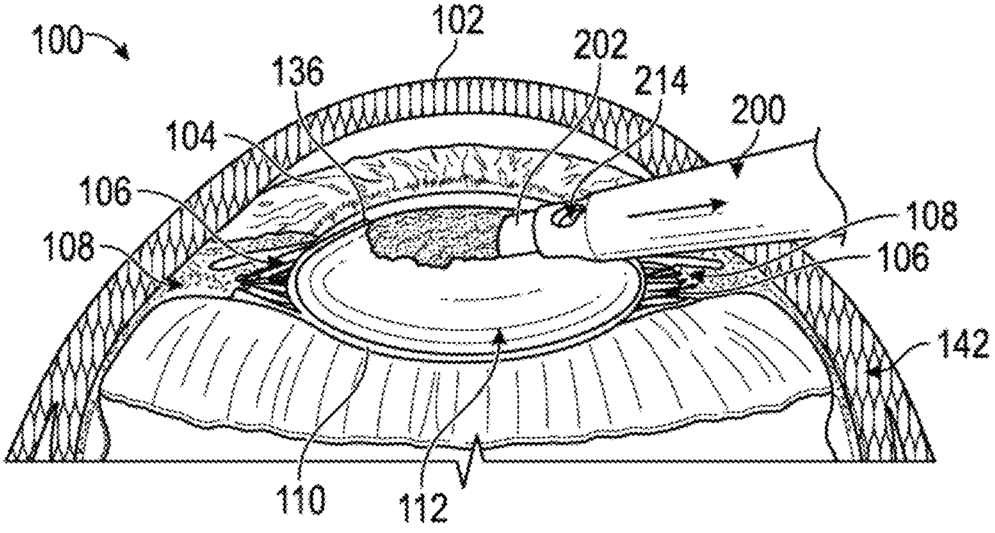
FIG. 11 illustrates the thermal system being used to remove the crystalline lens with a cataract.

FIG. 11 illustrates the thermal system 200 in use. The tip 202 of the thermal system 200 has been advanced through an incision in the cornea 102 and/or sclera 142 to be positioned at the lens 112. The tip 202 (e.g., one or more temperature controlled elements 204) has been heated to soften and/or emulsify the lens 112 (e.g., proteins, biopolymers, and/or other components of the lens 112). The softened and/or emulsified lens 112 is being aspirated through the opening 203 of the tip 202 and into the one or more receptacles 208. The irrigation port 214 is flowing fluid (e.g., saline solution), which may be stored in the one or more receptacles 208, into the eye 100 to maintain the anterior chamber. As described, the heated tip 202 may apply localized and targeted heat to the lens 112 which may avoid damage to other portions of the eye 100. Softening and/or emulsifying of the lens 112 can facilitate quicker aspiration of the lens 112 compared to applying ultrasound, which can improve the safety and efficiency of cataract surgery.

Figure 12:
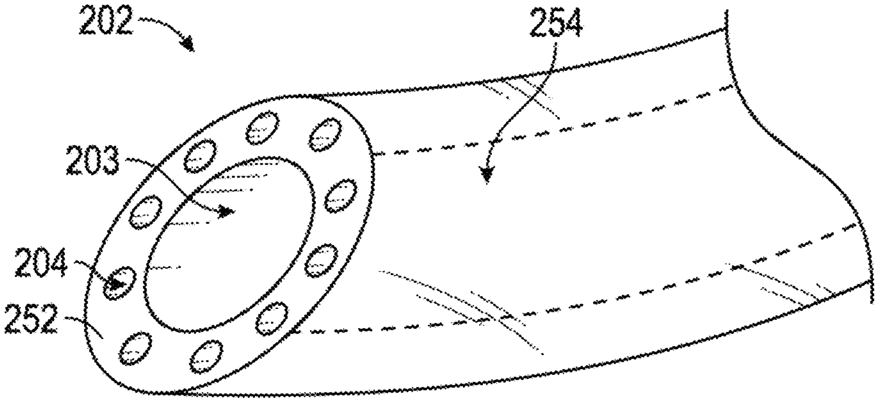
FIG. 12 illustrates a tip of the thermal system with temperature controlled elements.

FIG. 12 illustrates an example tip 202. As described, the temperature of the tip 202 may be controlled. For example, the tip 202 may include one or more temperature controlled elements 204 (e.g., heating elements, contacts, leads, etc.) that may be heated or cooled. The one or more temperature controlled elements 204 may be disposed on a distal end 252 (e.g., distal surface, distal-facing surface, etc.) of the tip 202. The distal end 252 may be angled. The tip 202 can include a plurality of temperature controlled elements 204. The temperature controlled elements 204 can be distributed about the opening 203 of the tip 202. The temperature controlled elements 204 may each have a circular shape but can be others, which can at least include oval, polygonal (e.g., triangle, square, rectangle, pentagon, etc.), irregular, and/or others. The temperature controlled elements 204 may be heated to at least the temperatures described herein to soften and/or emulsify the lens 112 of the eye 100. The softened and/or emulsified lens 112 may be aspirated through the opening 203 and into a channel 254, which can be fluidically connected with a receptacle 208.

Figure 13:
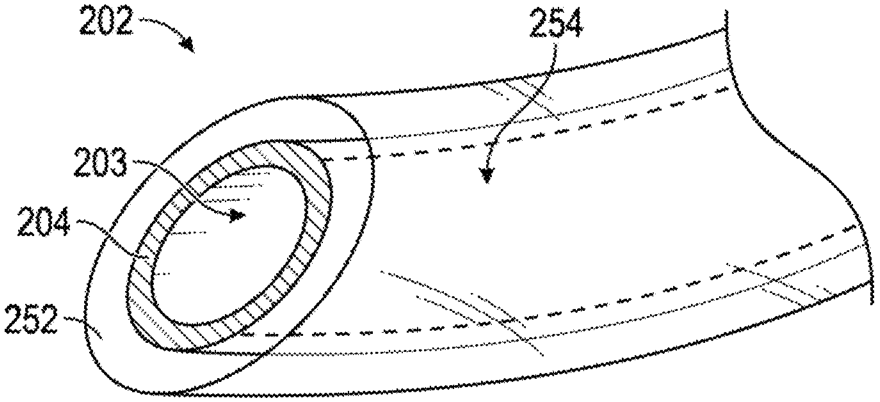
FIG. 13 illustrates a tip of the thermal system with a temperature controlled element.

FIG. 13 illustrates the tip 202. The tip 202 may include a temperature controlled element 204 that has a ring shape, which may be disposed on the distal end 252. The ring shape of the temperature controlled element 204 can be disposed around the opening 203. The temperature controlled element 204 may be disposed at a periphery of the opening 203. The ring shape may have varying thicknesses in the radial direction.

Figure 14A:
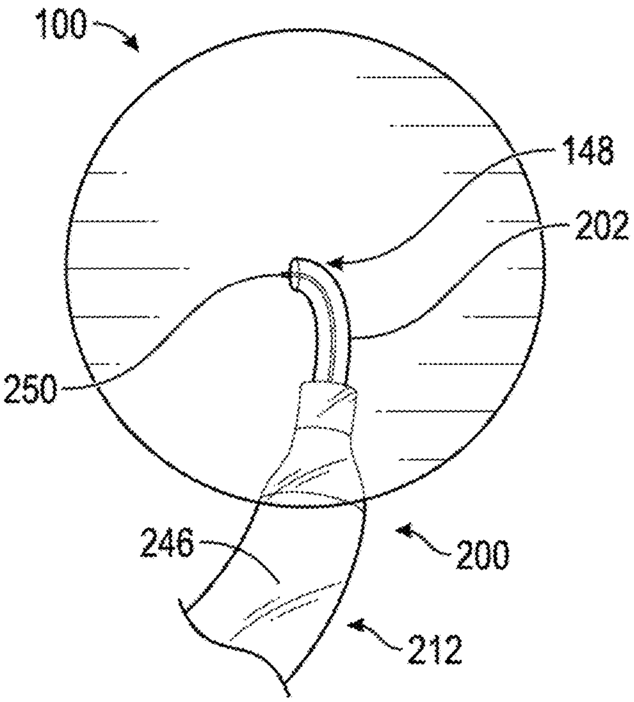
FIGS. 14A-14C illustrate a tip of the thermal system with a retractable temperature controlled element.

FIG. 14A illustrates the tip 202 (e.g., tube, cylinder, conduit). In some variants, the thermal system 200 may include a member 246 (e.g., wire, Nitinol wire, tube). The member 246 may be temperature controlled (e.g., heated, cooled) as described herein. A distal end 250 of the member 246 (e.g., wire) may be deployed from inside the tip 202 to soften and/or emulsify the lens 112 and retracted back within the tip 202. The tip 202 may be insulated to protect the anatomy of the eye 100 not in contact with the member 246 from heat.

Figure 14B:
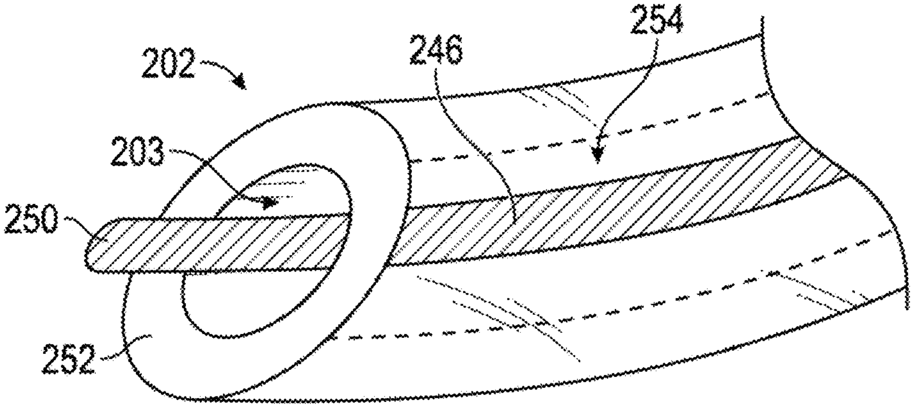
Figure 14C:
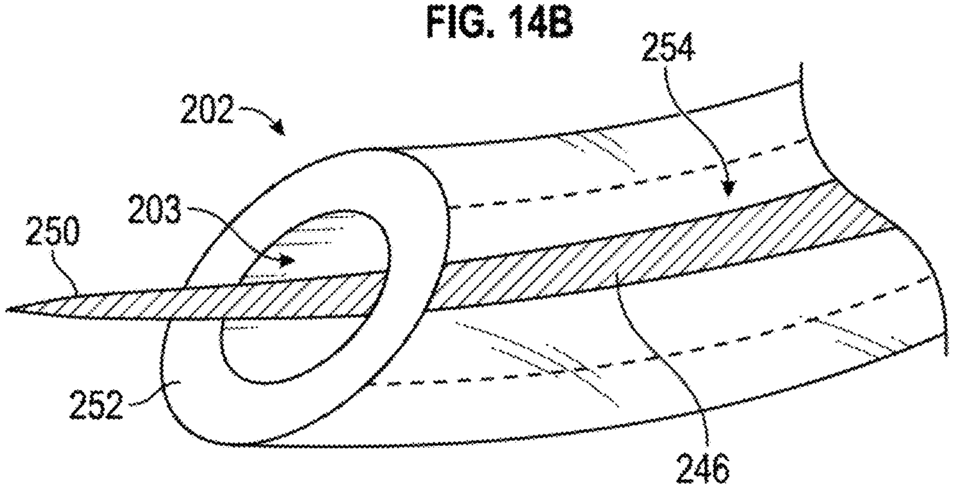

In some variants, the tip 202 may include other heating elements, such as one or more of the temperature controlled elements 204 described herein. In some variants, the tip 202 may not include other heating elements. As illustrated in FIG. 14B, the member 246 may be disposed in the channel 254. When deployed, a distal end 250 of the member 246 may extend through the opening 203 to outside the tip 202. The distal end 250 may apply heat to the lens 112 to soften and/or emulsify the lens 112. The softened and/or emulsified lens 112 may be aspirated through the opening 203 and into the channel 254 of the tip 202. In some variants, the distal end 250 may oscillate (e.g., reciprocate), which may include oscillating in and out of the tip 202, and/or vibrate. As described herein, cryo may be applied by the distal end 250. As described herein, the temperature of the member 246 may be cycled. As illustrated in FIG. 14C, the distal end 250 of the member 246 may be pointed (e.g., sharp, include a cutting edge, etc.).

Figure 15A:
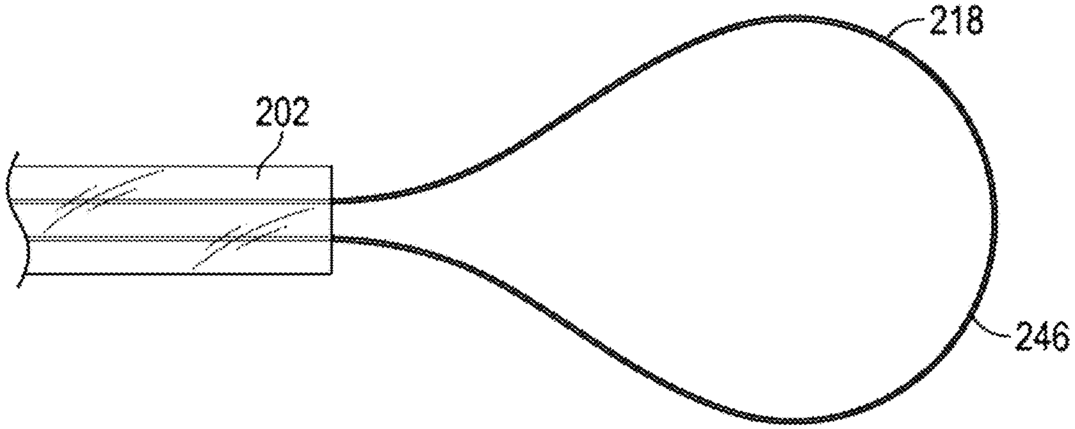
FIGS. 15A and 15B illustrate a temperature controlled loop for the thermal system.
Figure 15B:
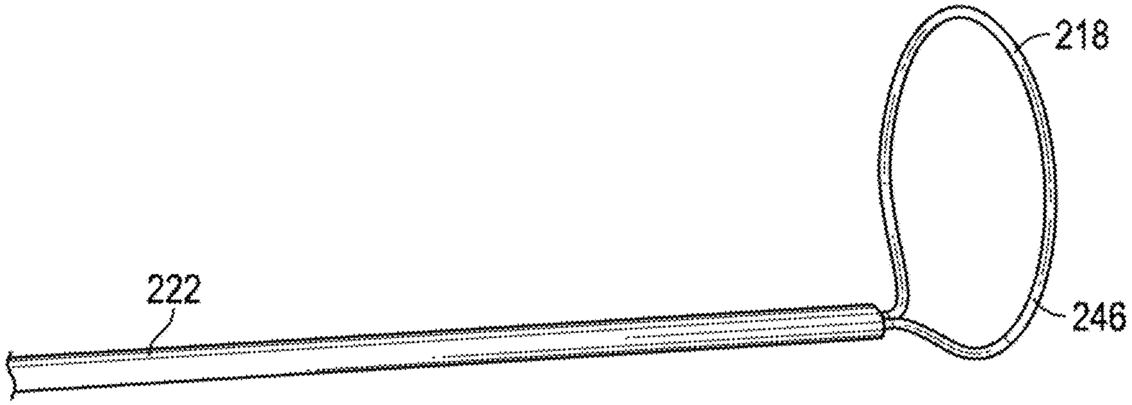

The thermal system 200 may include a loop 218, as illustrated in FIG. 15A. The member 246 (e.g., wire, Nitinol wire) may extend from inside the tip 202, form the loop 218, and extend back inside the tip 202. The loop 218 may be used to fragment (e.g., cut, scoop) the lens 112. The loop 218 may be rotated to fragment the lens 112. The loop 218 may be retracted (e.g., decreasing the size of the diameter) to fragment the lens 112 disposed inside the loop 218. In some variants, one side of the member 246 may be fixed while the other may be advanced and/or retracted to adjust the size of the loop 218. The loop 218 may be heated to soften and/or emulsify the lens 112 as described herein. In some variants, the loop 218 may be fully retracted and/or deployed from inside the tip 202. In some variants, the loop 218 may be used to capture, which can include extracting, the lens 112. The softened and/or emulsified lens 112 may be aspirated as described herein. In some variants, as illustrated in FIG. 15B, the portions of the member 246 not forming the loop 218 may be disposed inside of insulation 222, which can include an insulated sheath, covering, etc., to protect the anatomy of the eye 100 other than the lens 112.

Figure 15C:
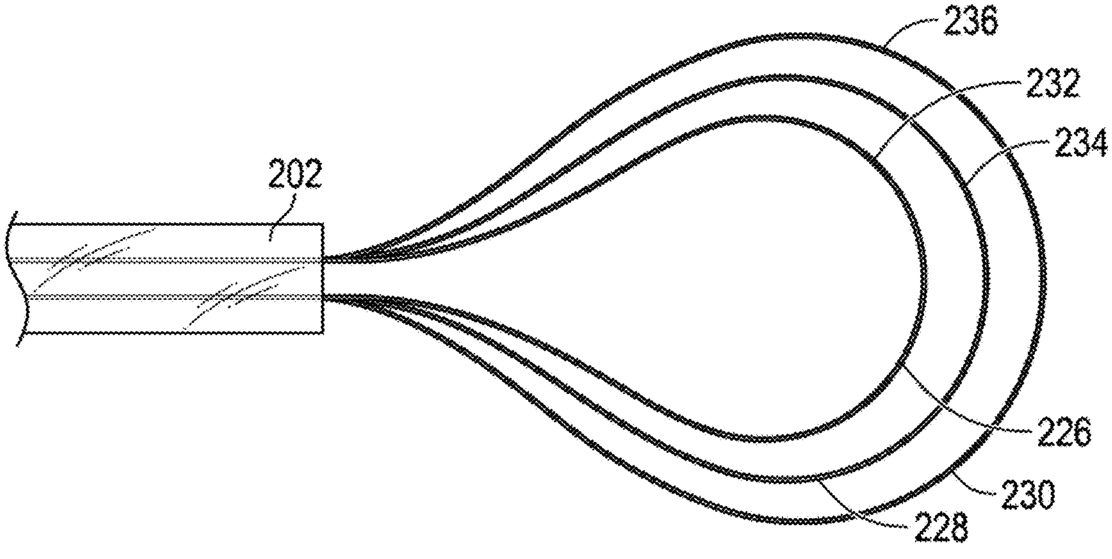
FIG. 15C illustrates a plurality of temperature controlled loops for the thermal system.

As illustrated in FIG. 15C, the thermal system 200 may include a plurality of loops. The plurality of loops can at least include a first loop 226, a second loop 228, and/or a third loop 230. The first loop 226 may be disposed inside of the second loop 228. The second loop 228 may be disposed inside of the third loop 230. The first loop 226 may include a diameter that is smaller than a diameter of the second loop 228. The second loop 228 may include a diameter that is smaller than a diameter of the third loop 230. A first member 232 (e.g., wire, Nitinol wire) may form the first loop 226. A second member 234 (e.g., wire, Nitinol wire) may form the second loop 228. A third member 236 (e.g., wire, Nitinol wire) may form the third loop 230. The first member 226 may extend from inside the tip 202, form the first loop 226, and extend back inside the tip 202. The second member 234 may extend from inside the tip 202, form the second loop 228, and extend back inside the tip 202. The third member 236 may extend from inside the tip 202, form the third loop 230, and extend back inside the tip 202. In some variants, the proximal portions of the first member 232, second member 234, and/or third member 236 may be joined together. The diameters of the first loop 226, second loop 228, and/or third loop 230 may be adjusted, which may be accomplished by way of retracting and/or deploying the first loop 226, second loop 228, and/or third loop 230 from the tip 202. The first loop 226, second loop 228, and/or third loop 230 may be temperature adjusted (e.g., heated, cooled) as described herein. In some variants, one or more of the first loop 226, second loop 228, and/or third loop 230 may be temperature adjusted, which can include independent temperature adjustment. In some variants, the portions of the first member 232, second member 234, and/or third member 236 not forming the first loop 226, second loop 228, and/or third loop 230 may be disposed inside of insulation 222 as described in reference to FIG. 15B.

Figure 16:
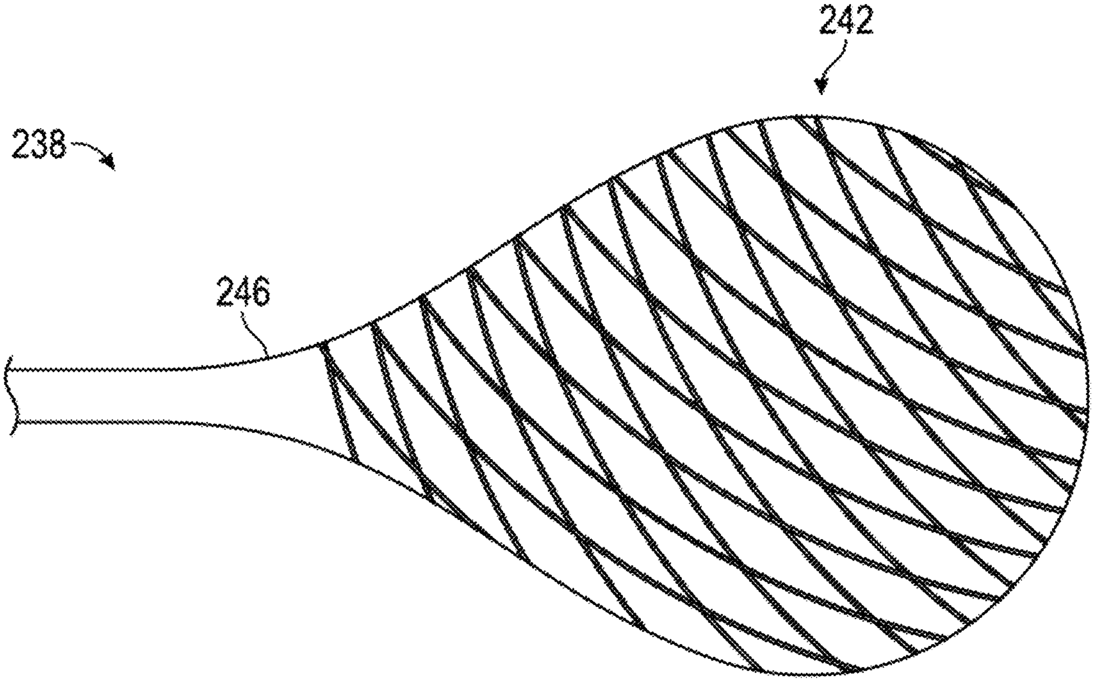
FIG. 16 illustrates a temperature controlled mesh for the thermal system.

FIG. 16 illustrates a mesh tool 238 that may be incorporated into the thermal system 200. The mesh tool 238 may extend from the tip 202, which may include being deployed from and retracted into the tip 202. The mesh 242 may be temperature adjusted (e.g., heated, cooled). The mesh 242 may be connected to a member 246 (e.g., wire, Nitinol wire) that may facilitate temperature adjustment (e.g., heating, cooling) of the mesh 242. The mesh 242 may be made of a metal mesh, such as stainless steel and/or Nitinol. The mesh 242 may be heated to a temperature to soften and/or emulsify the lens 112, which may ease aspiration. The mesh 242 may fragment the lens 112. In some variants, the mesh 242 may be used to capture the lens 112 for removal by way of extraction. The portions of the member 246 not coupled to the mesh 242 may be disposed inside insulation 222.

Systems and Methods Utilizing Heated Fluid

Figure 17:
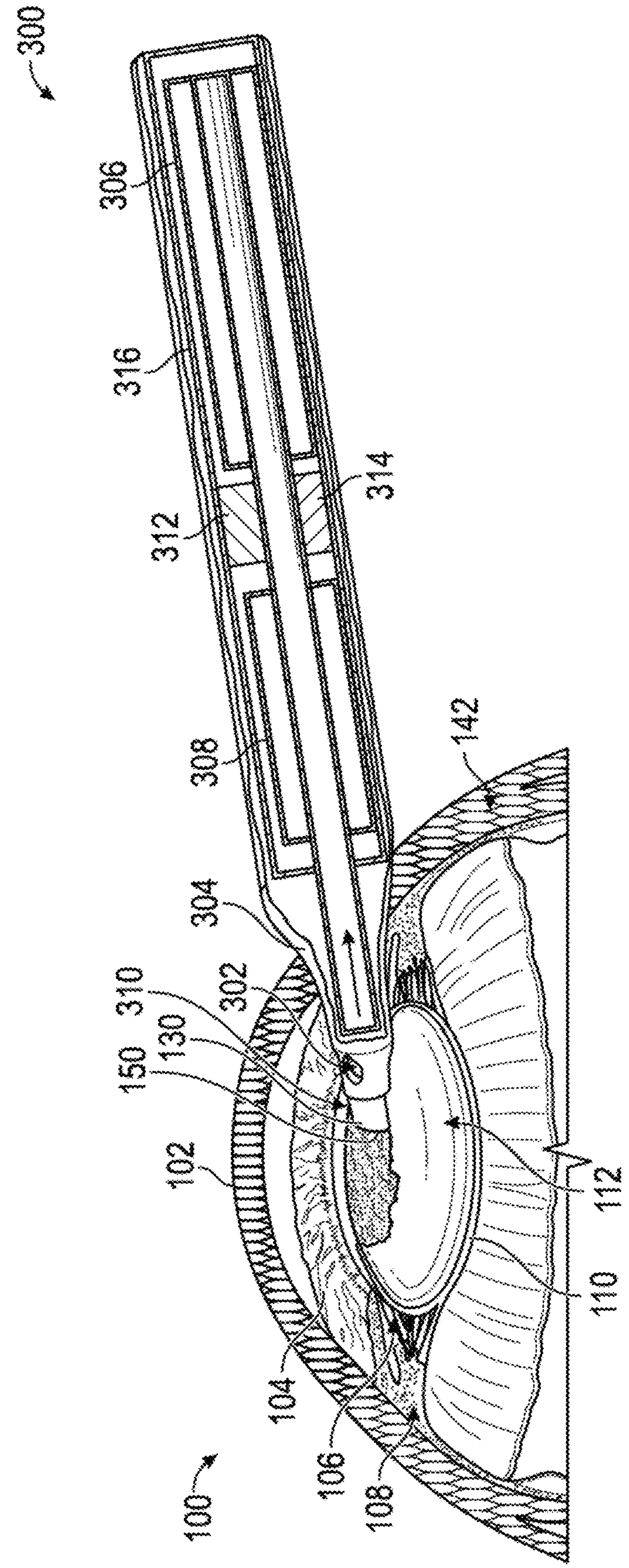
FIG. 17 illustrates a schematic of a handheld system for applying a heated fluid to a crystalline lens.

FIG. 17 illustrates an example thermo-emulsification system 300 (e.g., thermo-emulsification device, system, device, thermo-liquification device, thermo-liquification system, etc.), which can be hand held. The thermo-emulsification system 300 can include a housing 316 that is ergonomically formed for being held by a surgeon performing a cataract surgery. The thermo-emulsification system 300 can be used to liquify (e.g., emulsify) the lens of the eye with a heated fluid. The thermo-emulsification system 300 can include more or less features and/or components than described herein. The thermo-emulsification system 300 can include any of the features described elsewhere herein.

The thermo-emulsification system 300 can include a fluid reservoir 312 (e.g., chamber, compartment, vessel, bag, fluid source, tank). The fluid reservoir 312 can hold a fluid (e.g., saline solution or other fluid suitable for the eye). In some variants, the fluid reservoir 312 may be replaceable. In some variants, the fluid reservoir 312 may be for one-time use (e.g., disposable). For example, the fluid reservoir 312 may be removed after use, discarded as waste, and replaced by a new fluid reservoir 312, which may include a new supply of fluid. In some variants, the fluid reservoir 312 can be reusable. For example, the fluid reservoir 312 can be refilled while integrated with the thermo-emulsification system 300, which can include refilling the fluid reservoir 312 disposed within the housing 316 of the thermo-emulsification system 300. The fluid reservoir 312 can be removed from the housing 316 and then refilled in some instances. The fluid in the fluid reservoir 312 can be irrigated into the eye to liquify (e.g., emulsify) the lens 112.

The thermo-emulsification system 300 can include a waste reservoir 314 (e.g., chamber, compartment, vessel, bag, tank). The waste reservoir 314 can hold the waste matter aspirated from the eye when removing the lens. For example, the liquified (e.g., emulsified) lens, fragments of the lens, aqueous of the eye, and/or fluid introduced into the eye by the thermo-emulsification system 300 can be aspirated into the waste reservoir 314. The waste reservoir 314 may be replaceable. In some variants, the waste reservoir 314 may be for one time use (e.g., disposable). For example, the waste reservoir 314 may be removed after use, discarded as waste, and replaced by a new waste reservoir 314, which may be empty. In some variants, the waste reservoir 314 can be reusable. For example, the waste reservoir 314 can be drained and/or cleaned of waste matter while integrated with the thermo-emulsification system 300, which can include draining and/or cleaning the waste reservoir 314 disposed in the housing 316 of the thermo-emulsification system 300. The waste reservoir 314 can be removed from the housing 316, drained and/or cleaned, and reintegrated into the thermo-emulsification system 300.

The thermo-emulsification system 300 can include a pump system 306, which can be used to irrigate and aspirate within the eye. The pump system 306 can include one or more pumps. The pump system 306 can pump fluid from the fluid reservoir 312 to the lens of the eye (e.g., inside the capsular bag), which can be referred to as irrigating the eye (e.g., capsular bag). The pump system 306 can pump waste matter from the eye (e.g., capsular bag), such as the liquified (e.g., emulsified) lens, fragments of the lens, aqueous of the eye, and/or fluid from the fluid reservoir 312 introduced into the eye, into the waste reservoir 314, which can be referred to as aspirating from the eye.

The thermo-emulsification system 300 can include a heating element and control system 308, which can also be described as the temperature adjustment system. The heating element and control system 308 can alter the temperature of the fluid delivered to the lens. In some variants, the heating element and control system 308 can raise and/or lower the temperature (e.g., heat and/or cool) of the fluid. In some variants, the heating element and control system 308 can only raise the temperature (e.g., heat) the fluid. In some variants, the heating element and control system 308 can adjust the temperature of the fluid downstream of the fluid reservoir 312. In some variants, the heating element and control system 308 can adjust the temperature of the fluid at delivery into the eye. In some variants, the heating element and control system 308 can adjust the temperature of the fluid in the fluid reservoir 312. The heating element and control system 308 can adjust the temperature of the fluid with conduction, convection, and/or radiation.

The thermo-emulsification system 300 can include a tip 130 (e.g., cannula). The tip 130 can be disposed on a distal end of the thermo-emulsification system 300, which can include being disposed on a distal end of the housing 316. The tip 130 can be placed inside the eye and proximate the lens 112. The tip 130 can be made of variety of material, which can include metals, metal alloys, polymers, ceramics, etc. The tip 130 can include an opening 150. Fluid can be delivered from the fluid reservoir 312 to the lens 112 through the opening 150. The thermo-emulsification system 300 can include insulation 304 proximate the tip 130 to protect surrounding anatomy of the eye, which can include protecting surrounding anatomy of the eye from heat as the thermo-emulsification system 300 is being operated. The insulation 304 can be disposed circumferentially around the tip 130. In some variants, fluid can be aspirated through the opening 150 of the tip 130.

The thermo-emulsification system 300 can include a temperature sensor 310 (e.g., thermocouple). The temperature sensor 310 can sense (e.g., detect) the temperature of the fluid being delivered to the eye at the point of delivery (e.g., at the tip 130). The temperature sensor 310 can sense the temperature within the eye. The temperature sensor 310 and heating element and control system 308 can be in communication. The heating element and control system 308 can adjust the temperature of the fluid being delivered to the lens based on the temperature sensed by the temperature sensor 310. For example, the temperature of the fluid may drop from a target temperature due to heat loss prior to delivery to the lens. The temperature sensor 310 can sense the lowered temperature of the fluid resulting from heat loss prior to delivery, and in response to receiving an indication of the lowered temperature of the fluid from the temperature sensor 310, the heating element and control system 308 can raise the temperature of the fluid to accommodate for the heat loss.

The thermo-emulsification system 300 can include a port 302 (e.g., opening, aperture). The port 302 can be used to aspirate waste matter from the eye. In some variants, heated fluid and/or nonheated fluid can be delivered to the lens from the port 302. The pump system 306 can aspirate (e.g., vacuum, suck) waste matter from within the eye (e.g., capsular bag) through the port 302 and into the waste reservoir 314. The port 302 can be disposed at various positions. In some variants, the port 302 can be disposed in the insulation 304. In some variants, the port 302 can be disposed on the distal end of the tip 130. In some variants, the port 302 can be disposed on the side of the tip 130. The port 302 can be various sizes and/or shapes, which can include a circle, polygon (e.g., triangle, square, rectangle, pentagon, etc.), oval, irregular, or others.

The thermo-emulsification system 300 can irrigate and aspirate at the same time and/or different times. For example, the pump system 306 can irrigate (e.g., pump, urge) heated fluid into the eye by way of the opening 150 to liquify and/or soften the lens. The pump system 306 can aspirate (e.g., pump, vacuum, urge) the fluid irrigated into the eye, aqueous of the eye, fragments of the lens, and/or liquified lens material through the port 302 and into the waste reservoir 314.

In some variants, the thermo-emulsification system 300 can be reusable. For example, the various components (e.g., tip 130, fluid reservoir 312, waste reservoir 314, and/or others) of the thermo-emulsification system 300 can be cleaned for reuse, which may include disassembly and cleaning. In some variants, the various components (e.g., tip 130, fluid reservoir 312, waste reservoir 314, and/or others)

of the thermo-emulsification system 300 can be intended for one-time use such that the various components can be removed, discarded, and replaced with new components.

In some variants, the thermo-emulsification system 300 can be intended for one-time use. For example, the thermo-emulsification system 300 can be used to remove one or both lenses from a patient and then discarded. In some variants, the thermo-emulsification system 300 can be used to only remove one lens such that removing both lenses of a patient requires two thermo-emulsification systems 300. In some variants, the thermo-emulsification system 300 can be used to remove both of a patient's lenses and then discarded, which can include replacing the fluid reservoir 312 and/or waste reservoir 314 after removing the first lens.

The thermo-emulsification system 300 can include a power source, such as one or more batteries. In some variants, the one or more batteries may be for one-time use. In some variants, the one or more batteries may be rechargeable.

The thermo-emulsification system 300 can include a power interface. The power interface can be used to recharge the battery and/or power the thermo-emulsification system 300. In some variants, the thermo-emulsification system 300 may not include a battery but, instead, rely on wired power which can supply power by way of the power interface. In some variants, the one or more batteries can be recharged with wireless charging by way of the power interface.

The thermo-emulsification system 300 can include one or more processor(s), controller(s), valve(s) (e.g., pinch valve(s), solenoid valve(s), proportional solenoid valve(s)), diverter(s), sensor(s) (e.g., flow sensor(s)), filter(s), driver(s), speaker(s), indicator light(s), user interface(s) (e.g., button(s), dial(s), knob(s), touch screen(s), switch(es)), display(s), memory with software, microphone(s), regulator(s), clock(s) (e.g., real-time clocks), internal tubing, communication interfaces (e.g., wireless and/or wired), and/or other features. The valve(s) can be used to open and/or close flow out of the fluid reservoir 312. The valve(s) can be used to open and/or close flow into the waste reservoir 314. The speaker(s), indicator lights, and/or display(s) can emit warnings for safety (e.g., the temperature sensor 310 has detected a temperature that is unsafe, the flow sensor(s) have detected an unsafe flow, the fluid in the fluid reservoir 312 is below a threshold, the waste matter in the waste reservoir 314 is above a threshold, etc.). The speaker(s), lights (e.g., indicator lights), and/or display(s) can indicate the status of the thermo-emulsification system 300 (e.g., on/off, the fluid has been heated to the appropriate temperature, battery level, mode, etc.). The user interface(s) can be used to control the thermo-emulsification system 300 (e.g., start/stop irrigation, start/stop aspiration, adjust temperature, change modes, control a light, etc.). The microphone(s) can receiver verbal instructions. The light(s) can be used to increase visibility within the eye during surgery.

Figure 18:
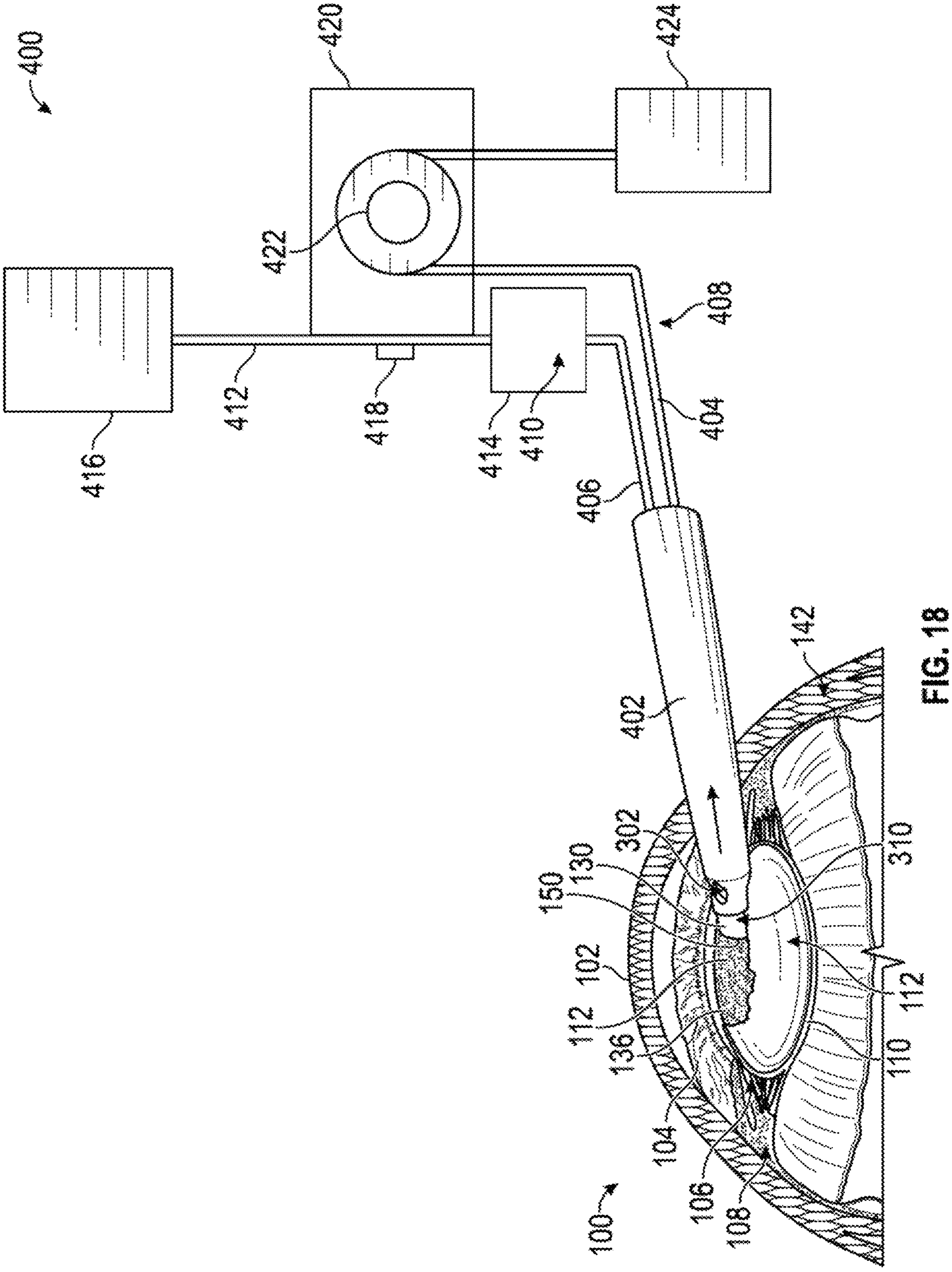
FIG. 18 illustrates a schematic of a phaco system with features to apply a heated fluid to a crystalline lens.

FIG. 18 illustrates an example thermo-emulsification system 400 (e.g., thermo-emulsification device, system, device, thermo-liquification device, thermo-liquification system, etc.). In some variants, the thermo-emulsification system 400 can be incorporated with a phaco machine (e.g., retro-fitted to a phaco machine, to modify a phaco machine). The thermo-emulsification system 400 can include any of the features described in reference to other systems herein. The thermo-emulsification system 400 can include less or more features than those described herein.

The thermo-emulsification system 400 can include a handheld tool 402 (e.g., handheld instrument, tool, instrument), which can be a phaco handpiece. The handheld tool 402 can include one or more, which can include all, of the features described in reference to thermo-emulsification system 300 and/or other systems herein.

The thermo-emulsification system 400 can include a fluid reservoir 416 (e.g., fluid source, chamber, compartment, vessel, bag, tank). The handheld tool 402 can be fluidically coupled with the fluid reservoir 416. The fluid reservoir 416 can be positioned at an elevated position relative to the handheld tool 402. The fluid reservoir 416, in some variants, can be an IV bag. The fluid reservoir 416 can hold a fluid (e.g., saline solution). The fluid reservoir 416 can be fluidically coupled with the handheld tool 402 by way of an irrigation tube 406 (e.g., tube, line, conduit). The irrigation tube 406, in some variants, can be insulated to decrease heat loss as the fluid travels from the fluid reservoir 416 to the handheld tool 402. The fluid in the fluid reservoir 416 can be delivered to the lens of the eye to liquify and/or soften the lens for removal. In some variants, the fluid reservoir 416 can be cleaned and reused. In some variants, the fluid reservoir 416 can be discarded after use and replaced with a new fluid reservoir 416 filled with fluid. In some variants, the various components of the thermo-emulsification system 400 can be intended for one-time use (e.g., for removal of both lenses of a patient or removal of one lens of a patient).

The thermo-emulsification system 400 can include a heating element and control system 414, which can also be described as the temperature adjustment system. The heating element and control system 414 can adjust the temperature of the fluid delivered to the lens. In some variants, the heating element and control system 414 can raise and/or lower the temperature (e.g., heat and/or cool) of the fluid. In some variants, the heating element and control system 414 can only raise the temperature (e.g., heat) the fluid. The heating element and control system 414 can be disposed along the irrigation tube 406. The heating element and control system 414 can be disposed along the irrigation tube 406 between the fluid reservoir 416 and the handheld tool 402. In some variants, the heating element and control system 414 can be disposed at the fluid reservoir 416 to adjust the temperature of the fluid in the fluid reservoir 416. In some variants, the heating element and control system 414 can include components (e.g., heating elements) at one of or both the fluid reservoir 416 to adjust the temperature of the fluid in the fluid reservoir 416 and along the irrigation tube 406 and/or at the handheld tool 402 to further adjust the temperature of the fluid after leaving the fluid reservoir 416. The heating element and control system 414 can adjust the temperature of the fluid with conduction, convection, and/or radiation.

The thermo-emulsification system 400 can include one or more temperature sensors (e.g., thermocouples) at various positions. For example, the thermo-emulsification system 400 can include a temperature sensor at the fluid reservoir 416 to measure the temperature of the fluid held in the fluid reservoir 416. The thermo-emulsification system 400 can include one or more temperature sensors along the irrigation tube 406. The thermo-emulsification system 400 can include one or more temperature sensors at the heating element and control system 414. The thermo-emulsification system 400 can include a temperature sensor 412 (e.g., thermocouple) along the irrigation tube 406 between the fluid reservoir 416 and the heating element and control system 414 (e.g. downstream of the fluid reservoir 416 and upstream of the heating element and control system 414). The temperature of the fluid measured at the temperature sensor 412 can be a factor in determining the quantity of energy to be output by the heating element and control system 414 to adjust the temperature of the fluid to a desired temperature. The thermo-emulsification system 400 can include a temperature sensor 410 at the heating element and control system 414. The thermo-emulsification system 400 can include the temperature sensor 310 at the tip 130 (e.g., cannula). The temperatures sensed by the various temperature sensors of the thermo-emulsification system 400 can be used to control the energy output by the heating element and control system 414 to adjust the temperature of the fluid.

The thermo-emulsification system 400 can include one or more valves. For example, the thermo-emulsification system 400 can include a valve 418, which can be a pinch valve. The valve 418 can be manipulated to start and stop flow of the fluid from the fluid reservoir 416 to the handheld tool 402. The valve 418 or another component can adjust the flow rate of the fluid from the fluid reservoir 416 to the handheld tool 402. In some variants, the handheld tool 402 can include a valve or other component to adjust the flow rate of the fluid into the eye. The valve 418 can be manually operated or electronically operated. The valve 418 may automatically close if a triggering event occurs (e.g., a sensed temperature is above or below a threshold).

The thermo-emulsification system 400 can include a waste reservoir 424 (e.g., chamber, compartment, vessel, bag, tank). The waste reservoir 424 can be fluidically coupled with the handheld tool 402. The waste reservoir 424 can be fluidically coupled with the handheld tool 402 by way of an aspiration tube 404 (e.g., tube, line, conduit). The aspiration tube 404, in some variants, can be insulated. In some variants, the thermo-emulsification system 400 can include a temperature sensor 408 along the aspiration tube 404 to sense the temperature of the waste matter flowing therein. The thermo-emulsification system 400 can include a temperature sensor at the waste reservoir 424. The waste reservoir 424 can hold the waste matter aspirated from the eye when removing the lens. For example, the liquified (e.g., emulsified) lens, fragments of the lens, aqueous of the eye, and/or fluid introduced into the eye by the thermo-emulsification system 400 can be aspirated into the waste reservoir 424. The waste reservoir 424 can be replaceable. The waste reservoir 424 may be for one-time use (e.g., disposable). For example, the waste reservoir 424 may be removed after use, discarded as waste, and replaced by a new waste reservoir 424, which may be empty. In some variants, the waste reservoir 414 can be reusable. For example, the waste reservoir 414 can be drained and/or cleaned of waste matter while integrated with the thermo-emulsification system 400. The waste reservoir 424 can be removed from the thermo-emulsification system 400, drained and/or cleaned, and reintegrated into the thermo-emulsification system 400.

The thermo-emulsification system 400 can include a pump system 422, which can include one or more pumps. The pump system 422 can pump the waste matter from the eye and into the waste reservoir 424 (e.g., into the handheld tool 402, through the aspiration tube 404, and into the waste reservoir 424). The pump system 422 can be part of a phaco machine 420. In some variants, the aspiration tube 404, temperature sensor 408, and/or waste reservoir 424 can be components for the phaco machine 420 that cooperate with the thermo-emulsification system 400. In some variants, the pump system 422 can pump fluid from the fluid reservoir 416 and into the eye (e.g., through the irrigation tube 406, into the handheld tool 402, and into the eye). In some variants, the fluid in the fluid reservoir 416 can flow from gravity rather than the pump system 422. For example, the fluid reservoir 416 can be disposed at an elevated position such that gravity causes the fluid to flow out of the fluid reservoir 416, through the irrigation tube 406, and into the handheld tool 402 for delivery. As described herein, the thermo-emulsification system 400 can include a valve (e.g., valve 418) and/or other flow regulator to adjust the flow of the fluid. In some variants, one or more valves (e.g., one-way valve) can be disposed along the aspiration tube 404, within the handheld tool 402, and/or at the waste reservoir 424 to prevent backflow of the waste matter.

The thermo-emulsification system 400 can irrigate and aspirate at the same time and/or different times. In some variants, the thermo-emulsification system 400 can be reusable. For example, the various components (e.g., tip 130, fluid reservoir 416, waste reservoir 424, and/or others) of the thermo-emulsification system 400 can be cleaned for reuse, which may include disassembly and cleaning. In some variants, the various components (e.g., tip 130, fluid reservoir 416, waste reservoir 424, and/or others) of the thermo-emulsification system 400 can be intended for one-time use such that the various components can be removed, discarded, and replaced with new components.

In some variants, the thermo-emulsification system 400 or components thereof can be intended for one-time use. For example, the thermo-emulsification system 400 or components thereof can be used to remove one or both lenses from a patient and then discarded. In some variants, the thermo-emulsification system 400 or components thereof can be used to only remove one lens such that removing both lenses of a patient requires two thermo-emulsification systems 400 or replacement of some of the components. In some variants, the thermo-emulsification system 400 or components thereof can be used to remove both of a patient's lenses and then discarded, which can include replacing the fluid reservoir 416 and/or waste reservoir 424 after removing the first lens.

The thermo-emulsification system 400, which can include components thereof, can include a power source, such as one or more batteries. In some variants, the one or more batteries may be for one-time use. In some variants, the one or more batteries may be rechargeable.

The thermo-emulsification system 400 can include a power interface. The power interface can be used to recharge the battery and/or power the thermo-emulsification system 400. In some variants, the thermo-emulsification system 400 may not include a battery but, instead, rely on wired power which can supply power by way of the power interface. In some variants, the one or more batteries can be recharged with wireless charging by way of the power interface.

The thermo-emulsification system 400 can include one or more processor(s), controller(s), valve(s) (e.g., pinch valve(s), solenoid valve(s), proportional solenoid valve(s)), diverter(s), sensor(s) (e.g., flow sensor(s)), filter(s), driver(s), speaker(s), indicator light(s), user interface(s) (e.g., button(s), dial(s), knob(s), touch screen(s), switch(es)), display(s), memory with software, microphone(s), regulator(s), clock(s) (e.g., real-time clocks), tubing, communication interfaces (e.g., wireless and/or wired), and/or other features. The speaker(s), indicator lights, and/or display(s) can emit warnings for safety (e.g., a temperature sensor has detected a temperature that is unsafe, a flow sensor(s) has detected an unsafe flow, the fluid in the fluid reservoir 416 is below a threshold, the waste matter in the waste reservoir 424 is above a threshold, etc.). The speaker(s), lights (e.g., indicator lights), and/or display(s) can indicate the status of the thermo-emulsification system 400 (e.g., on/off, the fluid has been heated to the appropriate temperature, battery level, mode, etc.). The user interface(s) can be used to control the thermo-emulsification system 400

(e.g., start/stop irrigation, start/stop aspiration, adjust temperature, change modes, control a light, etc.). The microphone(s) can receiver verbal instructions. The light(s) can be used to increase visibility within the eye during surgery.

Figure 19:
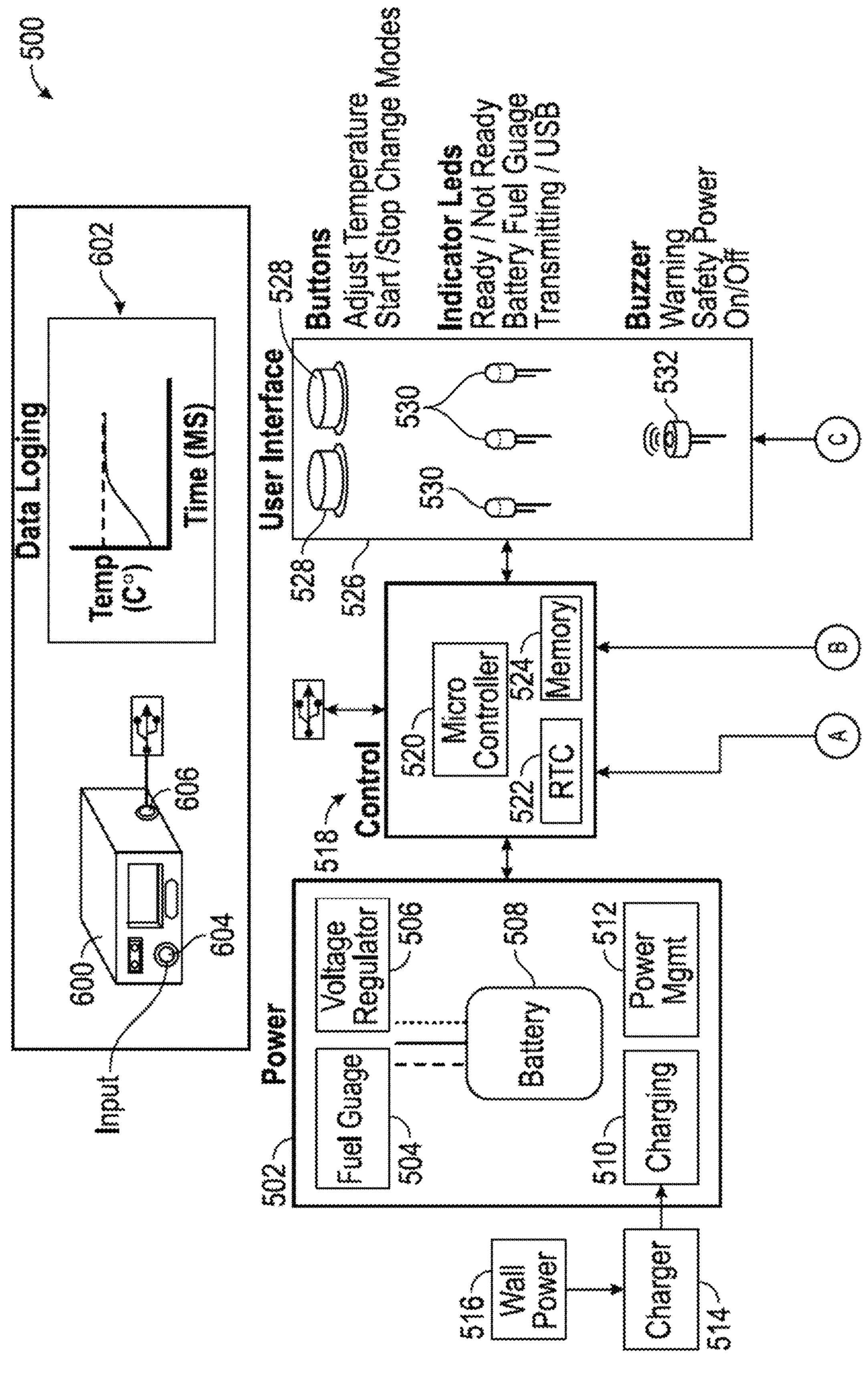
FIG. 19 illustrates a schematic of a system for supplying a heated fluid for emulsifying a crystalline lens.
Figure 19:
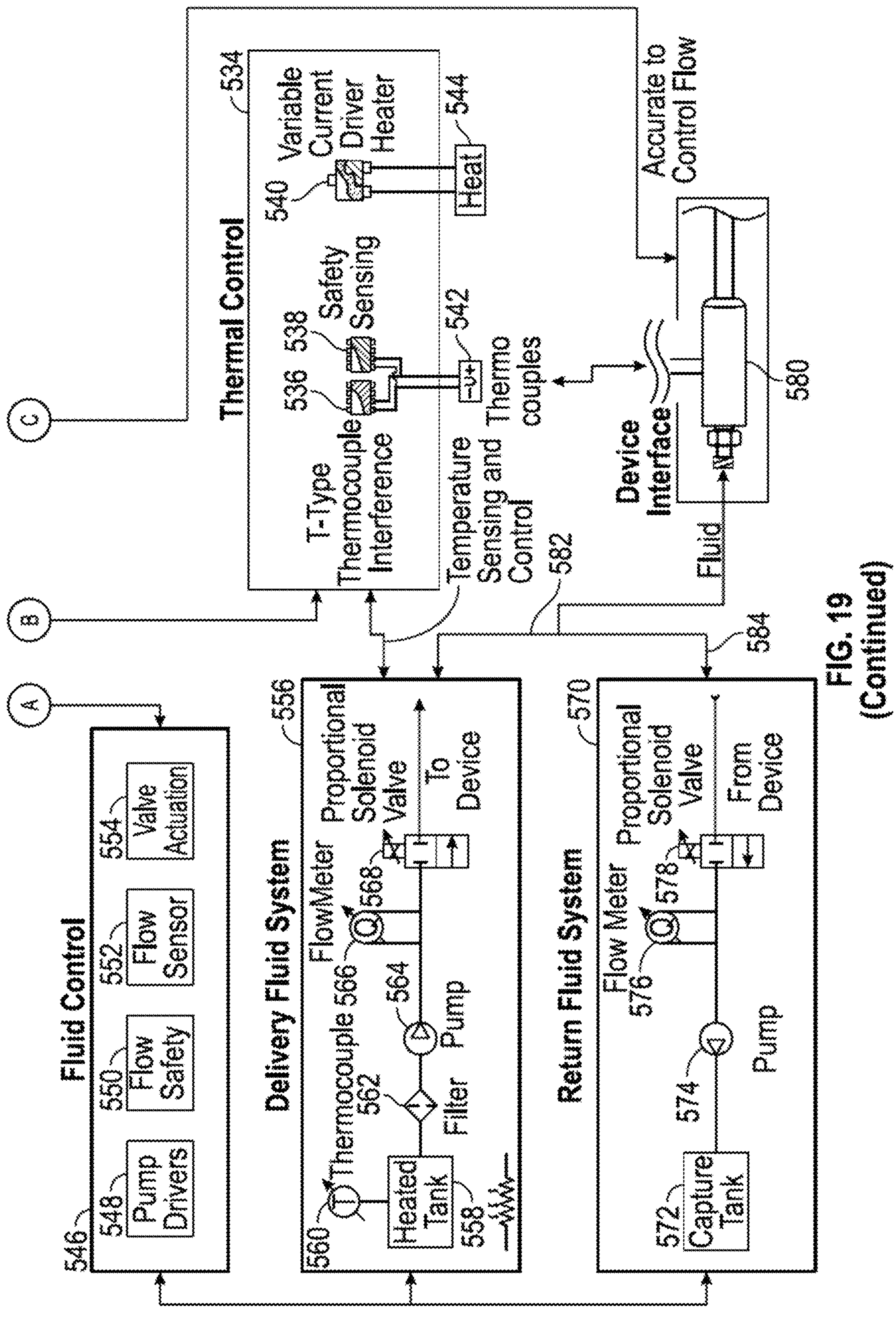

FIG. 19 illustrates an example thermo-emulsification system 500 (e.g., thermo-emulsification device, system, device, thermo-liquification device, thermo-liquification system, etc.). In some variants, the thermo-emulsification system 500 can be incorporated with a phaco machine (e.g., retrofitted to phaco machine, to modify a phaco machine). The thermo-emulsification system 500 can include any of the features described in reference to other systems herein. The thermo-emulsification system 500 can include more or less than the features shown and described, as can the other systems described herein.

The thermo-emulsification system 500 can include a device interface 580 (e.g., interface). The device interface 580 can interface with a tool (e.g., handheld tool 402, phaco handpiece) that delivers the heated fluid to the eye and/or aspirates waste material from the eye.

The thermo-emulsification system 500 can include a delivery fluid system 556. The delivery fluid system 556 can include a heated tank 558 (e.g., a fluid source, fluid reservoir, chamber, compartment, vessel, bag, tank). The heated tank 558 can hold a fluid (e.g., saline solution). At the exit of the heated tank 558 and/or downstream from the heated tank 558, the delivery fluid system 556 can include a filter 562, pump 564, flow meter 566, and/or valve 568 (e.g., proportional solenoid valve). The filter 562 can capture unwanted particles. The pump 564 can draw fluid out of the heated tank 558 and urge the fluid down a fluid delivery line 582 (e.g., tube, conduit) to the device interface 580. The flow meter 566 can detect the flow rate and/or other characteristics of the fluid. The valve 568 can open and close to stop, allow, and/or adjust the flow of fluid therethrough. The detected flow rate and/or other characteristics of the fluid can be used to control the pump 564 to adjust the flow rate of the fluid and/or adjust the valve 568 to adjust the flow rate of the fluid through the fluid delivery line 582 to the device interface 580.

The thermo-emulsification system 500 can include a thermal control system 534. The thermal control system 534 can adjust the temperature of the fluid delivered to the eye. For example, the thermal control system 534 can adjust the temperature of the fluid (e.g., heat the fluid) in the heated tank 558. The thermal control system 534 can include a heater 540 (e.g., variable current driver). The heater 540 can include a heating element 544 that can heat the fluid in the heated tank 558, which can include fluid exiting the heated tank 558. The thermal control system 534 can include a temperature sensor interface 536 (e.g., T-type thermocouple interface) and/or safety sensor 538. The thermal control system 534 can include a temperature sensor 542 (e.g., thermocouple) that operatively couples with the temperature sensor interface 536. The temperature sensor 542 can sense the temperature of the fluid in the heated tank 558, which can be used by the thermal control system 534 to adjust the energy (e.g., current) output by the heater 540 to adjust the temperature of the fluid in the heated tank 558 to a desired target temperature. The temperature sensor (thermocouple) 542 can be disposed at the heated tank 558, which can include in the heated tank 558.

The thermo-emulsification system 500 can include a return fluid system 570 (e.g., waste matter system, aspiration system). The return fluid system 570 can include a capture tank 572 (e.g., chamber, compartment, vessel, bag, tank). The capture tank 572 can hold the waste matter aspirated from the eye when removing the lens. For example, the liquified (e.g., emulsified) lens, fragments of the lens, aqueous of the eye, and/or fluid introduced into the eye by the thermo-emulsification system 500 can be aspirated into the capture tank 572. The return fluid system 570 can include a pump 574, flow meter 576, and/or valve 578 (e.g., proportional solenoid valve). The pump 574 can aspirate (e.g., urge, vacuum) waste matter from the eye, into the handheld device, through the device interface 580, through a fluid return line 584 (e.g., tube, conduit), and into the capture tank 572. The flow meter 576 can be used to measure the flow rate and/or other characteristics of the waste matter through the fluid return line 584. The valve 578 can open and/or close to stop, allow, and/or adjust the flow of fluid therethrough to the capture tank 572. In some variants, the valve 578 is a one way valve to prevent backflow. The detected flow rate and/or other characteristics of the fluid can be used to control the pump 574 to adjust the flow rate of the fluid and/or adjust the valve 578 to adjust the flow rate of the fluid through the fluid return line 584 to the capture tank 572.

The thermo-emulsification system 500 can include a fluid control system 546. The fluid control system 546 can control the flow of fluid through the thermo-emulsification system 500. The fluid control system 546 can include one or more pump drivers 548, flow safety module 550, flow sensor interface 552, and/or valve actuation controller 554. The pump drivers 548 can operate the pump 564 and/or pump 574. The flow sensor interface 552 can communicate with the flow meter 566 and/or flow meter 576 to receive indications of the sensed flow rates. The valve actuation controller 554 can be used to control the valve 568 and/or valve 578. The pump drivers 548 and/or valve actuation controller 554 can adjust the flow rate or even stop flow when certain conditions are met. For example, if the flow is too high (e.g., above a threshold) in the fluid delivery line 582 and/or fluid return line 584, the pump drivers 548 and/or valve actuation controller 554 can control the pump 564, pump 574, valve 568, and/or valve 578 to decrease flow to a target. If the flow is too low (e.g., below a threshold) in the fluid delivery line 582 and/or fluid return line 584, the pump drivers 548 and/or valve actuation controller 554 can control the pump 564, pump 574, valve 568, and/or valve 578 to increase flow to a target.

The thermo-emulsification system 500 can include a power system 502 to power the thermo-emulsification system 500. The power system 502 can include a battery 508, which can be rechargeable. The power system 502 can include a charging interface 510. The charging interface 510 can interface with a charger device 514 (e.g., cable) to supply power from a power source 516 (e.g., power outlet) to charge the battery 508 and/or supply power directly to the thermo-emulsification system 500. The power system 502 can include a power management module 512, a voltage regulator 506, and/or gauge 504 (e.g., power gauge, power indicator, battery power level indicator).

The thermo-emulsification system 500 can include a control system 518. The control system 518 can include a micro controller 520, real-time clock 522 (e.g., RTC), and/or memory 524. The real-time clock 522 can be used to identify triggering events for the thermo-emulsification system 500 to respond to. For example, the thermo-emulsification system 500 may slow the flow rate in the fluid delivery line 582 if the flow rate is above a threshold for a period of time (e.g., one second). The control system 518 may interface with a data analysis system 600. The data analysis system 600 can be used to log and analyze data regarding the thermo-emulsification system 500. The data analysis system 600 can include a port 606 by which the thermo-emulsification system 500 can connect. The data analysis system 600 can include an input 604, through which the data analysis system 600 can connect to other computing systems. Data log 602 displays a graph of the fluid temperature in the heated tank 558 as a function of time.

The thermo-emulsification system 500 can include a user interface system 526. The user interface system 526 can include one or more button(s) 528, which can at least be used to adjust temperature of the fluid, start/stop irrigation and/or aspiration, change modes, adjust flow rates, open and/or shut valves, power on/off, and/or other adjustments. The user interface system 526 can, in some variants, include dial(s), switch(es), display(s), touchpad(s), touchscreen(s), knob(s), trigger(s), indicator(s), gauge(s), slider(s), and/or other features. The user interface system 526 can include indicator(s) 530 (e.g., indicator lights, such as LEDs). The indicator(s) 530 can visually indicate when the thermo-emulsification system 500 is ready for operation and/or not ready for operation. The indicator(s) 530 can visually indicate when the thermo-emulsification system 500 is aspirating and/or irrigating. The indicator(s) 530 can indicate the charge level of the battery 508. The indicator(s) 530 can indicating when the thermo-emulsification system 500 is communicating with another computing system (e.g., transmitting data). The indicator(s) 530 can emit warnings to the surgeon. The indicator(s) 530 can emit various colors and/or patterns of light. The user interface system 526 can include a speaker(s) 532 (e.g., buzzer), which can emit audible sounds to communicate warnings, alert of safety issues, and/or emit sounds when various actions are performed (e.g., power on/off). In some variants, the user interface system 526 can include one or more displays, touchscreens, microphones for spoken commands, etc. In some variants, the indicator(s) 530, speaker(s) 532, display, touchscreen, etc. can indicate the fill level of the heated tank 558 and/or capture tank 572, which can include warning when the fill level has dropped below or risen above a threshold. In some variants, the indicator(s) 530, speaker(s) 532, display, touchscreen, etc. can communicate an indication of how long the thermo-emulsification system 500 has been in use, which can indicate to a surgeon how much longer the eye can safely be irrigated with heated fluid.

The thermo-emulsification system 500, in some variants, can include a wired communication interface and/or a wireless communication interface to communicate with other computing devices. The thermo-emulsification system 500 can, in some variants, include a light to illuminate the eye during surgery.

Figure 20A:
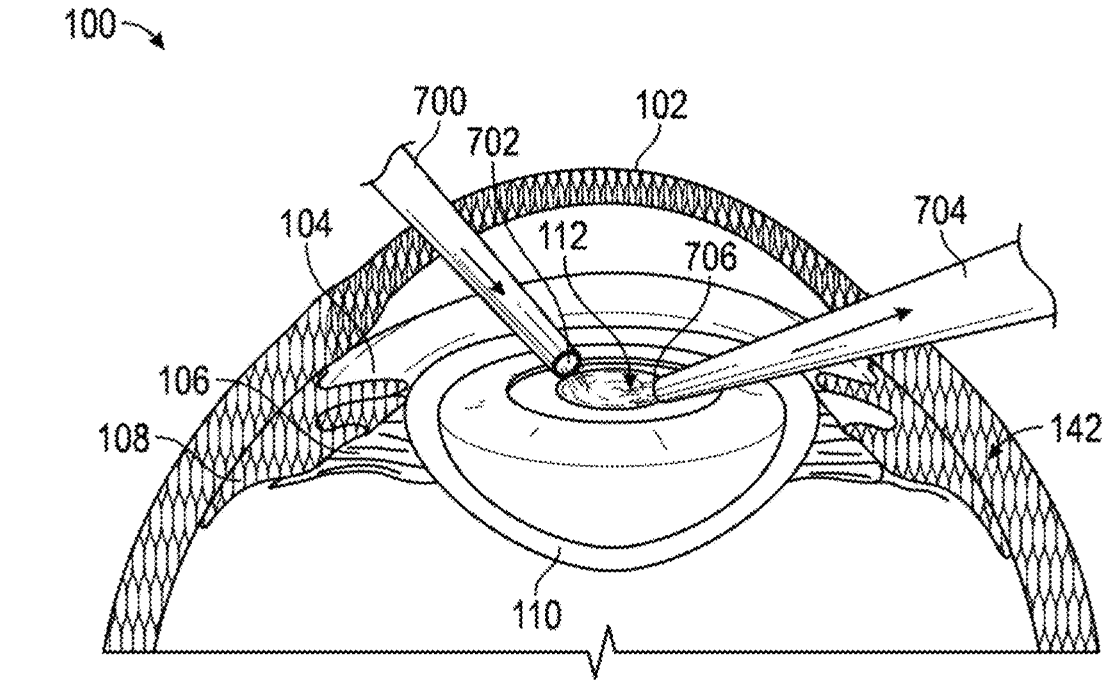
FIGS. 20A-20C illustrate an irrigation tip applying a heated fluid to a crystalline lens of an eye and an aspiration tip aspirating the emulsified crystalline lens. The irrigation and aspiration tips are positioned with distal openings of the irrigation and aspiration tips generally facing each other.
Figure 20B:
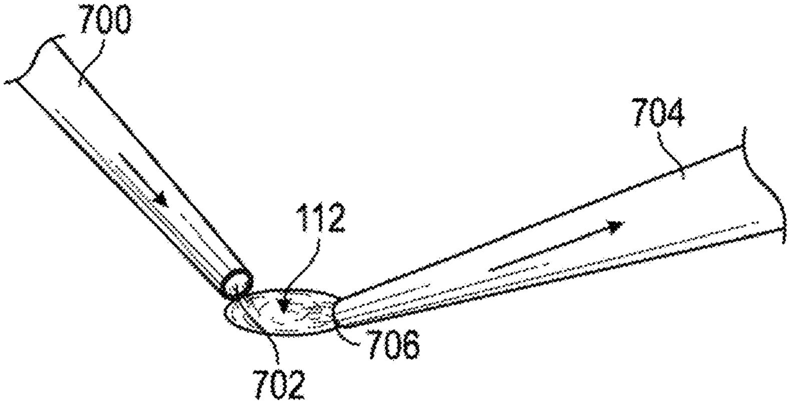
Figure 20C:
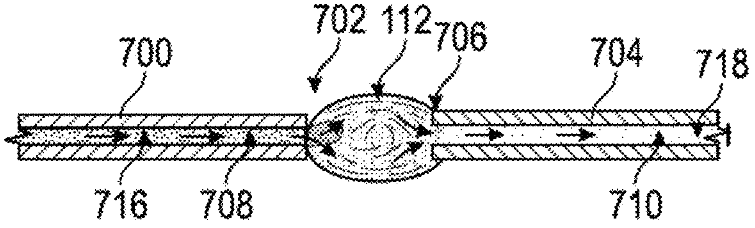

FIGS. 20A-20C illustrate a bimanual irrigation and aspiration method using heated fluid to liquify the lens 112 for aspiration. As illustrated in FIG. 20A, dual small microincisions (e.g., less than 3 mm) can be made in the cornea 102 to provide access into the eye 100 after administering local anesthesia and preparing the eye 100 for surgery. These dual small microincisions can be off axis to reduce impact on vision and be placed similarly to incisions used in manual small-incision cataract surgery (MSICS). However, the dual small microincisions created can be smaller than those incisions currently made during MSICS. The anterior of the capsular bag 110 can be cut open to access the lens 112. In some variants, two small microincisions can be in the anterior of the capsular bag 110 (e.g., off axis) to access the anterior of the capsular bag 110, which can avoid Capsulorhexis. In some variants, Capsulorhexis can be performed to penetrate the capsular bag 110 to access the lens 112 therein.

An irrigation tip 700 (e.g., cannula) can be introduced into the eye 100 and to the lens 112 through one microincision. An aspiration tip 704 (e.g., cannula) can be introduced into the eye 100 and to the lens 112 through another microincision. The irrigation tip 700 and aspiration tip 704 can be disposed generally opposite each other (e.g., about one hundred and eighty degrees apart from each other). Fluid heated to one of the temperature ranges described herein (e.g., 64-70 degrees, 66-70 degrees Celsius, 68-70 degrees Celsius) can be delivered from an opening 702 (e.g., distal opening, aperture) of the irrigation tip 700 to the lens 112. The opening 702 can be disposed on a distal end of the irrigation tip 700. The heated fluid can liquify the lens 112 as described herein. The heated fluid can penetrate the lens 112. The heated fluid can apply low pressure on the lens 112.

The liquified lens 112 can be aspirated (e.g., vacuumed, sucked) through an opening 706 (e.g., distal opening, aperture) of the aspiration tip 704 for removal. The opening 706 can be disposed on a distal end of the aspiration tip 704. The aspiration tip 704 can aspirate waste material (e.g., liquified lens 112, aqueous of the eye 100, fragments of the lens, and/or fluid introduced into the eye 100 by the irrigation tip 700). The aspiration tip 704 can be disposed proximate the irrigation tip 700, which can include opposite each other, to quickly aspirate heated fluid and/or liquified lens 112 from the eye 100. The irrigation tip 700 and aspiration tip 704 can be positioned such that the opening 702 of the irrigation tip 700 and the opening 706 of the aspiration tip 704 generally face each other. The aspiration tip 704 can quickly aspirate the heated fluid and/or liquified lens 112 to keep heat localized.

As described herein, the fluid can be heated in a tank or the like upstream of the irrigation tip 700. For example, as illustrated in FIG. 20C, the heated fluid 708 can be transported through an internal lumen 716 and out of the opening 702 of the irrigation tip 700 to the lens 112 to liquify the lens 112. The liquified lens 112 and/or other waste material can be aspirated through an opening 706 and into an internal lumen 718 of aspiration tip 704. The aspirated material 710 can flow to a waste reservoir for disposal. In some variants, the fluid can be heated at the irrigation tip 700, which can include at the opening 702.

In some variants, the irrigation tip 700 and the aspiration tip 704 can be a single tip that first irrigates the heated fluid and then aspirates the heated fluid and liquified lens 112.

In some variants, the irrigating and aspiration can be performed in series using the same incisions in the cornea 102 and/or capsular bag 110. For example, the irrigation tip 700 can be introduced to liquify the lens 112 with heated fluid. The irrigation tip 700 can then be retracted and the aspiration tip 704 be introduced to aspirate the liquified lens and heated fluid.

With the lens 112 removed, an intraocular lens can be introduced into the eye 100. For example, the intraocular lens can be placed into the capsular bag 110. The intraocular lens can be sized to fill the capsular bag, similar to the natural lens.

Figure 21A:
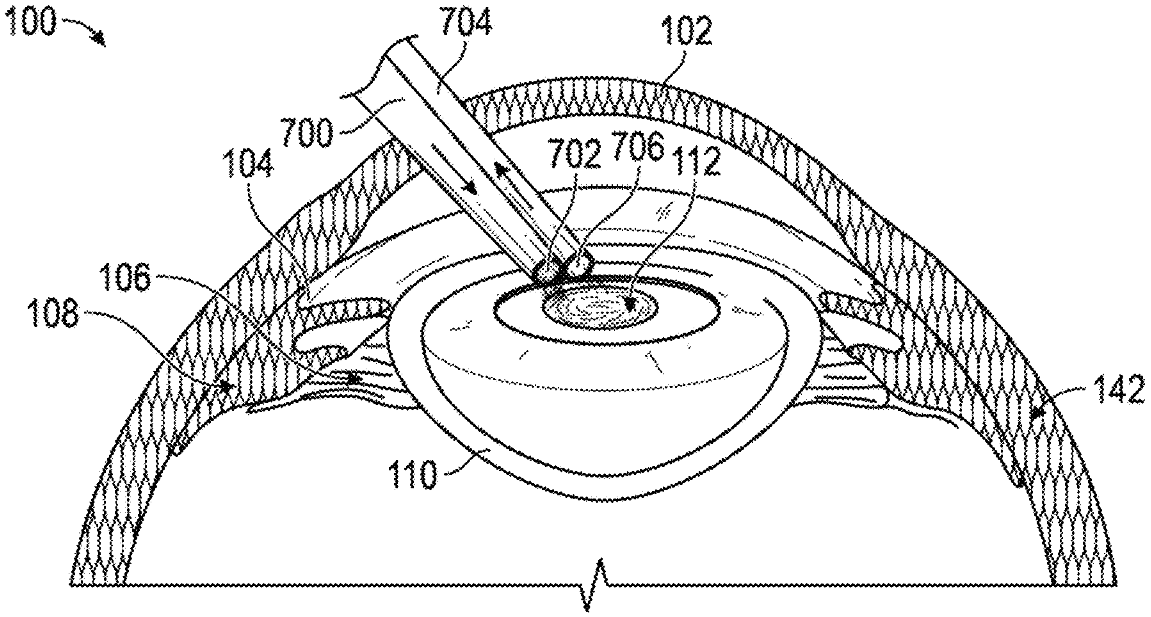
FIGS. 21A-21C illustrate an irrigation tip applying a heated fluid to a crystalline lens of an eye and an aspiration tip aspirating the emulsified crystalline lens. The irrigation and aspiration tips are positioned adjacent to each other and with longitudinal axes thereof parallel to each other.
Figure 21B:
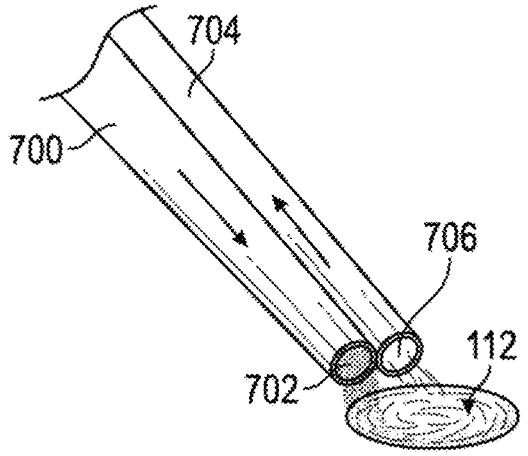
Figure 21C:
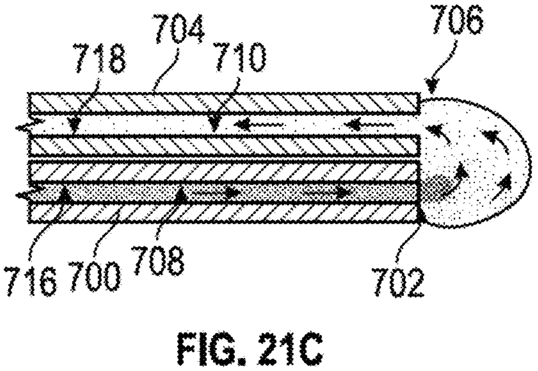

FIGS. 21A-21C illustrate an irrigation and aspiration method using heated fluid to liquify the lens 112. As illustrated in FIG. 21A, a single small microincision can be made in the cornea 102 to provide access into the eye 100. The anterior of the capsular bag 110 can be cut open to access the lens 112. In some variants, a microincision can be made in the anterior of the capsular bag 110 (e.g., off axis) to access the interior of the capsular bag 110, which can avoid Capsulorhexis. In some variants, Capsulorhexis can be performed to penetrate the capsular bag 110 to access the lens 112 therein.

The irrigation tip 700 and the aspiration tip 704 can be introduced into the eye 100 through the microincision in the cornea 102. The irrigation tip 700 and the aspiration tip 704 can advance to the lens 112 through the cut in the anterior of the capsular bag 110. The irrigation tip 700 and the aspiration tip 704 can be juxta positioned. The irrigation tip 700 and the aspiration tip 704 can be positioned parallel relative to each other (e.g., the axes of the irrigation tip 700 and the aspiration tip 704 can be substantially parallel relative to each other). The irrigation tip 700 and the aspiration tip 704 can contact each other along longitudinal sides. The opening 702 of the irrigation tip 700 can be positioned adjacent the opening 706 of the aspiration tip 704. The axes of the opening 702 and the opening 706 can be substantially parallel.

In some variants, the irrigation tip 700 and aspiration tip 704 can be introduced simultaneously. In some variants, the irrigation tip 700 and aspiration tip 704 can be introduced in series. In some variants, the irrigation tip 700 and aspiration tip 704 can be joined together, which can include longitudinal sides being joined together.

As shown in FIG. 21C, the heated fluid 708 can flow through internal lumen 716 and out the opening 702 of the irrigation tip 700 to the lens 112. The lens 112 can be liquified by the heated fluid 708. The heated fluid 708 and liquified lens 112 can be aspirated by the aspiration tip 704. The heated fluid 708 and liquified lens 112 can be aspirated through the opening 706 and into the internal lumen 718 of the aspiration tip 704. The aspirated material 710 can be directed to a waste reservoir. The heated fluid 708 can follow a generally curved flow path (e.g., generally u-shaped) between the opening 702 of the irrigation tip 700 and the opening 706 of the aspiration tip 704. The aspiration tip 704 can quickly aspirate the heated fluid 708 and/or liquified lens 112 to localize the heat from the heated fluid 708. With the lens 112 removed, an intraocular lens can be introduced into the eye 100. For example, the intraocular lens can be placed into the capsular bag 110.

Figure 22A:
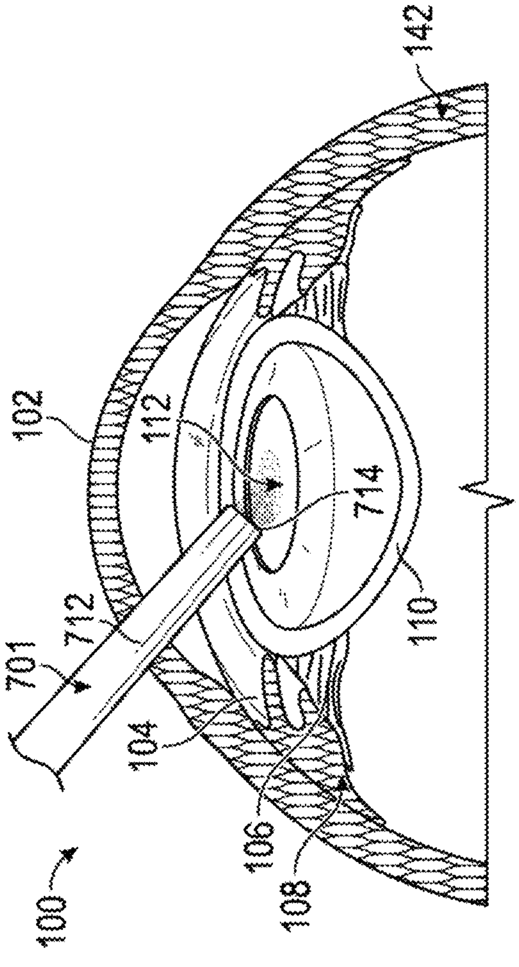
FIGS. 22A-22G illustrate an irrigation tip applying a heated fluid to a crystalline lens of an eye and an aspiration tip aspirating the emulsified crystalline lens. The irrigation and aspiration tips are coaxially positioned.
Figure 22B:
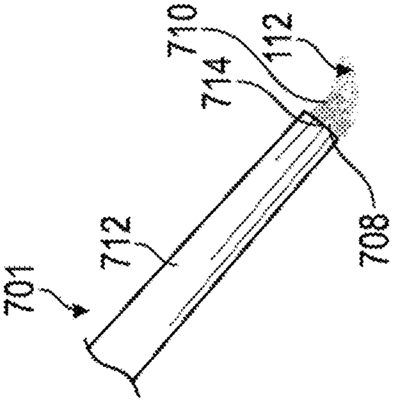

FIGS. 22A-22H illustrate irrigation and aspiration methods using heated fluid to liquify the lens 112. As illustrated in FIG. 22A, a single small microincision can be made in the cornea 102 to provide access into the eye 100. The anterior of the capsular bag 110 can be cut open to access the lens 112. In some variants, a microincision can be made in the anterior of the capsular bag 110 (e.g., off axis) to access the interior of the capsular bag 110, which can avoid Capsulorhexis. In some variants, Capsulorhexis can be performed to penetrate the capsular bag 110 to access the lens 112 therein.

Figure 22C:
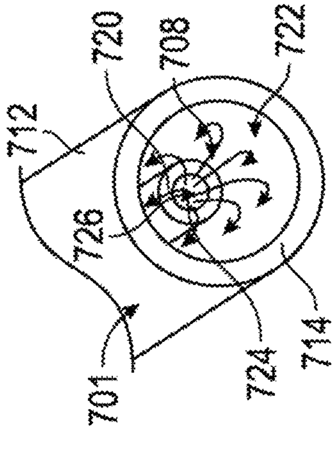

A coaxial system 701 (e.g., coaxial cannulas, coaxial tips) can be advanced into the eye 100 through the incision in the cornea 102. The coaxial system 701 can be advanced to the lens 112 through the incision in the anterior of the capsular bag 110. The coaxial system 701 can include an outer tip 712 (e.g., outer cannula) and an inner tip 720 (e.g., inner cannula). As shown in FIG. 22C, the outer tip 712 and the inner tip 720 can be coaxially positioned. The inner tip 720 can be disposed inside of the outer tip 712 (e.g., the inner tip 720 can be disposed inside an internal lumen 722 of the outer tip 712). In some variants, the outer tip 712 and the inner tip 720 may not be coaxially but can still be arranged with the inner tip 720 inside the outer tip 712.

Figure 22D:
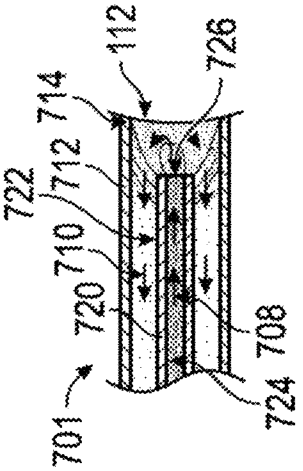

As illustrated in FIGS. 22C and 22D, the inner tip 720 can deliver heated fluid 708 to the lens 112 and the outer tip 712 can aspirate the heated fluid 708 and/or liquified lens 112. As illustrated in FIG. 22D, heated fluid 708 can flow through the internal lumen 724 and out the opening 726 of the inner tip 720 to the lens 112. The opening 726 of the inner tip 720 can be proximal of the opening 714 of the outer tip 712. In some variants, the opening 726 of the inner tip 720 can be at the opening 714 of the outer tip 712. In some variants, the opening 726 of the inner tip 720 can be distal of the opening 714 of the outer tip 712.

The heated fluid 708 can flow out of the opening 714 and to the lens 112 to liquify the lens 112. The outer tip 712 can aspirate (e.g., vacuum, suck) the heated fluid 708 and liquified lens 112 through an internal lumen 722, which can include the space between an outer periphery of the inner tip 720 and an inner wall of the outer tip 712 defining the internal lumen 722. The aspirated material 710 can flow to a waste reservoir. The heated fluid 708 and/or liquified lens 112 can be aspirated through the opening 714 into the internal lumen 722 of the outer tip 712. In some variants, the distal end of the outer tip 712 defining the opening 714 can contact the lens 112.

Figure 22E:
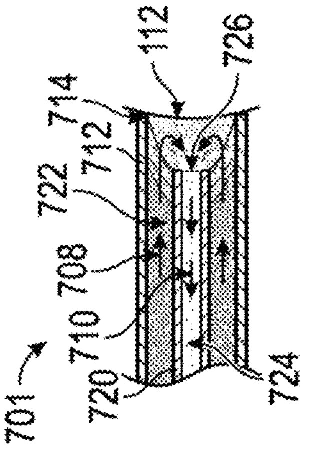

As illustrated in FIG. 22E, in some variants, the outer tip 712 can deliver heated fluid 708 to liquify the lens 112 and the inner tip 720 can aspirate the heated fluid 708 and liquified lens 112. The heated fluid 708 can flow through the internal lumen 722 (e.g., space between the outer periphery of the inner tip 720 and an inner wall of the outer tip 712 defining the internal lumen 722) and out the opening 714 of the inner tip 720 to the lens 112. The inner tip 720 can aspirate the heated fluid 708 and/or liquified lens 112. For example, the heated fluid 708 and/or lens 112 can be aspirated through the opening 726 and into the internal lumen 724 of inner tip 720.

Figure 22H:
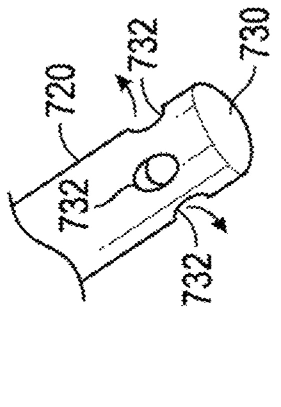
FIG. 22H illustrates a irrigation tip.
Figure 23B:
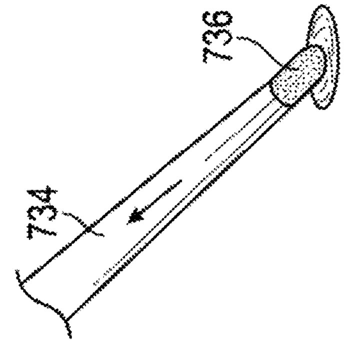
FIGS. 23A-23D illustrate an aspiration tip with heated elements.
Figure 22G:
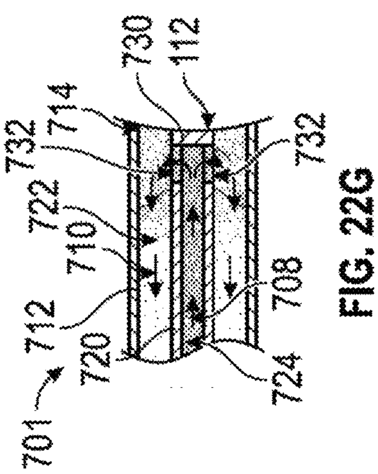
Figure 22F:
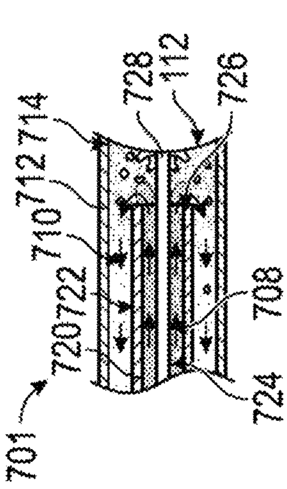

As illustrated in FIG. 22F, in some variants, the coaxial system 701 can include a member 728 (e.g., wire, rigid member, rod). The member 728 can be advanced through the coaxial system 701 to engage the lens 112, which can help to break up the lens 112. The member 728 can be advanced through the inner tip 720 (e.g., internal lumen 724 of the inner tip 720). In some variants, the member 728 can be heated, which may ease penetration of the lens 112 by the member 728. The inner tip 720 can deliver heated fluid 708 to the lens 112, which can heat the member 728. In some variants, the member 728 can be heated by a source other than the heated fluid 708. In some variants, the member 728 can be advanced through the outer tip 712 (e.g., internal lumen 722 of the outer tip 712). In some variants, the member 728 can be used to cut an incision in capsular bag 110 to introduce the coaxial system 701.

As illustrated in FIGS. 22G and 22H, the coaxial system 701 can include an inner tip 720 with a closed distal end 730 (e.g., distal deflection wall). The inner tip 720 can include one or more openings 732 (e.g., apertures) disposed in the side wall of the inner tip 720. The one or more openings 732 can be distributed circumferentially about the axis of the inner tip 720 (e.g., around the side wall). Heated fluid 708 can flow through the internal lumen 724 and out the one or more openings 732 to the lens 112. The heated fluid 708 can flow into the distal end 730, deflect off the distal end 730, and out the one or more openings 732. In some variants, the distal end 730 can contact the lens 112. In some variants, the distal end 730 can be heated by the heated fluid 708 and/or heated by another source, which can enable the distal end 730 to penetrate the lens 112 with the assistance of heat.

Figure 23A:
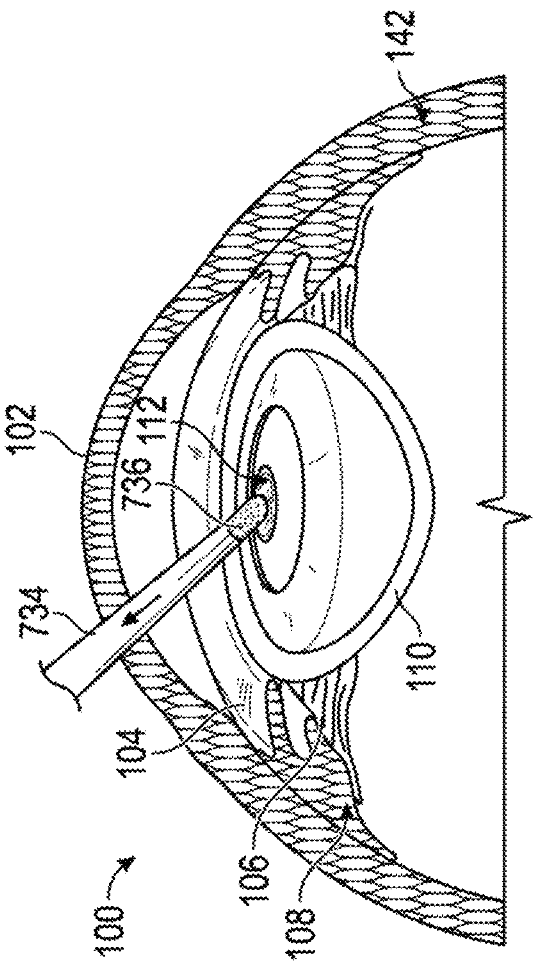

FIGS. 23A-23D illustrate an irrigation and aspiration system and method using heat to liquify the lens 112. As illustrated in FIG. 23A, a single microincision can be made in the cornea 102 to provide access into the eye 100. The anterior of the capsular bag 110 can be cut open to access the lens 112. In some variants, a microincision can be made in the anterior of the capsular bag 110 (e.g., off axis) to access the interior of the capsular bag 110, which can avoid Capsulorhexis. In some variants, Capsulorhexis can be performed to penetrate the capsular bag 110 to access the lens 112 therein.

An aspiration tip 734 (e.g., cannula) can be introduced into the eye 100 through the microincision in the cornea 102. The aspiration tip 734 can be advanced to the lens 112 through the cut in the anterior of the capsular bag 110. The aspiration tip 734 can include a heated element 736 (e.g., heated portion). The heated element 736 can be disposed at a distal end of the aspiration tip 734. For example, as shown in FIG. 23C, the heated element 736 can define the opening 715 into the aspiration tip 734, which can include defining a wall surrounding the internal lumen 738 of the aspiration tip 734. The heated element 736 can be disposed circumferentially about the axis of the internal lumen 738. The heated element 736 can be disposed circumferentially about the internal lumen 738. The heated element 736 can be heated to the temperature ranges described herein (e.g., 64-70 degrees Celsius, 66-70 degrees Celsius, and 68-70 degrees Celsius). The heated element 736 can contact the lens 112 to liquify the lens 112. The liquified lens 112 can be aspirated by the aspiration tip 734 (e.g. aspirated through the opening 715 and into the internal lumen 738 of the aspiration tip 734). The aspirated material 710 can flow to a waste reservoir.

Figure 23D:
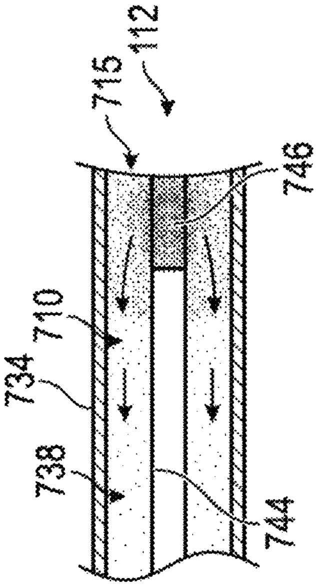
Figure 23C:
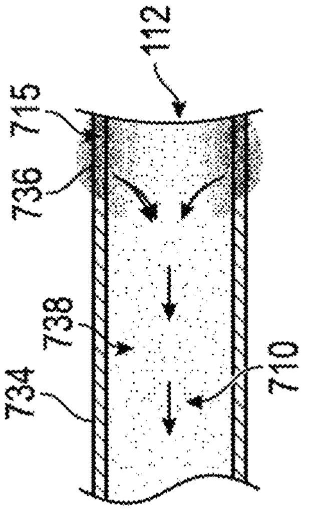

As illustrated in FIG. 23D, in some variants, a member 744 (e.g., wire, rigid member, rod) can be advanced through the aspiration tip 734 (e.g., through the internal lumen 738 of the aspiration tip 734). The member 744 can include a heated element 746 (e.g., heated portion). The heated element 746 can be disposed on a distal end of the member 744. The heated element 746 can be heated to at least the temperature ranges described herein (e.g., 64-70 degrees Celsius, 66-70 degrees Celsius, and 68-70 degrees Celsius). The member 744 can be advanced through the aspiration tip 734 to the lens 112. The heated element 746 can contact the lens 112 to liquify the lens 112. The liquified lens 112 can be aspirated through the aspiration tip 734 (e.g., aspirated through the opening 715 and into the internal lumen 738 of the aspiration tip 734). The aspirated material 710 can flow to a waste reservoir. In some variants, the member 744 can be automatically deployed to a more distal position and/or automatically retracted to a more proximal position, which can be accomplished by way of a biasing mechanism such as a spring. The portions of the member 744 proximal of the heated element 746 can be insulated.

FIGS. 24-29B illustrate various irrigation tips that can be used to liquify the lens 112 with a heated fluid. The irrigation tips can be deployed in a nested cannula system and/or independently inserted into the eye. The irrigation tips can be insulated. The irrigation tips can include flow cross-sections of various shapes (e.g., circular, oval, polygonal, etc.) and/or sizes.

Figure 24:
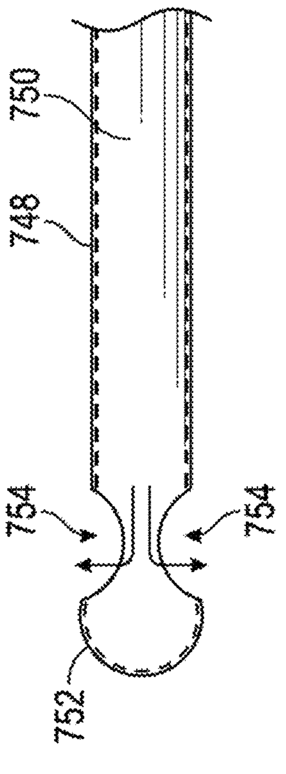

FIG. 24 illustrates an irrigation tip 748 (e.g., cannula). The irrigation tip 748 can include a closed distal end 752, which can be rounded and/or angled. The closed distal end 752 can include an inner wall (e.g., deflection wall), which can be rounded and/or angled. The irrigation tip 748 can include one or more openings 754 (e.g., apertures). The one or more openings 754 can be disposed in the side wall of the irrigation tip 748 that defines an internal lumen 750. The one or more openings 754 can be disposed circumferentially about an axis of the irrigation tip 748 (e.g., axis of the internal lumen 750). The one or more openings 754 can be disposed proximate the distal end 752. The heated fluid can flow distally through the internal lumen 750 and out the one or more openings 754 to the lens 112. The heated fluid can flow distally through the internal lumen 750 to the distal end 752 and be deflected by the distal end 752 out the one or more openings 754 to the lens 112. The one or more openings 754 can be various sizes and/or shapes.

Figure 25A:
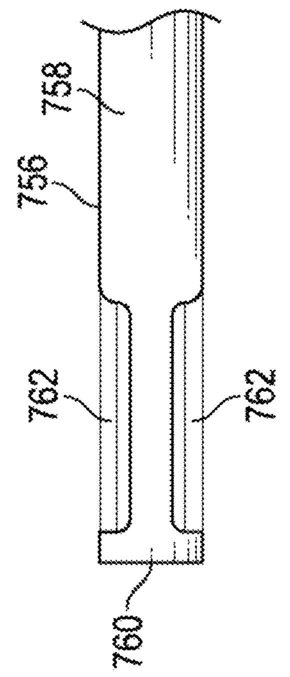
FIGS. 24-29B illustrate irrigation tips (e.g., cannulas).
Figure 25C:
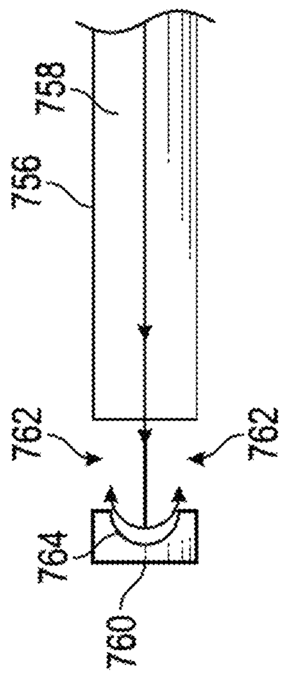
Figure 25B:
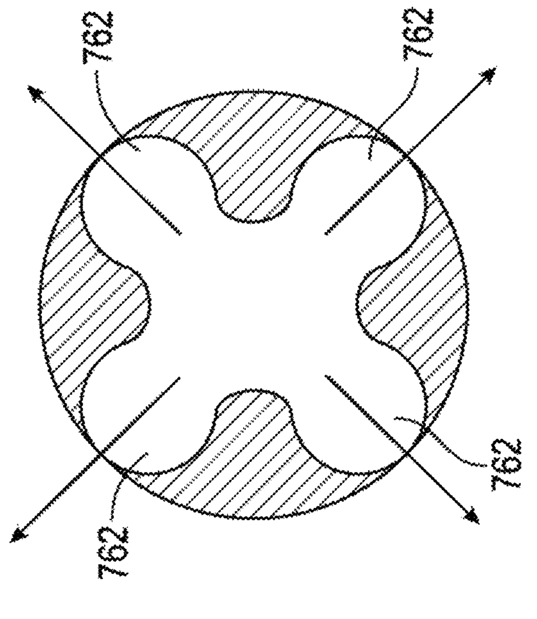

FIGS. 25A-25C illustrate a irrigation tip 756 (e.g., cannula). The irrigation tip 756 can be an open guide tube. The irrigation tip 756 can include a closed distal end 760, which can include a flat outer surface as seen in FIG. 25C (e.g., include a flat surface that is perpendicular to the axis of the irrigation tip 756) and/or a curved inner surface as seen in FIG. 25C. The irrigation tip 756 can include one or more openings 762 (e.g., apertures), such as one, two, three, four, five, six or more. The one or more openings 762 can be disposed in the side wall of the irrigation tip 756 that defines an internal lumen 758. The one or more openings 762 can be disposed circumferentially about an axis of the irrigation tip 756 (e.g., axis of the internal lumen 758). The one or more openings 762 can be disposed proximate the distal end 760. The heated fluid can flow distally through the internal lumen 758 and out the one or more openings 762 to the lens 112. The heated fluid can flow distally through the internal lumen 758 to the closed distal end 760 and be deflected by the closed distal end 760 out the one or more openings 762 to the lens 112. The one or more openings 762 can be various sizes and/or shapes. The one or more openings 762 can be longitudinal.

Figure 26B:
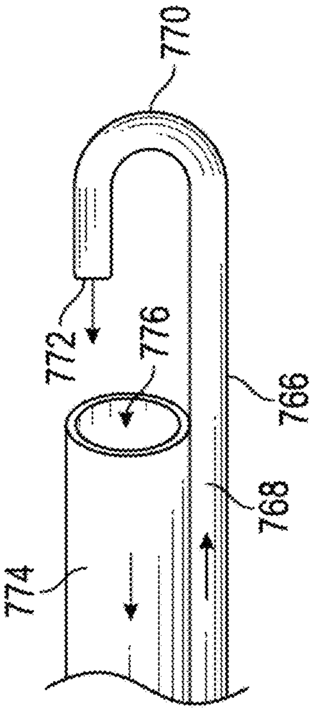
Figure 26A:
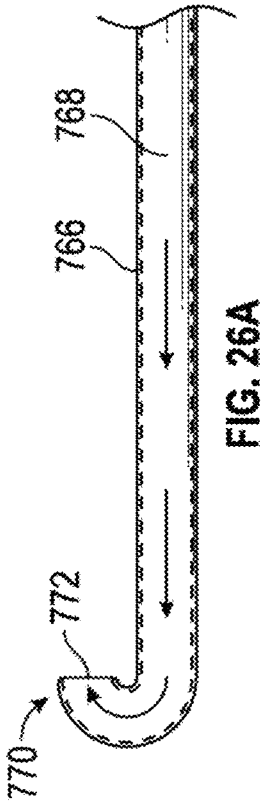

FIGS. 26A and 26B illustrate an irrigation tip 766 (e.g., cannula). The irrigation tip 766 can direct a flow of heated fluid proximally. The irrigation tip 766 can include a curved distal portion 770. The curved distal portion 770 can redirect the flow of the heated fluid from a distal direction to a proximal direction. The heated fluid can flow distally through the internal lumen 768 of the irrigation tip 766 to the curved distal portion 770 that redirects the flow in a proximal direction out of an opening 772 that faces in a proximal direction to the lens 112. As show in FIG. 26B, the opening 772 can face an aspiration tip 774 (e.g., cannula) that can aspirate the heated fluid and/or liquified lens 112. The opening 772 can face an opening 776 of the aspiration tip 774. The opening 772 and the opening 776 can be generally aligned (e.g., coaxially aligned).

Figure 27:
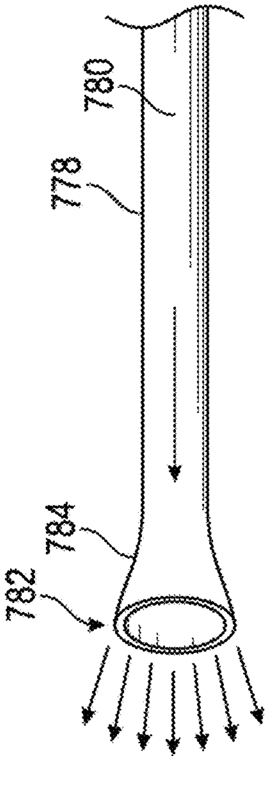

FIG. 27 illustrates an irrigation tip 778 (e.g., cannula). The irrigation tip 778 can include a flared portion 784 (e.g., cone). The flared portion 784 can enlarge (e.g., gradually enlarge) the internal lumen 780 of the irrigation tip 778 in the distal direction until reaching an opening 782. The flared portion 784 can diffuse the heated fluid out of the opening 782. The flared portion 784 can be distally positioned.

Figure 28:
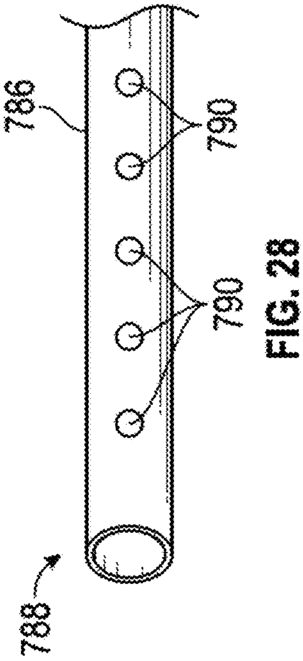

FIG. 28 illustrates an irrigation tip 786 (e.g., cannula). The irrigation tip 786 can include a distal end 788, which can be a cutting distal end. The distal end 788 can be used to cut the lens 112. The irrigation tip 786 can include one or more openings 790 (e.g., apertures, jets). The heated fluid can flow distally through the irrigation tip 786 and out the one or more openings 790. In some variants, the heated fluid can heat the distal end 788 to ease cutting of the lens 112.

Figure 29B:
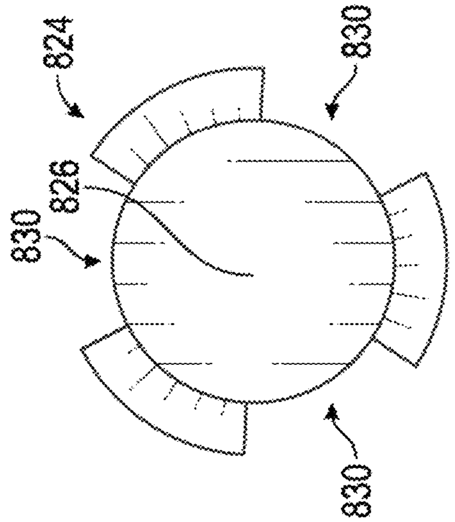
Figure 29A:
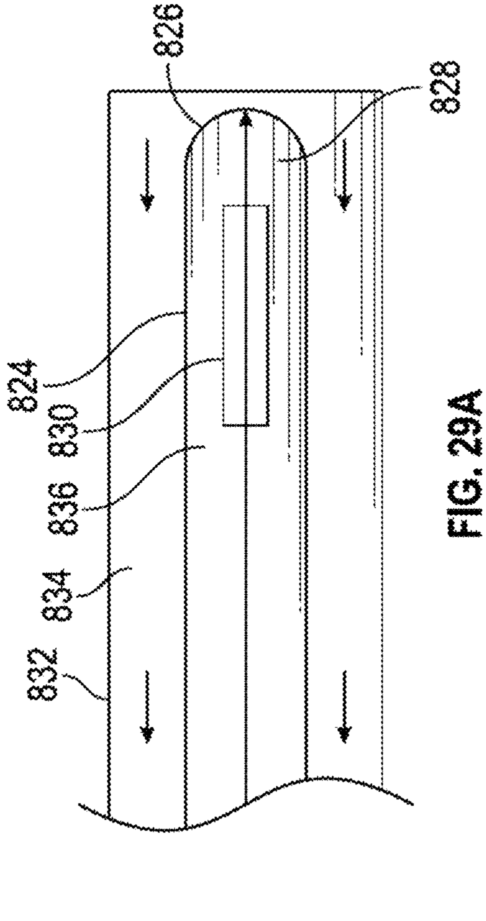

FIGS. 29A and 29B illustrate an irrigation tip 824 (e.g. cannula). As illustrated in FIG. 29A, the irrigation tip 824 can include a closed distal end 826, which can include a flat outer surface (e.g., include a flat surface that is perpendicular to the axis of the irrigation tip 824) and/or a curved inner surface 828. The irrigation tip 824 can include one or more openings 830 (e.g., apertures), such as one, two, three, four, five, six or more. The one or more openings 830 can be disposed in the side wall of the irrigation tip 824 that defines an internal lumen 836. The one or more openings 830 can be disposed circumferentially about an axis of the irrigation tip 824 (e.g., axis of the internal lumen 836). The one or more openings 830 can be disposed proximate the distal end 826. The heated fluid can flow distally through the internal lumen 836 and out the one or more openings 830 to the lens 112. The heated fluid can flow distally through the internal lumen 836 to the closed distal end 826 and be deflected by the curved inner surface 828 out the one or more openings 830 to the lens 112. The one or more openings 830 can be various sizes and/or shapes. The one or more openings 830 can be longitudinal. The irrigation tip 824 can be deployed inside of an aspiration tip 832. For example, the irrigation tip 824 can be advanced distally through an opening 834 of the aspiration tip 832. The irrigation tip 824 can liquify the lens 112 with heated fluid flowed through the one or more openings 830. The aspiration tip 832 can aspirate the heated fluid, liquified lens, and/or other matter through the opening 834 of the aspiration tip 832 for removal.

FIGS. 30-33 illustrate various aspiration tips that can be used to aspirate waste material from the eye, which can include the heated fluid introduced into the eye, liquified lens, aqueous, and/or other matter. The aspiration tips can be deployed in a nested cannula system and/or independently inserted into the eye. The aspiration tips can be insulated. The aspiration tips can include flow cross-sections of various shapes (e.g., circular, oval, polygonal, etc.) and/or sizes.

Figure 30:
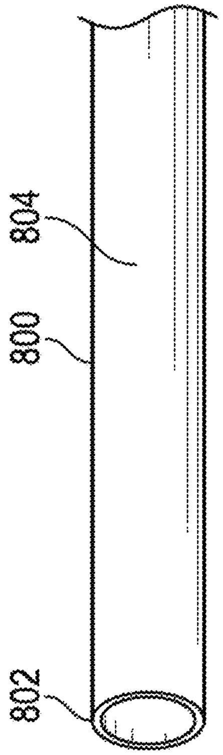

FIG. 30 illustrates an aspiration tip 800 (e.g., cannula). The aspiration tip 800 can include a distal opening 802 through which material can be aspirated into an internal lumen 804 for removal.

Figure 31:
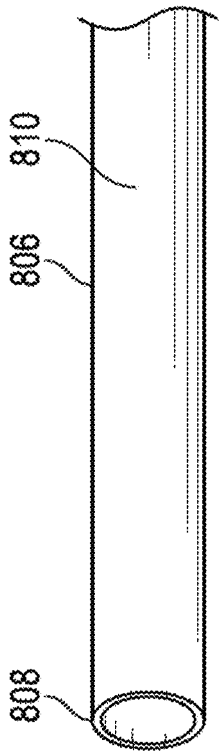
FIGS. 30-33 illustrate aspiration tips (e.g., cannulas).

FIG. 31 illustrates an aspiration tip 806 (e.g., cannula). The aspiration tip 806 can include a distal end 808. The distal end 808 can include an opening. The distal end 808 can include a cutting edge (e.g., blade). The cutting edge can be disposed about the opening of the distal end 808. Matter can be aspirated through the opening of the distal end 808 and into the internal lumen 810.

Figure 32:
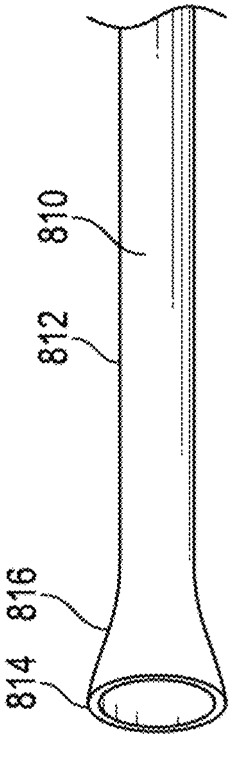

FIG. 32 illustrates an aspiration tip 812 (e.g., cannula). The aspiration tip 812 can include a flared portion 816 (e.g., cone). The flared portion 816 can enlarge (e.g., gradually enlarge) the internal lumen 810 of the aspiration tip 812 in the distal direction until reaching an opening 814, which can provide an enlarged opening 814 for capturing material. The flared portion 816 can be distally positioned. Matter can be aspirated through the opening 814 and into the internal lumen 810.

Figure 33:
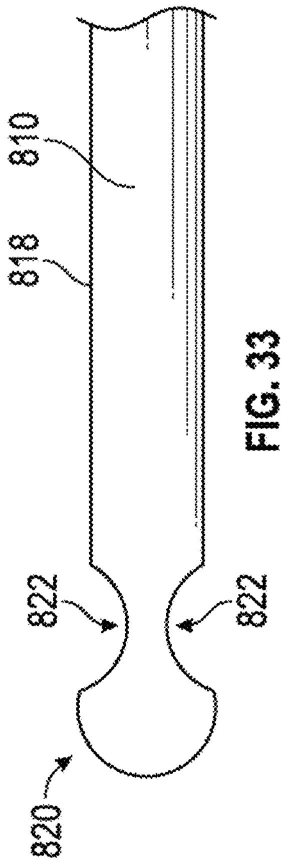

FIG. 33 illustrates an aspiration tip 818 (e.g., cannula). The aspiration tip 818 can include a distal end 820, which can be rounded. The aspiration tip 818 can include one or more openings 822 (e.g., apertures), which can include one, two, three, four or more. The one or more openings 822 can be disposed in the side wall of the aspiration tip 818 defining the internal lumen 810. Matter can be aspirated through the one or more openings 822 and into the internal lumen 810 for removal.

Various further features of the system and methods described herein are detailed below. In some variants, the heated fluid and/or heated elements described herein can be used to cut an incision through the cornea and/or capsular bag to access the lens of the eye. The heating of fluid can be done externally and attached as a module to current irrigation/aspiration setups (e.g., phaco machine). Heating of fluid can be performed in a syringe barrel as a handheld unit can also have an irrigation/aspiration setup. Heating of the fluid can be performed at any location in the systems and methods described herein so long as the temperature of the fluid at the lens is within the ranges described herein. As described herein, temperature sensors (e.g., thermocouples) can be disposed throughout a system and/or in the eye to enable a closed loop system to ensure temperature modulation is controlled. Various sources of heating can be employed to heat the heating elements and/or fluid, which can at least include (electrical, radio-frequency, ultrasound, LASER, microwave, heat gun, immersion heater, chemical reaction, gas, nuclear, and/or others). In some variants, the distal tips and/or body of the irrigation and/or aspiration cannulas described herein can be insulated. The heated fluid can be introduced into the lens by way of a variety of techniques, which at least can include starting at the cortex/nucleus of the lens to dissipate/emulsify from the inside out, use injection as a method to break up the lens into pieces/fragments, or start from the periphery to dig into the lens and aspirate/extract. In some variants, the irrigation cannula can be inserted into the core of the lens and then irrigate heated fluid to emulsify from the core out. The systems and methods can enable surgeons to use microincisions into the capsular bag, which could preserve the bag and/or zonules of the eye. Localized heating by way of convection (e.g., heated fluid) can enable emulsification of the lens 112 (e.g., cataract proteins) without disturbing nearby tissue. The methods of removing the lens described herein with heated elements and/or heated fluid can be performed in a few seconds to less than one minute while preserving the capsular bag and zonules. In some variants, the systems herein can include a handpiece that is either independent or controls by way of the phaco handpiece/heater setup. The irrigation described herein can be low pressure to reduce excess heat transfer into tissue. The system and methods described herein can be used in a robotic surgery.

Figure 33A:
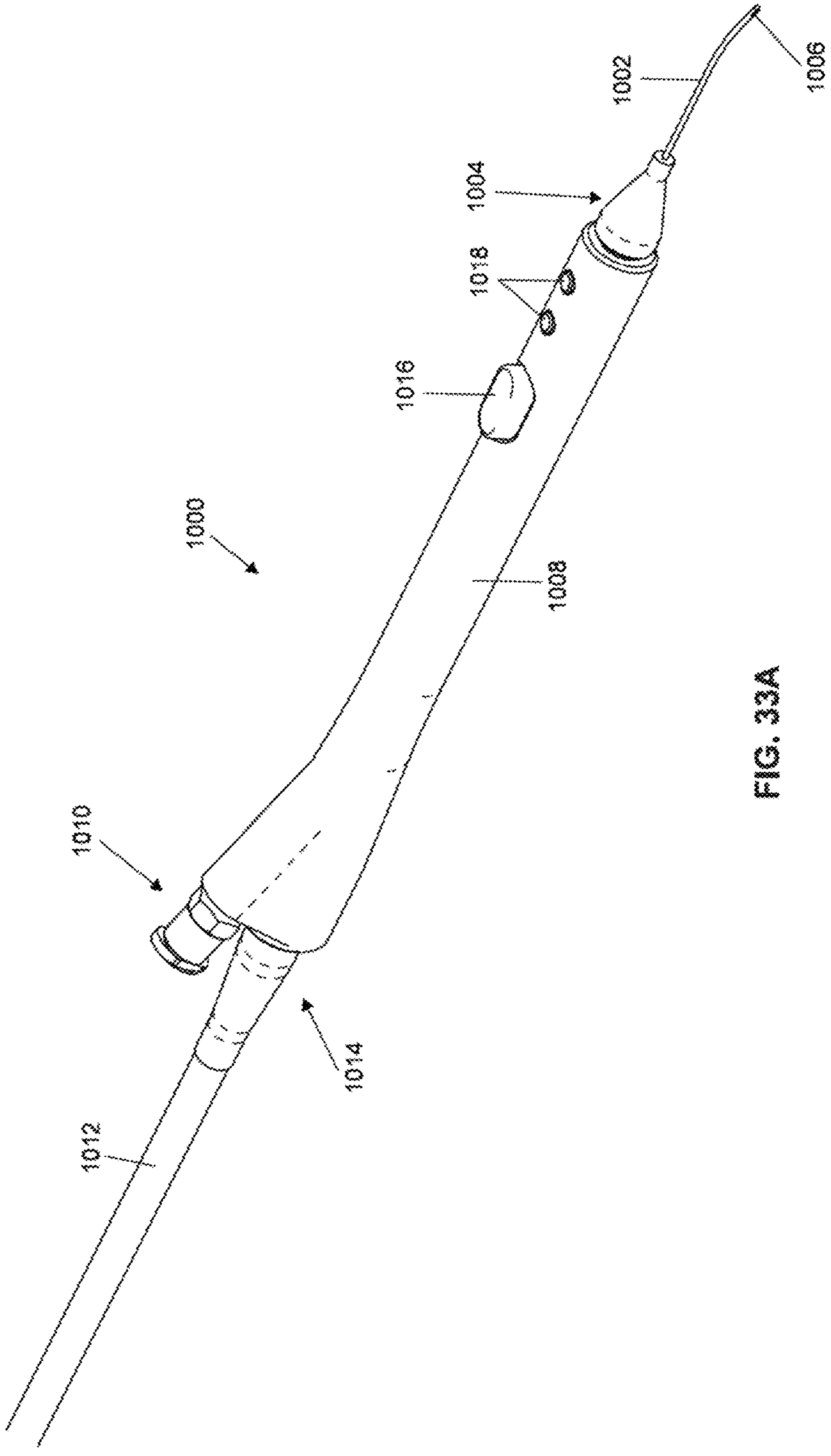
FIGS. 33A and 33B illustrate an irrigation handpiece.
Figure 33B:
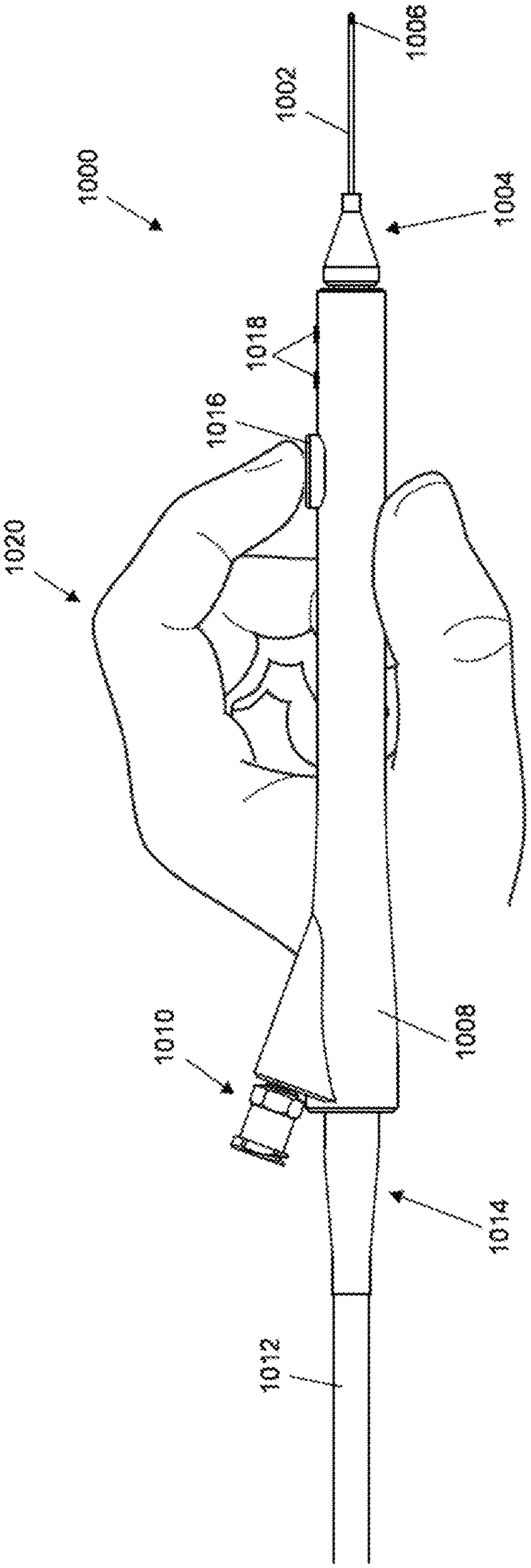

FIGS. 33A and 33B illustrate an irrigation handpiece 1000, which can also be referred to as an irrigation device and/or irrigation tool. The irrigation handpiece 1000 can be held by a clinician's hand 1020 and/or manipulated by or incorporated into a robot to deliver heated fluid to the lens 112 of the eye 100.

The irrigation handpiece 1000 can include a port 1010 (e.g., inlet) through which fluid (e.g., saline solution) can be delivered to the irrigation handpiece 1000. In some variants, heated fluid can be delivered to the irrigation handpiece 1000. In some variants, fluid can be delivered to the irrigation handpiece 1000 and the irrigation handpiece 1000 can heat the fluid prior to delivery in the eye. The port 1010 can be disposed on a proximal portion of the irrigation handpiece 1000. The port 1010 can be fluidically coupled to a reservoir (e.g., container, bag, IV bag, vessel, etc.) of fluid (e.g., saline solution).

The irrigation handpiece 1000 can include an irrigation tube 1002 (e.g., tube, cannula, needle). The irrigation tube 1002 can be inserted through the cornea 102 and into the capsular bag 110 to direct heated fluid at the lens 112. The irrigation tube 1002 can be elongate. The irrigation tube 1002 can include a curved portion. For example, the irrigation tube 1002 can include a proximal portion that is straight and then curve to a distal portion that is angled relative to the proximal portion. The irrigation tube 1002 can include a distal portion that is angled relative to a proximal portion. The irrigation tube 1002 can be a variety of sizes (e.g., diameters), which can at least include 0.1-3.0 millimeters, 1.0-2.5 millimeters, or less than 2.0 millimeters. The irrigation tube 1002 can be disposed on a distal portion of the irrigation handpiece 1000.

The irrigation tube 1002 can include one or more outlets 1006 (e.g., openings, holes), which can at least include one, two, three, four or more outlets 1006. The one or more outlets 1006 can be disposed at a distal portion of the irrigation tube 1002. The one or more outlets 1006 can be disposed through a peripheral wall of the irrigation tube 1002. For example, in some variants, a distal end of the irrigation tube 1002 can be closed and two outlets 1006 can be disposed in the peripheral wall of the irrigation tube 1002, which can include the two outlets 1006 being disposed at about one hundred and eighty degrees apart from each other. Fluid received through the port 1010 of the irrigation handpiece 1000 can flow out of the irrigation tube 1002 by way of the one or more outlets 1006.

The irrigation handpiece 1000 can include a distal portion 1004 (e.g., end portion, distal piece, end piece, connector, tips, distal tips). The irrigation tube 1002 can be coupled to the distal portion 1004. The distal portion 1004 can include a conical shape. The distal portion 1004 can be coupled to a body 1008 (e.g., housing) of the irrigation handpiece 1000, which can include being removably coupled to the body 1008. In some variants, the distal portion 1004 can be a disposable component (e.g., disposable end piece) that is replaced between surgeries. In some variants, the irrigation handpiece 1000 can be disposable and replaced between surgeries. The body 1008 can be ergonomically designed to be held by a hand 1020. The body 1008 can house one or more features of the irrigation handpiece 1000, which can at least include one or more heaters (e.g., heating devices), fluid lines (e.g., tubes, lumens, hoses, etc.) to direct a flow of fluid received through the port 1010, valves, conduits (e.g., wires), processors, controllers, power interfaces, batteries, memories, wireless communication data interfaces, wired communication data interfaces, user interfaces (e.g., displays, speakers, microphones, buttons, toggles, switches, dials, sliders, etc.), indicators (e.g., lights, speakers, etc.), etc.

The irrigation handpiece 1000 can include an interface 1014 (e.g., port, connector) to couple with a cable 1012. The cable 1012 can provide electrical power to the irrigation handpiece 1000. Electrical power can be provided to the irrigation handpiece 1000 from a console (e.g., power source, computing device) by way of the cable 1012. The cable 1012 can communicate data, which can include temperature data, flow rate data, instructions, etc., between the irrigation handpiece 1000 and the console. In some variants, data can be communicated wirelessly between the irrigation handpiece 1000 and the console.

The irrigation handpiece 1000 can include a user interface 1016 (e.g., toggle, switch, button, dial, slider, etc.). The user interface 1016 can be used to control the flow of heated fluid out of the irrigation tube 1002. In some variants, the user interface 1016 can be manipulated to stop or start the flow of heated fluid out of the irrigation tube 1002. In some variants, as a default, fluid may flow out of the irrigation tube 1002 to maintain pressure in the capsular bag 110 during cataract surgery but, upon interacting with the user interface 1016 (e.g., interacting with, pushing, pulling, and/or switching the user interface 1016), heated fluid may flow out of the irrigation tube 1002 to emulsify the lens 112. In some variants, the user interface 1016 can be manipulated to adjust a temperature of the heated fluid.

The irrigation handpiece 1000 can include one or more indicators 1018 (e.g., lights, speakers, displays, etc.). The one or more indicators 1018 can indicate a status of the irrigation handpiece 1000. For example, the one or more indicators 1018 can indicate when the irrigation handpiece 1000 is receiving electrical power. The one or more indicators 1018 can indicate when fluid heated to emulsify the lens 112 is flowing out of the irrigation tube 1002 and/or when it is not. In some variants, the one or more indicators 1018 can indicate when a temperature at the irrigation tube 1002 is above or below a threshold.

The irrigation handpiece 1000 can include any feature of any other irrigation device, aspiration device, thermal device, and/or other device or system described herein. In some variants, the irrigation handpiece 1000 can aspirate as well.

Figure 34A:
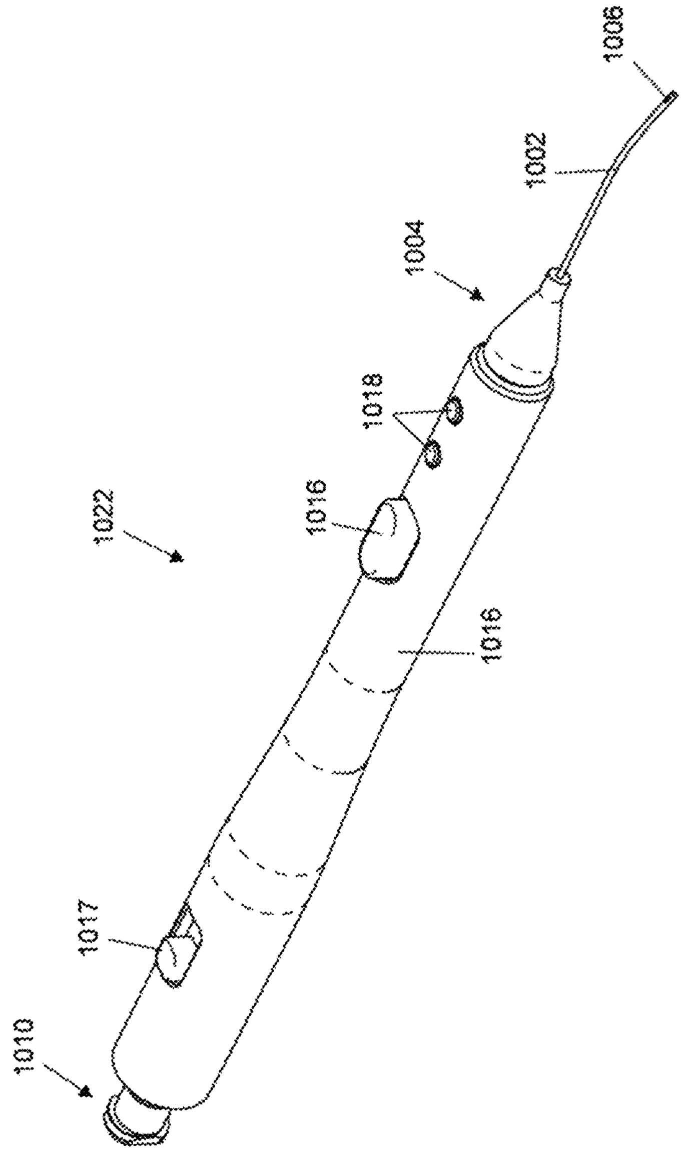
FIGS. 34A and 34B illustrate an irrigation handpiece.
Figure 34B:
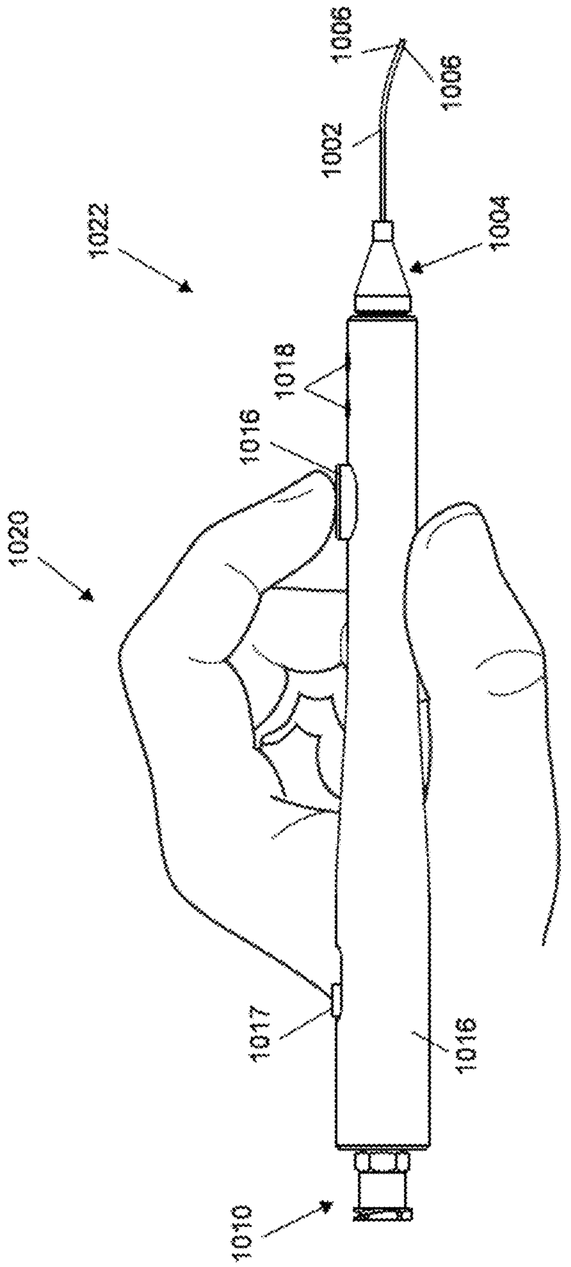

FIGS. 34A and 34B illustrate an irrigation handpiece 1022, which can include the features of irrigation handpiece 1000. The irrigation handpiece 1022 can be powered by a battery (e.g., disposable battery, rechargeable battery) as opposed to an external power source as irrigation handpiece 1000. Accordingly, the irrigation handpiece 1022 may not have the interface 1014 to connect the cable 1012.

The irrigation handpiece 1022 can include an user interface 1017 (e.g., toggle, switch, button, dial, slider, etc.). The user interface 1017 can be used to turn the irrigation handpiece 1022 on and off (e.g., activate the irrigation handpiece 1022).

Figure 35A:
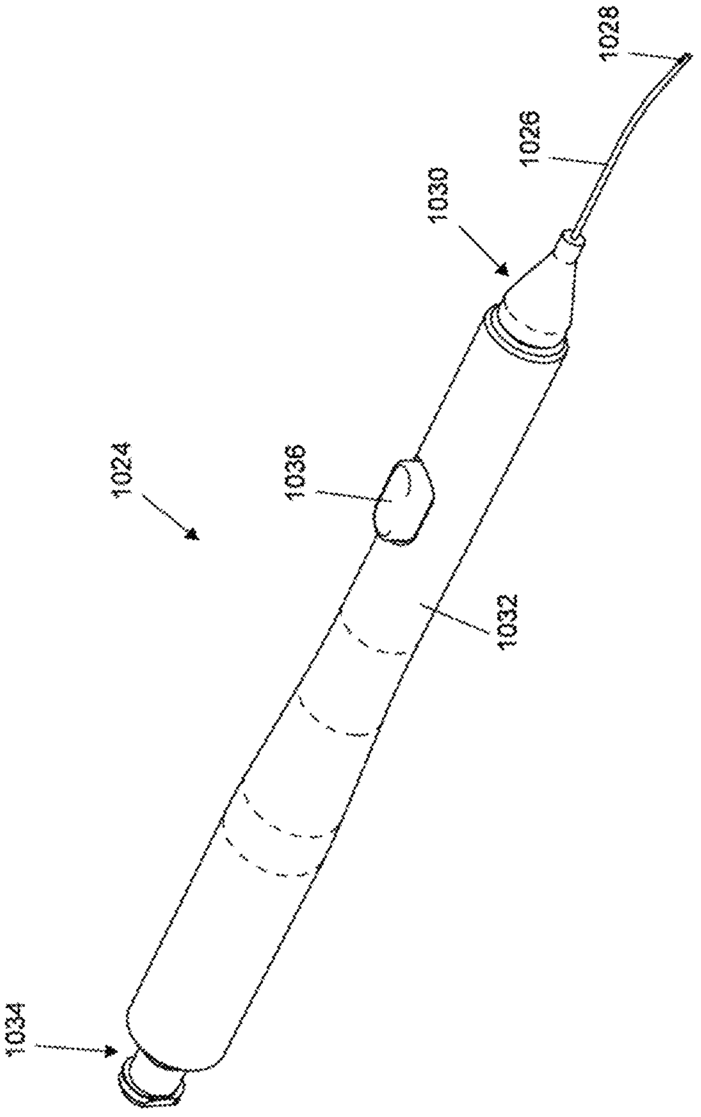
FIGS. 35A and 35B illustrate an aspiration handpiece.
Figure 35B:
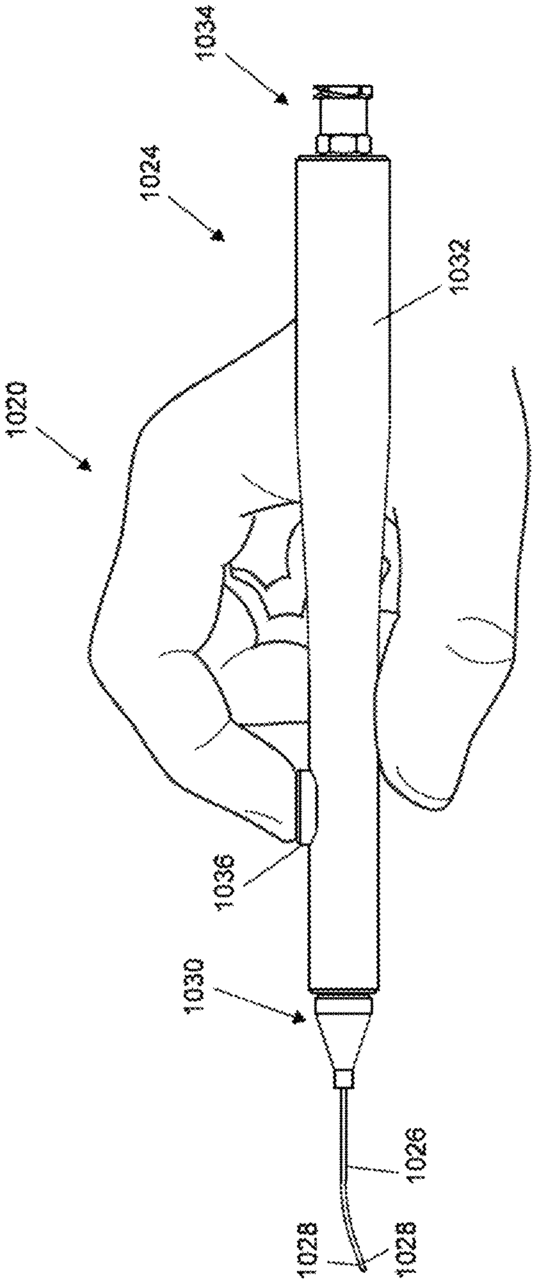

FIGS. 35A and 35B illustrate an aspiration handpiece 1024, which can also be referred to as an aspiration device and/or aspiration tool. The aspiration handpiece 1024 can be held by a clinician's hand 1020 and/or manipulated by or incorporated into a robot to aspirate material, such as fluid, heated fluid, and/or emulsified lens 112, from the capsular bag 110.

The aspiration handpiece 1024 can include a port 1034 (e.g., outlet) through which fluid, heated fluid, and/or emulsified lens 112 can leave (e.g., be aspirated out of) the irrigation handpiece 1000. The port 1034 can be disposed on a proximal portion of the aspiration handpiece 1024. A vacuum can aspirate material out of the aspiration handpiece 1024 by way of the port 1034. The port 1034 can be fluidically coupled to a container, such as a vacuum canister (e.g., separator). The port 1034 can be fluidically coupled to a wall vacuum.

The aspiration handpiece 1024 can include an aspiration tube 1026 (e.g., tube, cannula, needle). The aspiration tube 1026 can be inserted through the cornea 102 and into the capsular bag 110 to aspirate material such as fluid, heated fluid, and/or emulsified lens 112. The aspiration tube 1026 can be elongate. The aspiration tube 1026 can include a curved portion. For example, the aspiration tube 1026 can include a proximal portion that is straight and then curve to a distal portion that is angled relative to the proximal portion. The aspiration tube 1026 can include a distal portion that is angled relative to a proximal portion. The aspiration tube 1026 can be a variety of sizes (e.g., diameters), which can at least include 0.1-3.0 millimeters, 1.0-2.5 millimeters, or less than 2.0 millimeters. The aspiration tube 1026 can be disposed on a distal portion of the aspiration handpiece 1024.

The aspiration tube 1026 can include one or more inlets 1028 (e.g., openings, holes), which can at least include one, two, three, four or more inlets 1028. The one or more inlets 1028 can be disposed at a distal portion of the aspiration tube 1026. The one or more inlets 1028 can be disposed through a peripheral wall of the aspiration tube 1026. For example, in some variants, a distal end of the aspiration tube 1026 can be closed and two inlets 1028 can be disposed in the peripheral wall of the aspiration tube 1026, which can include the two inlets 1028 being disposed at about one hundred and eighty degrees apart from each other. Material aspirated through the one or more inlets 1028 can flow out (e.g., be aspirated out of) of the aspiration handpiece 1024 by way of the port 1034.

The aspiration handpiece 1024 can include a distal portion 1030 (e.g., end portion, distal piece, end piece, connector, tips, distal tips). The aspiration tube 1026 can be coupled to the distal portion 1030. The distal portion 1030 can include a conical shape. The distal portion 1030 can be coupled to a body 1032 (e.g., housing) of the aspiration handpiece 1024, which can include being removably coupled to the body 1032. In some variants, the distal portion 1030 can be a disposable component (e.g., disposable end piece) that is replaced between surgeries. In some variants, the body 1032 can be ergonomically designed to be held by a hand 1020. The body 1032 can house one or more features of the aspiration handpiece 1024, which can at least include one or more valves, fluid lines (e.g., tubes, lumens, hoses, etc.), conduits (e.g., wires), processors, controllers, power interfaces, batteries, memories, wireless communication data interfaces, wired communication data interfaces, user interfaces (e.g., displays, speakers, microphones, buttons, toggles, switches, dials, sliders, etc.), indicators (e.g., lights, speakers, etc.), etc.

The aspiration handpiece 1024 can include a user interface 1036 (e.g., toggle, switch, button, dial, slider, etc.). The user interface 1036 can be used to control aspiration by the aspiration handpiece 1024. In some variants, the user interface 1036 can be manipulated to stop or start aspiration. In some variants, the user interface 1036 can be manipulated (e.g., interacted with, pushed, pulled, and/or switched) to adjust aspiration (e.g., increase or decrease flow rates, pressure, etc.).

In some variants, the aspiration handpiece 1024 can include one or more indicators (e.g., lights, speakers, displays, etc.). The one or more indicators can indicate a status of the aspiration handpiece 1024, which can include a blocked status. For example, the one or more indicators can indicate when the aspiration handpiece 1024 is in a configuration for aspirating (e.g., a valve is open). The one or more indicators can indicate when a temperature at the aspiration tube 1026 is above or below a temperature threshold.

Figure 36A:
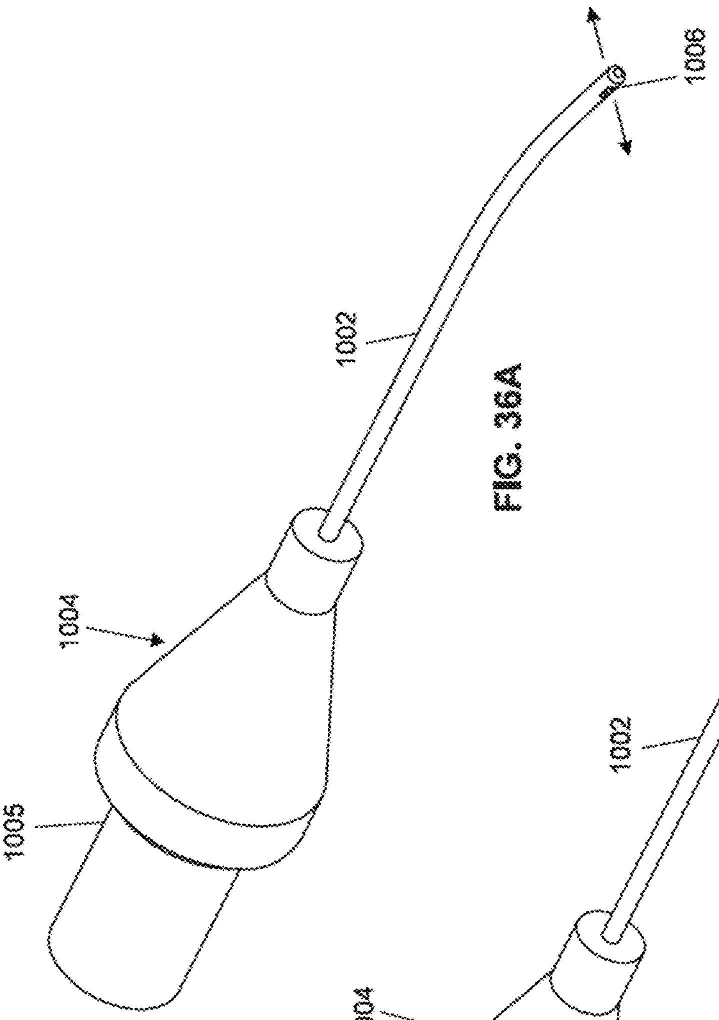
FIGS. 36A and 36B illustrate tips for irrigation and/or aspiration handpieces.
Figure 36B:
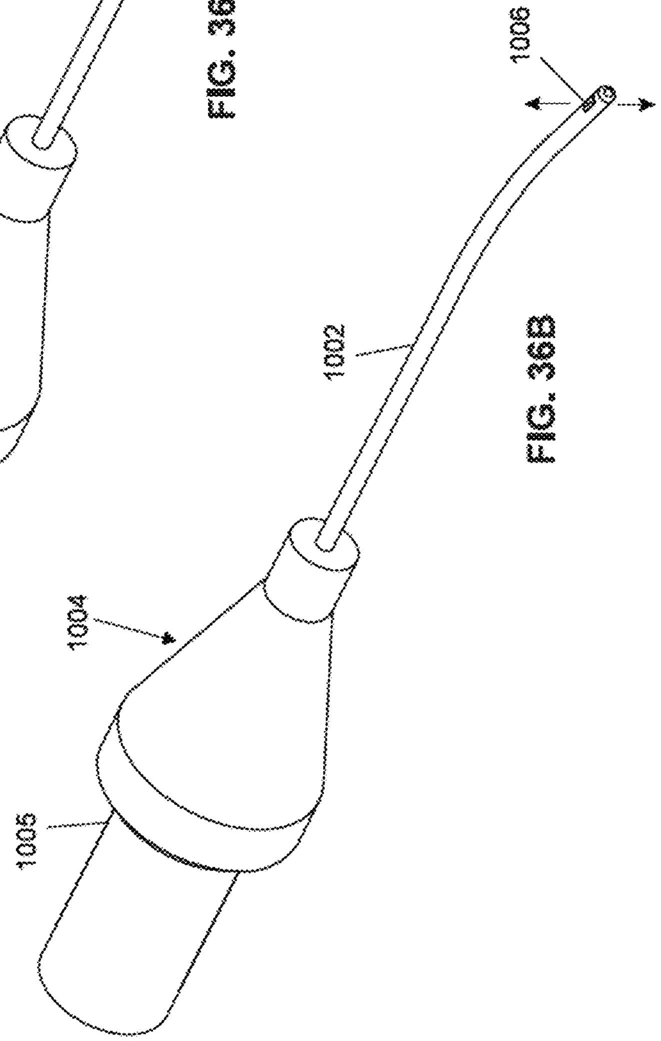

FIGS. 36A and 36B illustrates distal portions 1004 of an irrigation handpiece, which can be the same as the distal portion 1030 of an aspiration handpiece. As described herein, the distal portion 1004 can be coupled (e.g., removably coupled) with an irrigation handpiece. The distal portion 1004 can include a proximal portion 1005 that can be disposed within the irrigation handpiece to facilitate coupling. In some variants, the proximal portion 1005 can be coupled to the irrigation handpiece using a variety of techniques, which can at least include a threaded connection, press fit, fastener connection (e.g., bolt(s), pin(s), latch(es), etc.), spring(s), and/or other techniques. The irrigation tube 1002 coupled to the distal portion 1004 can include one or more outlets 1006 (e.g., two outlets 1006). The outlets 1006 can, as illustrated, be arranged through the peripheral wall of the irrigation tube 1002. The outlets 1006 can be disposed on opposing sides of the irrigation tube 1002 (e.g., one hundred and eighty degrees apart). The aspiration tube 1026 and one or more inlets 1028 can be similarly arranged. As described herein, the distal portion 1004 and/or distal portion 1030 can be disposable (e.g., replaced between surgeries).

Figure 37:
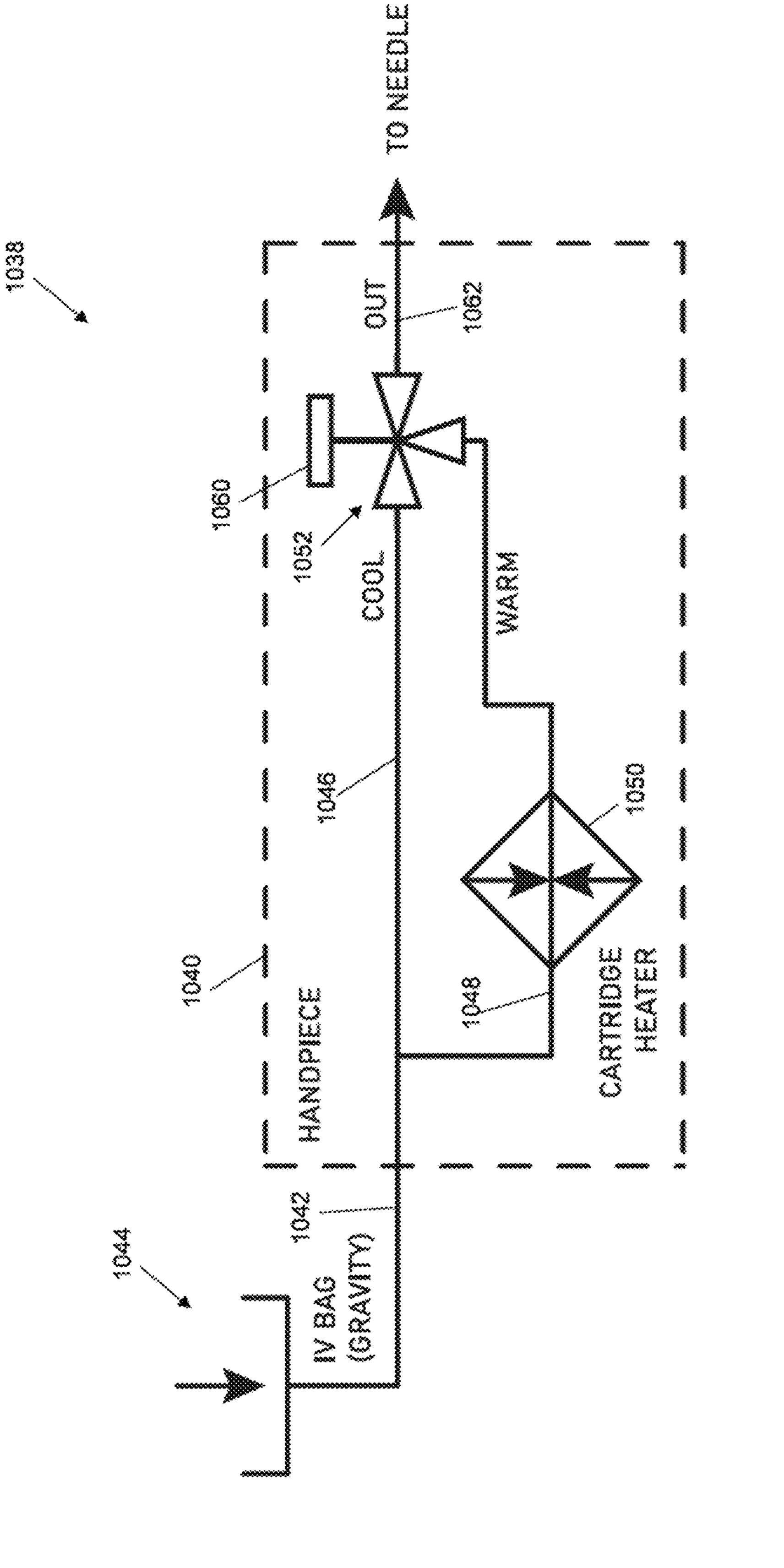
FIG. 37 illustrates a schematic of an irrigation system.

FIG. 37 illustrates a schematic of an irrigation system 1038. The irrigation system 1038 can include an irrigation handpiece 1040, which can at least be irrigation handpiece 1000 and irrigation handpiece 1022 and/or include any of the features thereof.

As shown, a reservoir 1044 (e.g., container, bag, IV bag, vessel, etc.) can supply fluid (e.g., saline solution) to the irrigation handpiece 1040. An inlet line 1042 (e.g., inlet tubing, conduit, hose) can direct a flow of fluid from the reservoir 1044 to the irrigation handpiece 1040. In some variants, one or more valves can be disposed at the outlet of the reservoir 1044 and/or along the inlet line 1042 to selectively stop a flow of fluid to the irrigation handpiece 1040. In some variants, one or more flow regulators, which can be adjustable (e.g., automatically adjustable) can be disposed at the outlet of the reservoir 1044 and/or along the inlet line 1042 to adjust a flow of fluid to the irrigation handpiece 1040.

The inlet line 1042 can split into a first fluid line 1046 (e.g., tubing, conduit, hose) and second fluid line 1048 (e.g., tubing, conduit, hose). The split can be outside or inside the body of the irrigation handpiece 1040. The first fluid line 1046 can direct fluid from the reservoir 1044 to a valve 1052. The second fluid line 1048 can direct fluid from the reservoir 1044 to a heater 1050 (e.g., heating device, cartridge heater, electrode, heated element) and then to the valve 1052. The heater 1050 can heat the fluid to at least the temperatures described herein (e.g., values between 64-70 degrees Celsius). The heater 1050 can heat the fluid to a precise temperature regardless of the inflow temperature. In some variants, the heater 1050 can heat the fluid above temperatures described herein to accommodate for heat loss prior to delivery at the lens 112 such that the heated fluid, when delivered at the lens 112, is at the temperatures described herein (e.g., values between 64-70 degrees Celsius).

In some variants, the valve 1052 can alternate between permitting a flow through the first fluid line 1046 while stopping a flow through the second fluid line 1048 and permitting a flow through the second fluid line 1048 while stopping a flow through the first fluid line 1046. For example, the irrigation handpiece 1040 can include an user interface 1060 (e.g., toggle, switch, button, dial, slider, etc.) that can be interacted with (e.g., pushed, pulled, pressed, rotated, etc.) to reconfigure the valve 1052 to permit or stop flow through the first fluid line 1046 and second fluid line 1048. For example, a surgeon performing cataract surgery using the irrigation handpiece 1040 can interact with the user interface 1060 to configure the valve 1052 to stop flow through the first fluid line 1046 and permit flow through the second fluid line 1048 to direct heated fluid through the outlet line 1062 to the irrigation tube for delivery to the lens 112. In some variants, the valve 1052 can be manipulated (e.g., actuated) to stop the flow of fluid through the first fluid line 1046, permit the flow of fluid through the first fluid line 1046, stop the flow of fluid through the second fluid line 1048, and/or permit the flow of fluid through the second fluid line 1048.

When the valve 1052 is configured to permit flow through the first fluid line 1046 while stopping flow through the second fluid line 1048, fluid from the reservoir 1044 can flow through the first fluid line 1046 to an outlet line 1062 (e.g., tubing, conduit, hose) of the irrigation handpiece 1040 without being routed to the heater 1050 (e.g., without being heated) to be delivered within the capsular bag 110 by way of an irrigation tube of the irrigation handpiece 1040, which can enable the irrigation system 1038 to perform irrigation without heated fluid. When the valve 1052 is configured to stop flow through the first fluid line 1046 while permitting flow through the second fluid line 1048, fluid from the reservoir 1044 can flow through the second fluid line 1048 to the heater 1050 for heating and to the outlet line 1062 to be delivered to the lens 112 within the capsular bag 110 by way of an irrigation tube of the irrigation handpiece 1040, which can enable the irrigation system 1038 to emulsify the lens 112 for aspiration. The heater 1050 can adjust (e.g., increase, decrease) energy transferred to the fluid in the second fluid line 1048 to alter the temperature of the fluid. The heater 1050 can adjust energy transferred to the fluid in the second fluid line 1048 based on a sensed temperature at the irrigation tube of the irrigation handpiece 1040 and/or other location. For example, if the sensed temperature at the irrigation tube is above a threshold, the heater 1050 can decrease energy transferred to the fluid. If the sensed temperature at the irrigation tube is below a threshold, the heater 1050 can increase energy transferred to the fluid.

Figure 38:
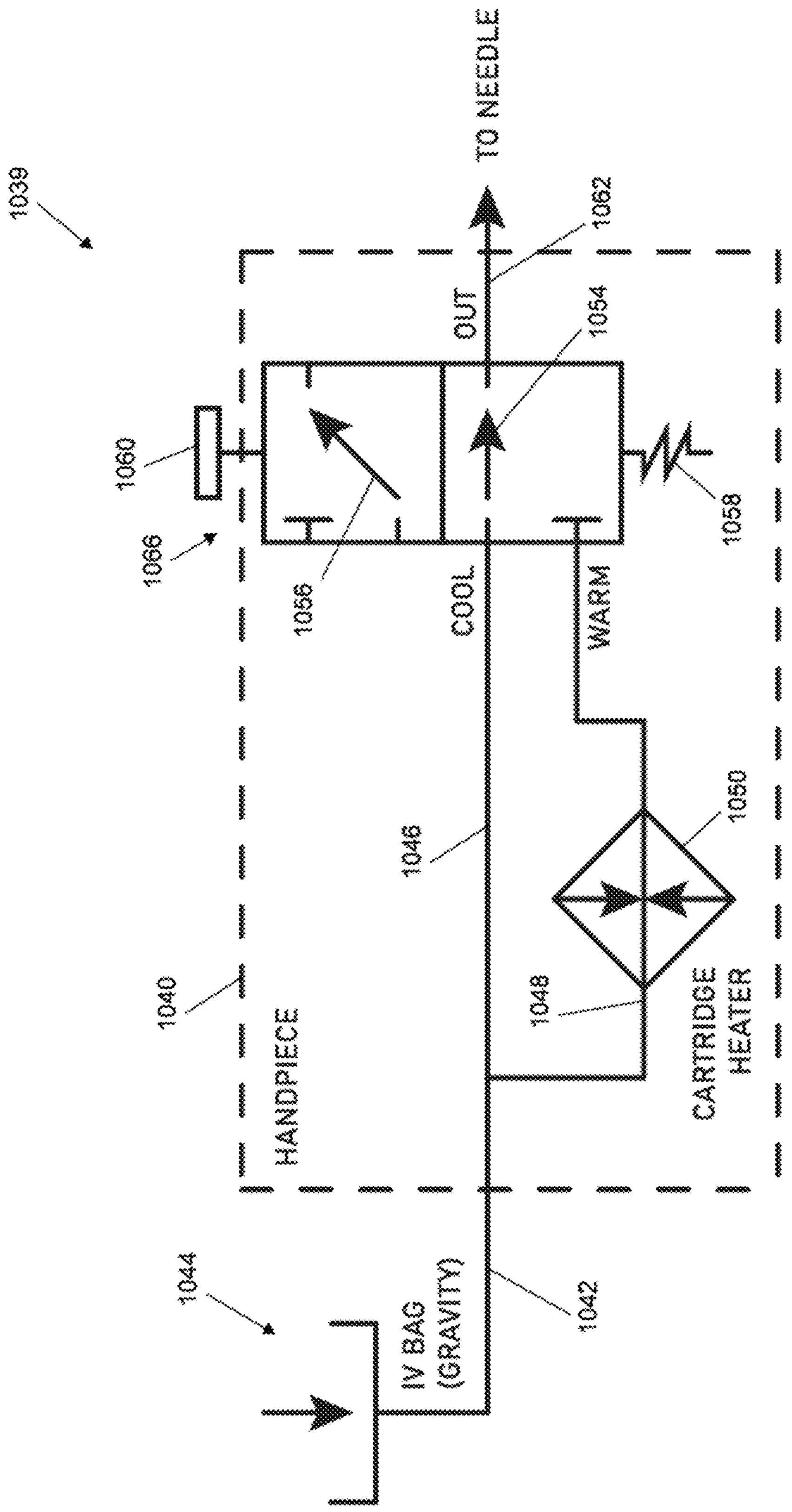
FIG. 38 illustrates a schematic of an irrigation system.
Figure 39:
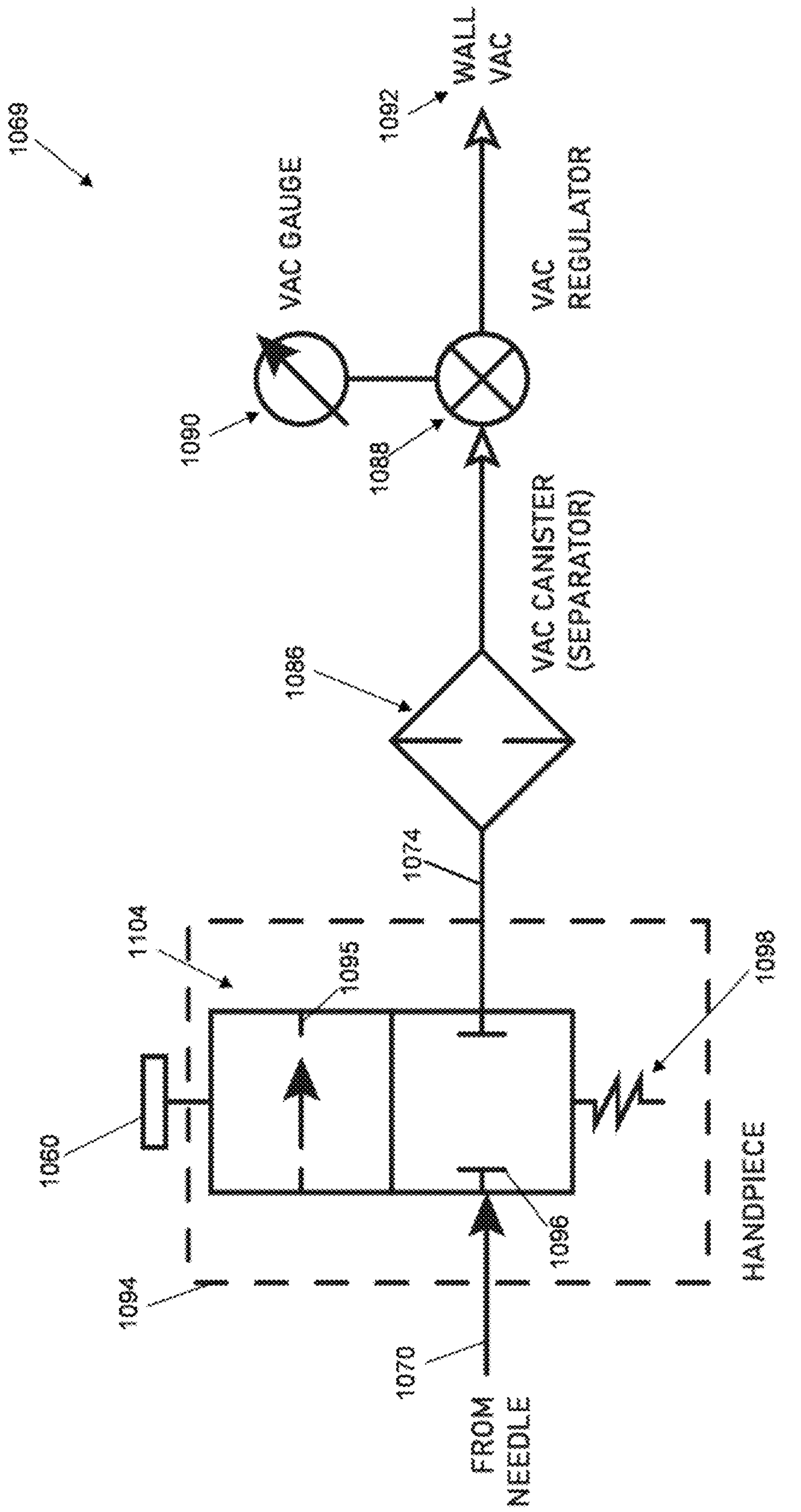
FIG. 39 illustrates a schematic of an aspiration system.

FIG. 38 illustrates an irrigation system 1039, which can include the features of irrigation system 1038. The irrigation system 1039 can include a spring valve 1066 that can control the flow of fluid through the first fluid line 1046 and the second fluid line 1048. The spring valve 1066 can include a first fluid opening 1054 (e.g., flow path) and a second fluid opening 1056 (e.g., flow path). The spring valve 1066 can include a spring 1058 (e.g., resilient member). The spring 1058 can bias the spring valve 1066 (e.g., be the default configuration of the spring valve 1066) such that the first fluid opening 1054 is positioned (e.g., positioned at the first fluid line 1046) to permit fluid flowing through the first fluid line 1046 to pass through the spring valve 1066 to the outlet line 1062 for delivery to the eye 100 through the irrigation tube of the irrigation handpiece 1040. The user interface 1060 can be interacted with (e.g., pushed) to overcome the biasing force of the spring 1058 to position the second fluid opening 1056 (e.g., position the second fluid opening 1056 at the second fluid line 1048) to permit fluid flowing through the second fluid line 1048 to pass through the spring valve 1066 to the outlet line 1062 to deliver heated fluid to the lens 112 through the irrigation tube of the irrigation handpiece 1040.

FIG. 38 illustrates a schematic of an aspiration system 1069. The aspiration system 1068 can include an aspiration handpiece 1094, which can at least be aspiration handpiece 1024 and/or include any of the features thereof.

As illustrated, the aspiration system 1069 can include a vacuum line 1074 (e.g., tubing, conduit, hose) that is fluidically coupled with the aspiration handpiece 1094. The vacuum line 1074 can supply a vacuum force (e.g., aspiration force, sucking force) to the aspiration handpiece 1094. As described herein, the aspiration handpiece 1094 can include an aspiration tube that can be introduced into the capsular bag 110 to aspirate fluid, heated fluid, and/or emulsified lens 112. The aspiration handpiece 1094 can include an inlet line 1070 (e.g., tubing, conduit, hose) through which the aspirated material can flow into the aspiration handpiece 1094.

The aspiration handpiece 1094 can include a valve 1104 (e.g., spring valve) that can stop or permit the vacuum force (e.g., aspiration force, sucking force) from the vacuum line 1074 aspirating material through the aspiration tube disposed in the capsular bag 110. The valve 1104 can include an obstruction 1096 (e.g., barrier, flange) to stop flow through the aspiration handpiece 1094, which can include isolating the aspiration tube from the vacuum force of the vacuum line 1074 with the obstruction 1096. The valve 1104 can include a fluid opening 1095 (e.g., flow path) to permit flow through the aspiration handpiece 1094, which can include fluidically connecting the aspiration tube with the vacuum force of the vacuum line 1074. The valve 1104 can include a spring 1098 (e.g., resilient member). The spring 1098 can bias the valve 1104 to position the obstruction 1096 at the inlet line 1070 to stop flow through the aspiration handpiece 1094. The aspiration handpiece 1094 can include the user interface 1060 (e.g., toggle, switch, button, dial, slider, etc.) that can be interacted with (e.g., pushed, pulled, pressed, rotated, etc.) to overcome the biasing force of the spring 1098 to position the fluid opening 1095 at the inlet line 1070 to permit flow through the aspiration handpiece 1094 (e.g., fluidically connect the aspiration tube with the vacuum force of the vacuum line 1074).

The vacuum line 1074 can include a vacuum canister 1086 (e.g., separator canister, container), vacuum regulator 1088, vacuum gauge 1090, and/or vacuum source 1092 (e.g., wall vacuum, pump). The vacuum source 1092 can supply the vacuum force to aspirate material with the aspiration handpiece 1094. The vacuum canister 1086 can collect material (e.g., fluid, emulsified lens 112, etc.) aspirated by the aspiration handpiece 1094. The vacuum regulator 1088 can maintain vacuum pressures, which can be selectively adjusted. The vacuum gauge 1090 can indicate the vacuum pressure in the vacuum line 1074.

Figure 40:
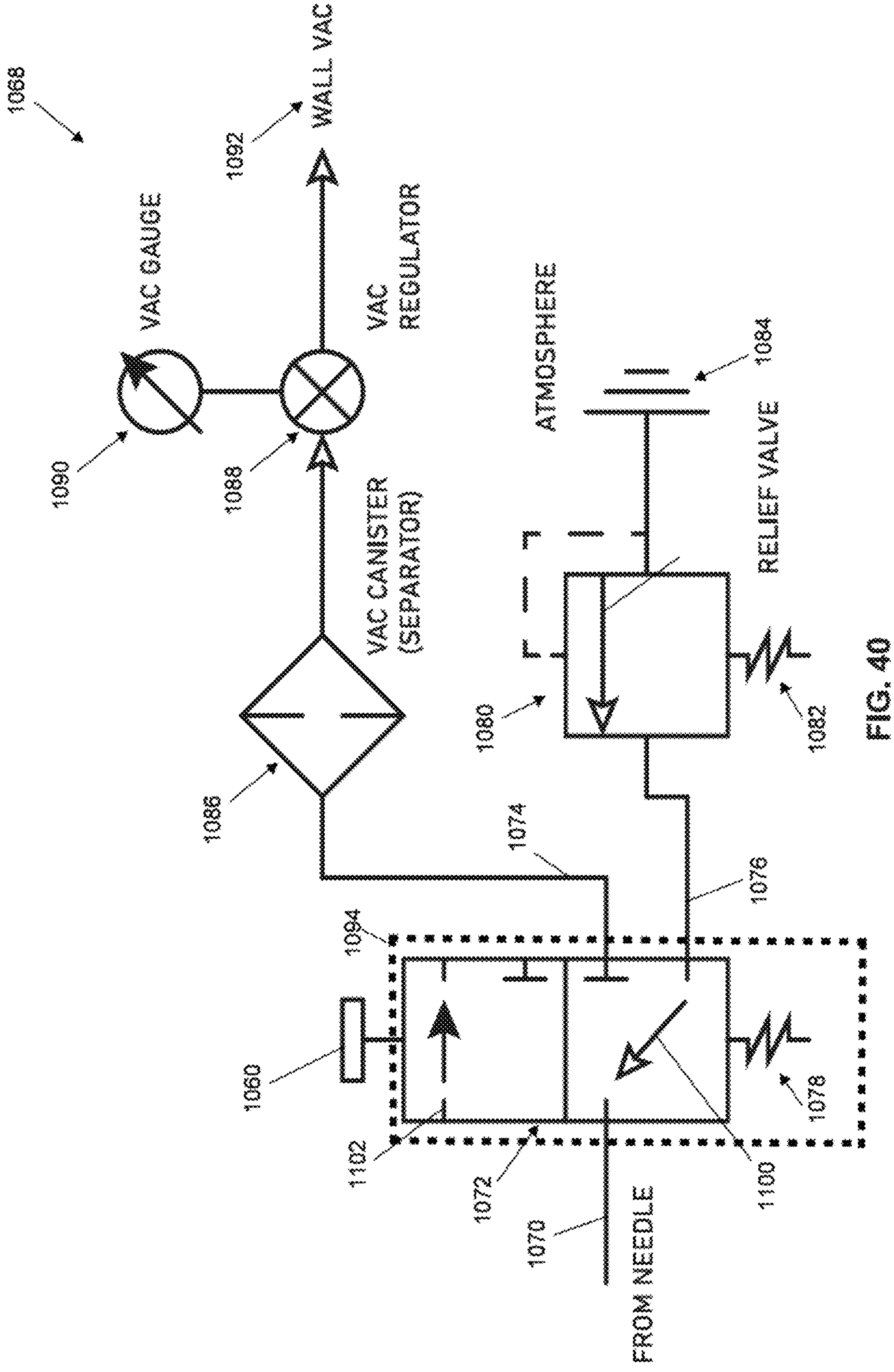
FIG. 40 illustrates a schematic of an aspiration system.

FIG. 40 illustrates an aspiration system 1068, which can include the features of aspiration system 1069. The aspiration system 1068 can include a valve 1072 (e.g., spring valve). The valve 1072 can stop or permit the vacuum force (e.g., sucking force) from the vacuum line 1074 aspirating material through the aspiration tube disposed in the capsular bag 110. The valve 1072 can include a first fluid opening 1100 (e.g., flow path) and a second fluid opening 1102 (e.g., flow path). The valve 1072 can include a spring 1078 that biases the first fluid opening 1100 to a configuration that fluidically connects the inlet line 1070 with a relief line 1076 of the aspiration system 1068. The relief line 1076 can be fluidically coupled to atmospheric pressure 1084 by way of a relief valve 1080 that can be operated with a spring 1082 (e.g., biasing member). The aspiration handpiece 1094 can include the user interface 1060 that can be interacted with (e.g., pushed, pulled, pressed, rotated, etc.) to overcome the biasing force of the spring 1078 such that the vacuum line 1074 is fluidically coupled with the inlet line 1070 by way of the second fluid opening 1102 to aspirate material with the aspiration tube.

Figures 41A, 41B, 41C:
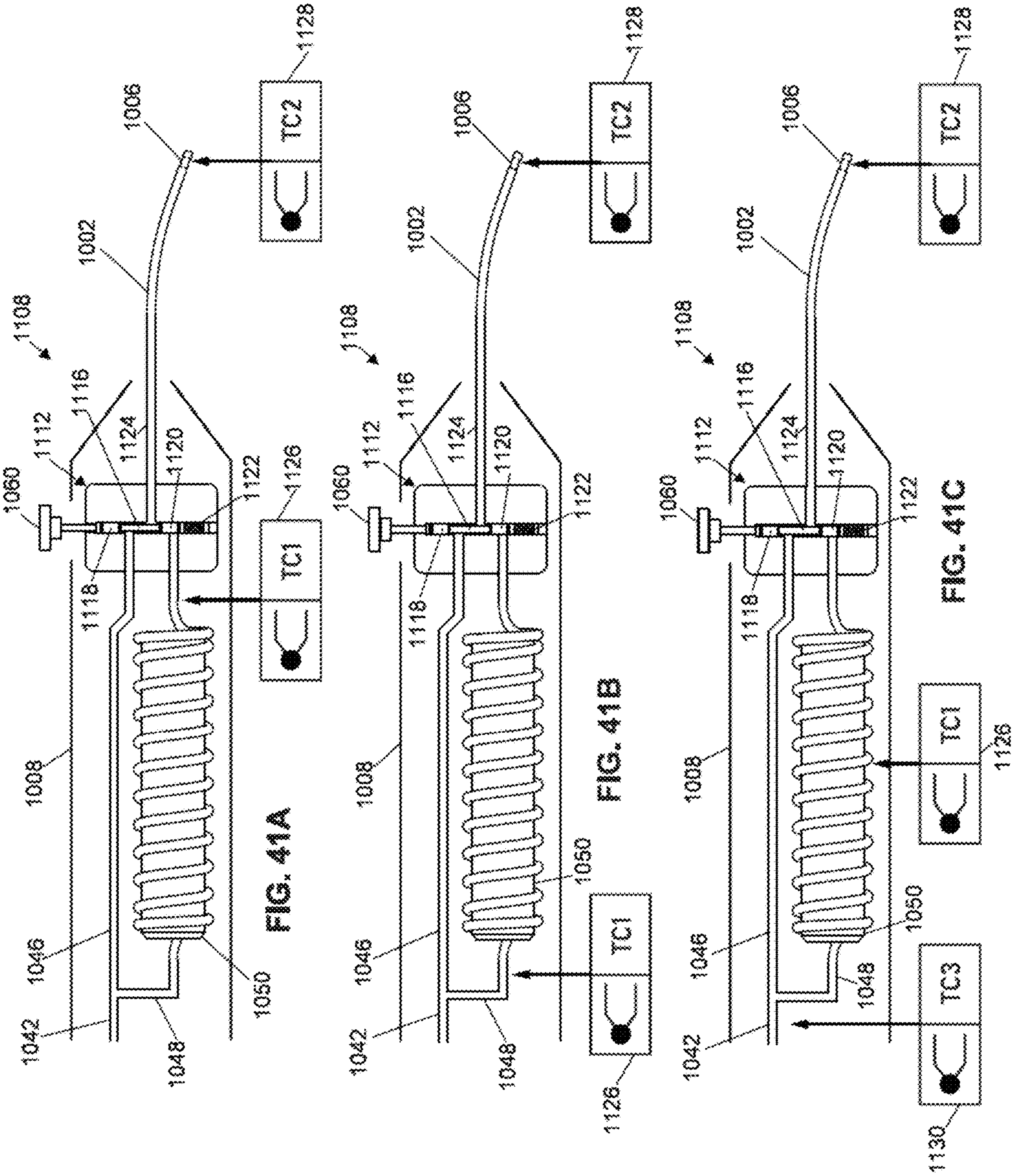
FIGS. 41A-41C illustrate schematics of irrigation handpieces with temperature sensors at different positions.

FIGS. 41A-41C illustrate schematics of an irrigation handpiece 1108 with temperature sensors at different positions. The irrigation handpiece 1108 can be any of the irrigation handpieces described herein (e.g., irrigation handpiece 1000, irrigation handpiece 1022, irrigation handpiece 1040) and/or include any of the features thereof.

As illustrated in FIG. 41A, the second fluid line 1048 can be disposed around the heater 1050 (e.g., cartridge heater) to facilitate heat transfer from the heater 1050 to the fluid in the second fluid line 1048. For example, the second fluid line 1048 can be wrapped around the heater 1050. The second fluid line 1048 can be coiled around the heater 1050.

The irrigation handpiece 1108 can include a valve 1112 (e.g., spring valve). The valve 1112 can include an opening 1116 (e.g., flow path). The opening 1116 can be positioned to fluidically connect the irrigation tube 1002 with the first fluid line 1046 or the second fluid line 1048. The valve 1112 can include a spring 1122 (e.g., resilient member) that can bias the opening 1116 to be positioned at the first fluid line 1046 to fluidically connect the first fluid line 1046 with the irrigation tube 1002 such that fluid flows through the irrigation handpiece 1108 without be routed to the heater 1050. An obstruction 1120 (e.g., barrier, flange, wall) of the valve 1112 can be disposed at the second fluid line 1048 to block flow.

The user interface 1060 can be interacted with (e.g., pushed) to overcome the biasing force of the spring 1122 to position the opening 1116 at the second fluid line 1048 to fluidically connect the second fluid line 1048 with the irrigation tube 1002 such that fluid heated by the heater 1050 flows out of the one or more outlets 1006 of the irrigation tube 1002 to emulsify the lens 112. An obstruction 1118 (e.g., barrier, flange, wall) of the valve 1112 can be disposed at the first fluid line 1046 to block flow.

The irrigation handpiece 1108 can include one or more temperature sensors (e.g., thermocouples), which can be used to monitor temperatures throughout the irrigation handpiece 1108. The sensed temperatures can be used to control energy output by the heater 1050 to maintain the temperature of the heated fluid at the outlet 1006 of the irrigation tube 1002 within a range. The temperature sensors can trigger safety protocols if unsafe temperatures are detected, which can include decreasing energy output by the heater 1050, emitting an alarm notification, and/or stopping the flow of fluid in second fluid line 1048.

The irrigation handpiece 1108 can include a temperature sensor 1128 at the outlet 1006 to monitor a temperature at the location of delivering the heated fluid to the lens 112 for emulsification. The irrigation handpiece 1108 can include a temperature sensor 1126 at the second fluid line 1048 downstream of the heater 1050 but prior to the irrigation tube 1002, which can include upstream of the valve 1112. If the temperature sensed at the outlet 1006 is less than a threshold, the energy output by the heater 1050 can be increased. In some variants, a comparison between the temperatures sensed by the temperature sensor 1128 and temperature sensor 1126 can be used to determine heat loss from the heater 1050 to the outlet 1006. As illustrated in FIG. 41B, in some variants, the temperature sensor 1126 can be disposed at the second fluid line 1048 upstream of the heater 1050, which can help inform how much energy the heater 1050 should apply to the second fluid line 1048. As illustrated in FIG. 41C, in some variants, the temperature sensor 1126 can be disposed at the second fluid line 1048 at the heater 1050. A temperature sensor 1130 can be disposed at the inlet line 1042 upstream of the split between the first fluid line 1046 and the second fluid line 1048, which can be prior to heating the fluid and informative as to how much energy should be applied by the heater 1050 to the second fluid line 1048 to raise the temperature of the fluid therein to a target range.

Figure 42:
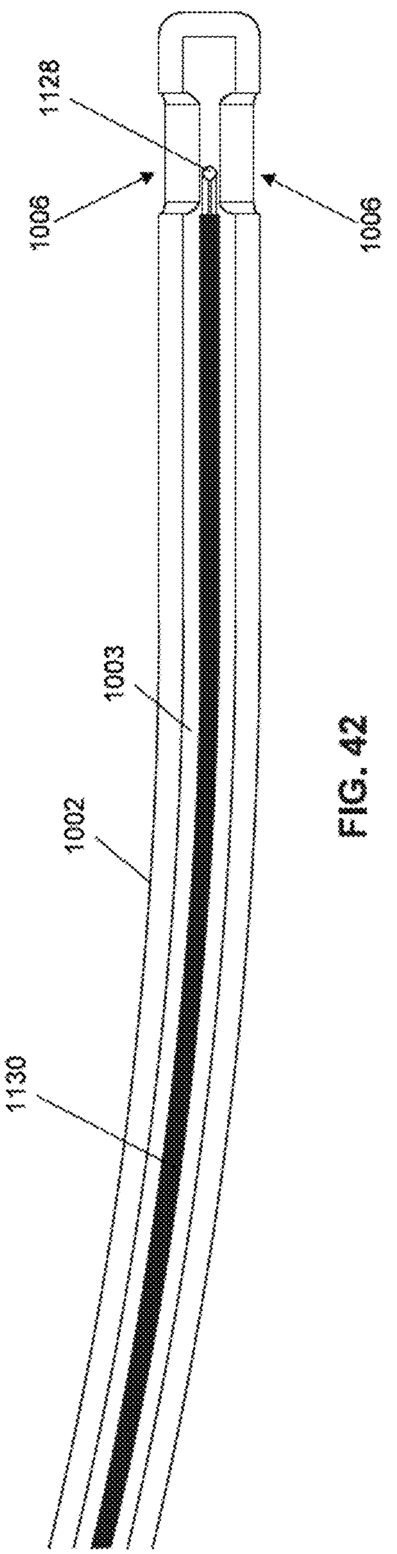
FIG. 42 illustrates a temperature sensor disposed within an irrigation tube of an irrigation handpiece.

FIG. 42 illustrates the temperature sensor 1128 disposed at the one or more outlets 1006. As illustrated, the temperature sensor 1128 can disposed in a lumen 1003 (e.g., cavity, interior) of the irrigation tube 1002 at the one or more outlets 1006, which can facilitate monitoring the temperature of the heated fluid at the point of delivery to the lens 112. Conduit(s) 1130 (e.g., wire(s)) for the temperature sensor 1128 can be routed through the lumen 1003 to communicate temperature data to the irrigation handpiece and/or console (e.g., computing device) with which the irrigation handpiece is in communication.

Figure 43A:
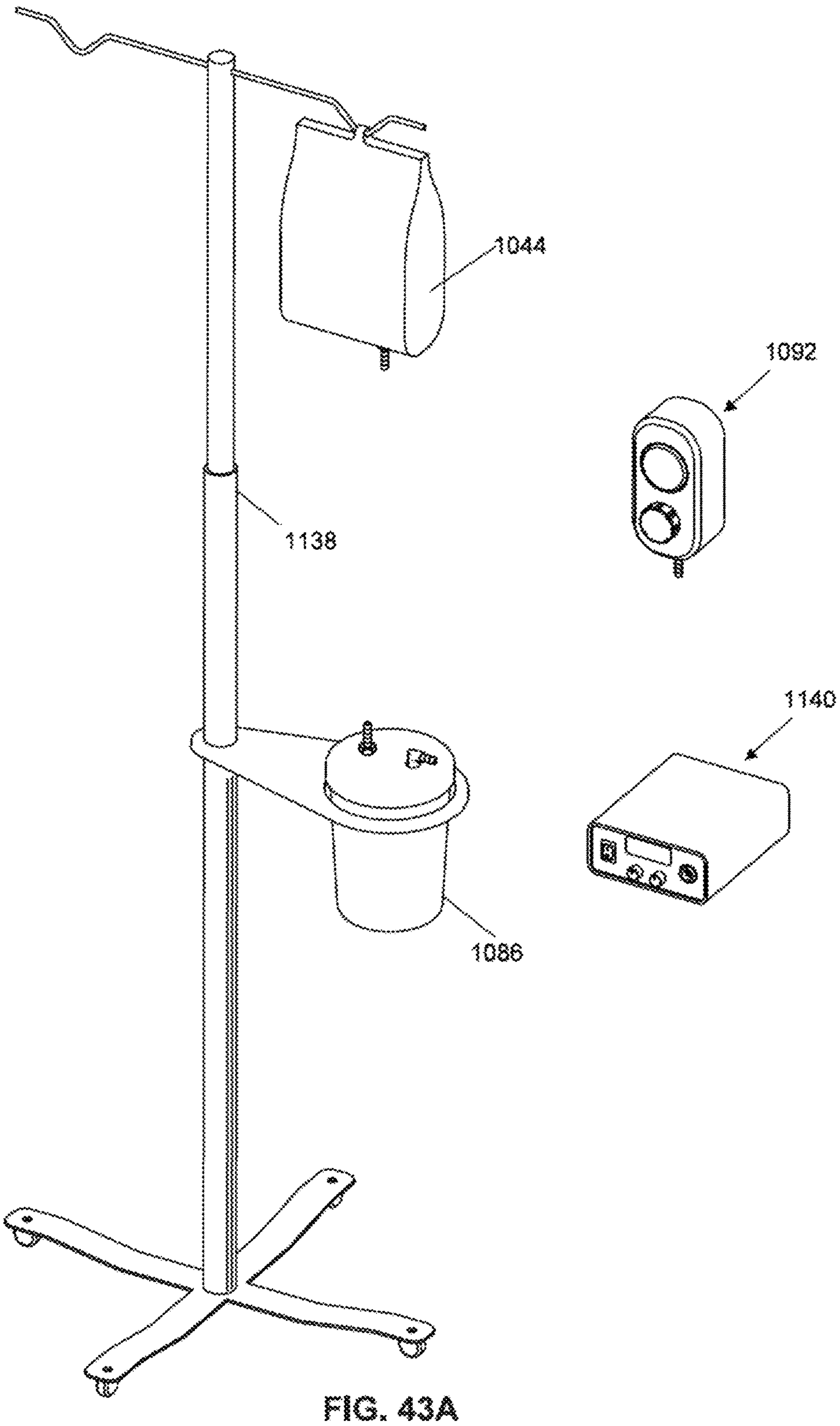
FIG. 43A illustrates an IV pole, reservoir (e.g., IV bag) for fluid, separator (e.g., vacuum canister), wall vacuum, and console to support an irrigation system and/or aspiration system.
Figure 43B:
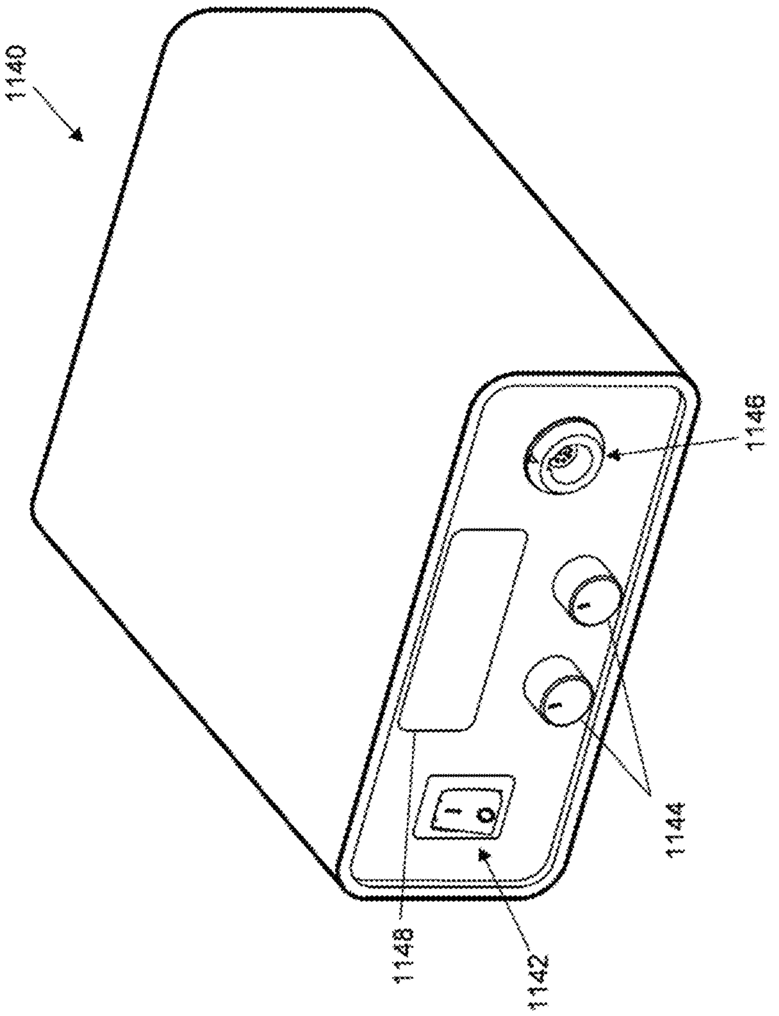
FIG. 43B illustrates the console.
Figure 44A:
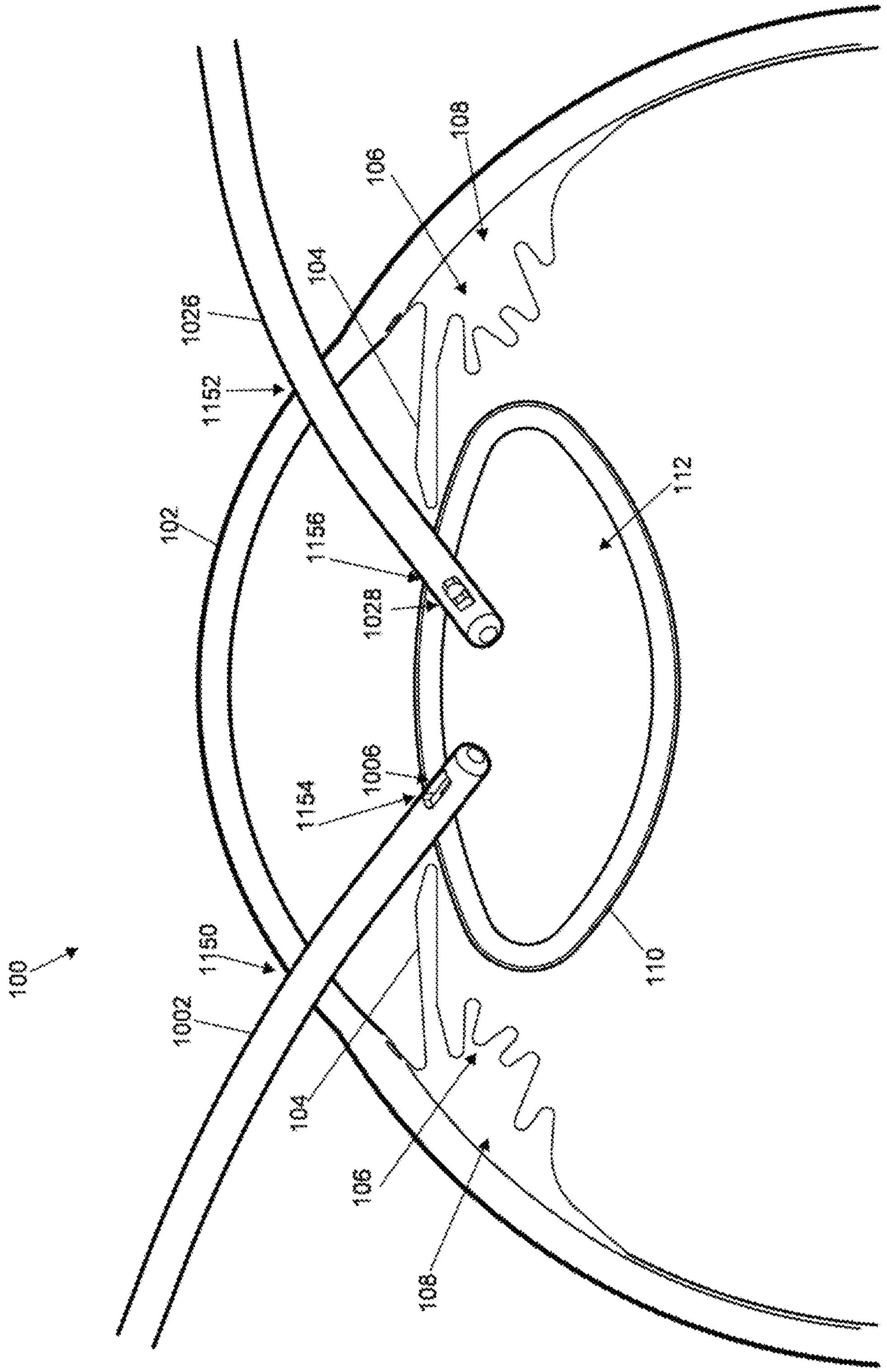
FIGS. 44A and 44B illustrates an irrigation tube and an aspiration tube disposed at a lens of an eye.
Figure 44B:
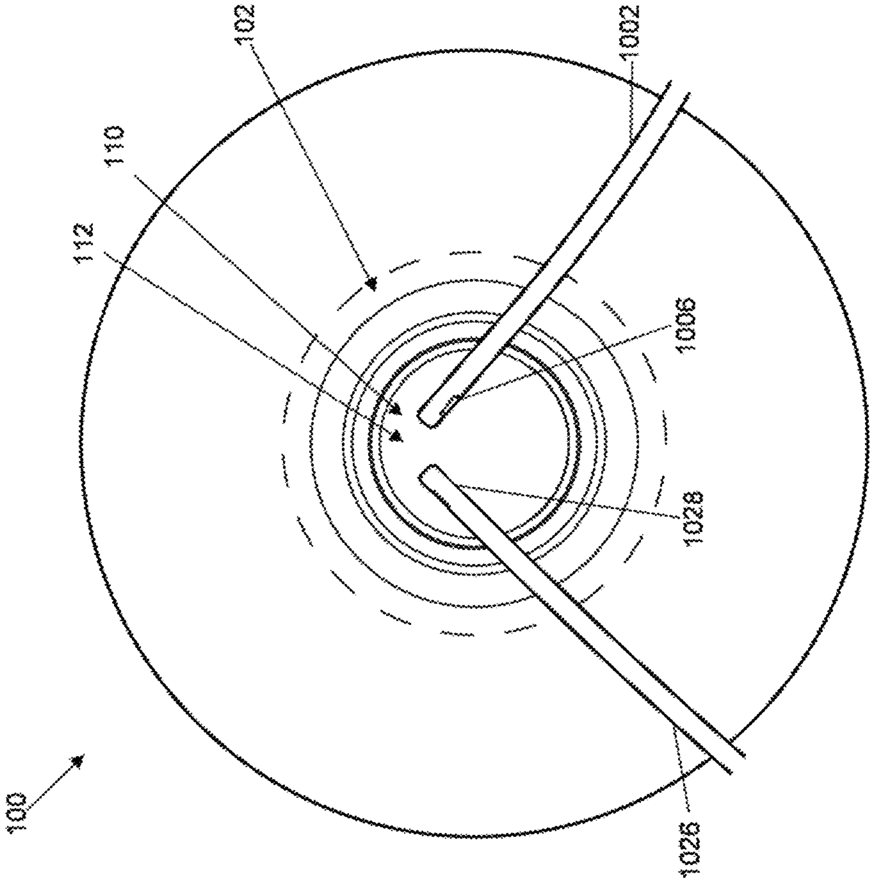
Figure 44C:
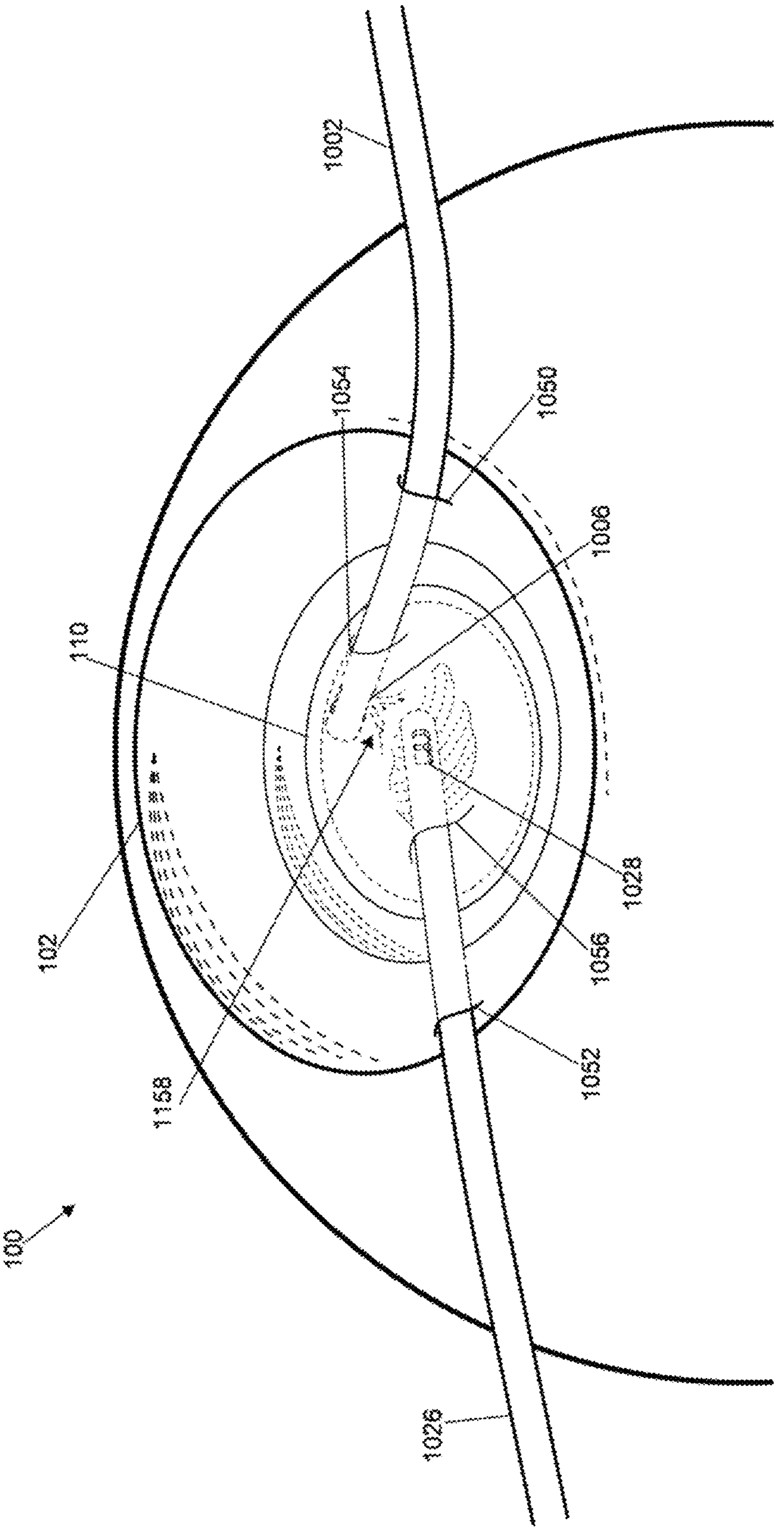
FIG. 44C illustrates the irrigation tube delivering heated fluid to the lens to emulsify the lens and the aspiration tube aspirating the heated fluid and emulsified lens.

FIG. 43A illustrates a pole 1138 (e.g., support, structure, IV pole), vacuum canister 1086, vacuum source interface 1092, and/or console 1140, which can support the irrigation and/or aspiration handpieces described herein. The pole 1138 can support the reservoir 1044. The reservoir 1044 can be disposed at a height to promote flow to the irrigation handpiece fluidically connected with the reservoir 1044. The vacuum canister 1086 can be disposed on the pole 1138. FIG. 43B illustrates the console 1140 which can include a display 1148 (e.g., touchscreen), power switch 1142 (e.g., on/off switch), port 1146 (e.g., interface) to connect with the cable 1012, and user interface(s) 1144 (e.g., dials, toggles, buttons, switches, sliders, etc.) that can be used to control the console 1140 such as electrical energy delivered to the FIGS. 44A and 44B illustrates the irrigation tube 1002 and aspiration tube 1026 positioned to emulsify and aspirate the lens 112 disposed in the capsular bag 110 of the eye 100. To position the irrigation tube 1002 and aspiration tube 1026 at the lens 112, incisions can be made in the cornea 102 and capsular bag 110.

In some variants, Capsulorhexis can be performed to access the lens 112, which can include performing a smaller Capsulorhexis at 2-3 millimeters. In some variants, the Capsulorhexis can be performed off the visual axis of the eye 100, which can include outside an optical zone.

In some variants, as illustrated in FIG. 44A, no Capsulorhexis is performed. The irrigation tube 1002 can be advanced through opening 1150 (e.g., slit, punch, hole) in the cornea 102 and opening 1154 (e.g., slit, punch, hole) in the capsular bag 110. The aspiration tube 1026 can be advanced through opening 1152 (e.g., slit, punch, hole) in the cornea 102 and opening 1156 (e.g., slit, punch, hole) in the capsular bag 110. The openings 1150, 1152, 1154, and 1156 can be cut (e.g., slit). The openings 1150, 1152, 1154, and 1156 can be positioned off the visual axis of the eye 100, which can include being disposed outside of the optical zone. The openings 1150, 1152, 1154, and 1156 can be varying sizes, which can at least include 0.1-3.0 millimeters, 1.0-2.5 millimeters, or less than 2.0 millimeters. These small opening sizes can be used in view of the reduced size (e.g., diameter) of the irrigation tube 1002 and/or aspiration tube 1002, which can include diameters of corresponding sizes. With the irrigation tube 1002 and aspiration tube 1026 positioned, heated fluid 1158 can be delivered to the lens 112 for emulsification through one or more outlets 1006 of the irrigation tube 1002. The one or more inlets 1028 of the aspiration tube 1026 can be disposed proximate and/or facing the one or more outlets 1006 to quickly aspirate the heated fluid and emulsified lens to help localize heat. The irrigation tube 1002 and/or aspiration tube 1026 can be disposed at or proximate the nucleus of the lens 112 at the beginning of emulsification, which can help localize heat within the capsular bag 110. As described herein, the irrigation tube 1002 can deliver fluid not heated by the heater 1050 for irrigation when desired. The temperature of the heated fluid at the one or more outlets 1006 can be those described herein. The temperature can be monitored by one or more temperature sensors, which can guide control of a heater heating the fluid. The lens 112 can be completely emulsified and aspirated using the irrigation tube 1002 and aspiration tube 1026 in under two minutes or less while leaving the capsular bag 110 intact for implantation of an artificial lens. The heated fluid and vacuum flow rates can be low. In some variants, no phacoemulsification techniques are used.

TERMINOLOGY

Although the systems and methods have been disclosed in the context of certain embodiments and examples, it will be understood by those skilled in the art that the systems and methods extend beyond the specifically disclosed embodiments to other alternative embodiments and/or uses of the embodiments and certain modifications and equivalents thereof. Various features and aspects of the disclosed embodiments can be combined with or substituted for one another in order to form varying modes of the thermal systems, devices, and methods disclosed herein. The scope of this disclosure should not be limited by the particular disclosed embodiments described herein.

Methods of using the foregoing system(s) (including device(s), apparatus(es), assembly(ies), structure(s) or the like) are included; the methods of use can include using or assembling any one or more of the features disclosed herein to achieve functions and/or features of the system(s) as discussed in this disclosure. Methods of manufacturing the foregoing system(s) are included; the methods of manufacture can include providing, making, connecting, assembling, and/or installing any one or more of the features of the system(s) disclosed herein to achieve functions and/or features of the system(s) as discussed in this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as “can,” “could,” “might,” or “may” unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language, such as the phrase “at least one of X, Y, and Z,” unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Some embodiments have been described in connection with the accompanying drawings. Components can be added, removed, and/or rearranged. Orientation references such as, for example, “top” and “bottom” are for ease of ease of discussion and may be rearranged such that top features are proximate the bottom and bottom features are proximate the top. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

In summary, various embodiments and examples of thermal systems, devices, and methods have been disclosed. Although the systems and methods have been disclosed in the context of those embodiments and examples, it will be understood by those skilled in the art that this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow.

What is claimed is:

1. An irrigation device comprising:

a housing configured to be handheld;

an inlet configured to receive a fluid, the inlet disposed at a proximal portion of the housing;

a tube comprising a single irrigation lumen and an outlet, the tube disposed at a distal portion of the housing;

a first fluid line disposed inside the housing and downstream of the inlet, the first fluid line terminating upstream of the single irrigation lumen and configured to receive a first portion of the fluid from the inlet and deliver the first portion of the fluid to the single irrigation lumen;

a second fluid line disposed inside the housing and downstream of the inlet, the second fluid line terminating upstream of the single irrigation lumen and configured to receive a second portion of the fluid from the inlet and deliver the second portion of the fluid to the single irrigation lumen;

a temperature sensor;

a heater disposed inside the housing, the heater configured to heat the second portion of the fluid flowing through the second fluid line to form a heated second portion, such that a temperature of the heated second portion of the fluid at the outlet is within a range, wherein the second fluid line is coiled around the heater and the first fluid line bypasses the heater; and a valve disposed inside the housing, on the first fluid line and the second fluid line, downstream of the heater, and upstream of the single irrigation lumen, the first fluid line configured to direct the first portion of the fluid from the inlet to the valve, the second fluid line configured to direct the heated second portion of the fluid from the inlet to the valve, and the valve configured to switch between impeding the first portion of the fluid from flowing through the first fluid line to the single irrigation lumen and the heated second portion of the fluid from flowing through the second fluid line to the single irrigation lumen;

wherein the temperature sensor is disposed at the second fluid line downstream of the heater and upstream of the valve;

wherein the first portion of the fluid and the heated second portion of the fluid do not mix within the housing or the tube; and wherein the single irrigation lumen of the tube is configured to switch between directing the heated second portion of the fluid through the outlet at a lens within a capsular bag of an eye to emulsify the lens and directing the first portion of the fluid through the outlet and into the capsular bag.

2. The irrigation device of claim 1, wherein the valve comprises a spring that biases the valve to a configuration that impedes the second portion of the fluid from flowing through the second fluid line to the single irrigation lumen and permits the first portion of the fluid to flow through the first fluid line to the single irrigation lumen.

3. The irrigation device of claim 2, further comprising a user interface configured to be manipulated to overcome a biasing force of the spring to position the valve in another configuration that permits the second portion of the fluid to flow through the second fluid line to the single irrigation lumen and impedes the first portion of the fluid from flowing through the first fluid line to the single irrigation lumen.

4. The irrigation device of claim 1, wherein the temperature sensor is disposed within a lumen of the second fluid line.

5. The irrigation device of claim 1, further comprising an aspiration lumen disposed in the housing and extending through the tube to the outlet, wherein the aspiration lumen is coaxially positioned inside the single irrigation lumen, wherein the aspiration lumen is configured to receive the lens and the heated second portion of the fluid.

6. The irrigation device of claim 1, wherein the valve has (i) a first state in which the valve fluidly couples the first fluid line to the single irrigation lumen while stopping the second fluid line from fluid communication with the single irrigation lumen, and (ii) a second state in which the valve fluidly couples the second fluid line to the single irrigation lumen while stopping the first fluid line from fluid communication with the single irrigation lumen.

7. An irrigation device comprising:

a housing configured to be handheld;

an inlet configured to receive a fluid, disposed at a proximal portion of the housing;

a single irrigation outlet configured to deliver the fluid to within a capsular bag of an eye, the single irrigation outlet disposed at a distal portion of the housing;

a first fluid line disposed inside the housing and downstream of the inlet, the first fluid line terminating upstream of the single irrigation outlet and configured to receive a first portion of the fluid from the inlet and direct the first portion of the fluid to the single irrigation outlet;

a second fluid line disposed inside the housing and downstream of the inlet, the second fluid line terminating upstream of the single irrigation outlet and configured to receive a second portion of the fluid from the inlet and direct the second portion of the fluid to the single irrigation outlet;

a heater disposed inside the housing, the heater configured to heat the second portion of the fluid flowing through the second fluid line to form a heated second portion of the fluid, wherein the second fluid line is disposed around the heater and the first fluid line bypasses the heater; and a valve disposed inside the housing, on the first fluid line and the second fluid line, downstream of the heater, and upstream of the single irrigation outlet, the first fluid line configured to direct the first portion of the fluid from the inlet to the valve, the second fluid line configured to direct the heated second portion of the fluid from the inlet to the valve, and the valve configured to switch between impeding the first portion of the fluid flowing downstream of the valve and through the first fluid line to the single irrigation outlet and the heated second portion of the fluid flowing through the second fluid line to the single irrigation outlet, wherein the valve is biased to impede the heated second portion of the fluid flowing through the second fluid line to the single irrigation outlet, and wherein the first portion of the fluid and the heated second portion of the fluid do not mix within the housing or the single irrigation outlet.

8. The irrigation device of claim 7, wherein the valve is biased to permit the first portion of the fluid to flow through the first fluid line to the single irrigation outlet.

9. The irrigation device of claim 8, further comprising a user interface that is configured to be manipulated to overcome a biasing force of the valve to permit the second portion of the fluid to flow through the second fluid line to the single irrigation outlet.

10. The irrigation device of claim 7, wherein the second fluid line is coiled around the heater.

11. The irrigation device of claim 7, further comprising a temperature sensor disposed at the single irrigation outlet.

12. The irrigation device of claim 11, wherein the heater is configured to adjust energy output based on a temperature sensed by the temperature sensor.

13. The irrigation device of claim 7, wherein the valve has (i) a first state in which the valve fluidly couples the first fluid line to the single irrigation outlet while stopping the second fluid line from fluid communication with the single irrigation outlet, and (ii) a second state in which the valve fluidly couples the second fluid line to the single irrigation outlet while stopping the first fluid line from fluid communication with the single irrigation outlet.

14. An irrigation device comprising:

a housing configured to be handheld;

an inlet configured to receive a fluid, the inlet disposed at a proximal portion of the housing;

a tube comprising a single irrigation lumen and an outlet configured to deliver the fluid to a lens within a capsular bag of an eye, the tube disposed at a distal portion of the housing;

a first fluid line disposed inside the housing and downstream of the inlet, the first fluid line terminating upstream of the single irrigation lumen and configured to receive a first portion of the fluid from the inlet and deliver the first portion of the fluid to the single irrigation lumen;

a second fluid line disposed inside the housing and downstream of the inlet, the second fluid line terminating upstream of the single irrigation lumen and configured to receive a second portion of the fluid from the inlet and deliver the second portion of the fluid to the single irrigation lumen;

a heater disposed inside the housing, the heater configured to heat the second portion of the fluid in the second fluid line to a temperature to form a heated second portion of the fluid, wherein the first fluid line bypasses the heater; and a valve disposed inside the housing, on the first fluid line and the second fluid line, downstream of the heater, and upstream of the single irrigation lumen, the valve configured to selectively impede the first portion of the fluid from flowing through the first fluid line to the single irrigation lumen and the heated second portion of the fluid from flowing through the second fluid line to the single irrigation lumen, wherein the valve is configured to simultaneously impede the first portion of the fluid flowing downstream of the valve while permitting the heated second portion of the fluid to flow downstream of the valve, and wherein the first portion of the fluid and the heated second portion of the fluid do not mix within the housing or the tube.

15. The irrigation device of claim 14, further comprising a temperature sensor at the outlet, wherein the heater is configured to adjust energy output based on a sensed temperature at the outlet.

16. The irrigation device of claim 14, wherein the second fluid line is disposed around the heater.

17. The irrigation device of claim 14, wherein the valve comprises a spring that biases the valve to a configuration that impedes the second portion of the fluid flowing through the second fluid line to the single irrigation lumen and permits the first portion of the fluid to flow through the first fluid line to the single irrigation lumen.

18. The irrigation device of claim 14, wherein the valve has (i) a first state in which the valve fluidly couples the first fluid line to the single irrigation lumen while stopping the second fluid line from fluid communication with the single irrigation lumen, and (ii) a second state in which the valve fluidly couples the second fluid line to the single irrigation lumen while stopping the first fluid line from fluid communication with the single irrigation lumen.

* * * * *